United States Patent [19]
Fukami et al.

[11] Patent Number: 5,814,631
[45] Date of Patent: Sep. 29, 1998

[54] QUINAZOLINE DERIVATIVES AND APPLICATIONS THEREOF

[75] Inventors: Harukazu Fukami, Kyoto; Akiko Ito, Ibaraki; Shinjiro Niwata, Takatsuki; Saki Kakutani, Ibaraki; Motoo Sumida, Uji; Yoshinobu Kiso, Ibaraki, all of Japan

[73] Assignee: Suntory Limited, Osaka, Japan

[21] Appl. No.: 849,114

[22] PCT Filed: Sep. 27, 1996

[86] PCT No.: PCT/JP96/02830

§ 371 Date: May 8, 1997

§ 102(e) Date: May 8, 1997

[87] PCT Pub. No.: WO97/11941

PCT Pub. Date: Mar. 4, 1997

[30] Foreign Application Priority Data

Sep. 28, 1995 [JP] Japan .................................. 7-285437
May 10, 1996 [JP] Japan .................................. 8-116557

[51] Int. Cl.⁶ .................. A61K 31/495; A61K 31/505; C07D 239/72; C07D 403/02
[52] U.S. Cl. .................. 514/234.5; 514/259; 544/123; 544/284; 544/285
[58] Field of Search .................. 544/123, 284, 544/285; 514/234.5, 259

[56] References Cited

U.S. PATENT DOCUMENTS 4,684,654  8/1987  Wright, Jr. et al. .................. 514/259
4,854,965  8/1989  Bracha et al. .................. 71/92

OTHER PUBLICATIONS

J. Garcia Tercero, et al., "N–Arilsulfonil Ditiocarbamatos de Metilo Como Intermedios en la Sintesis de Heterociclos. Preparacion de Los Sistemas Isomeros 2–Arilsulfonil–amino–3–1, 4H–Benzoxazin–4–Onas Y S–Arilsulfonyl–2–4 (1H, 3H)–Quinazolindionas", *Anales de Quimica*, Ser. C, (1987), 83(2), pp. 247–250.

Hideki Okunishi et al., "Ensho," *Japanese Journal of Inflammation*, vol. 14, pp. 193–197 (1994).

Does the New Angiotensin Converting Enzyme Inhibitor Cilazapril Prevent Restenosis After Percutaneous Transluminal Coronary Angioplasty? *Circulation*, vol. 86, No. 1, pp. 100–110 (1992).

Hidenori Urata et al., "Identification of a Highly Specific Chymase As the Major Angiotensin II–Forming Enzyme in the Human Heart," *Journal Of Biological Chemistry*, vol. 265, pp. 22348–22356 (1990).

Allen Naftilan et al., "Angiotensin II Induces c–fos Expression in Smooth Muscle Via Transcriptional Control," *Hypertension*, vol. 13, pp. 706–711 (1989).

Hideki Okunishi et al., "Different Distribution of Two Types of Angiotensin II–Generating Enzymes in the Aortic Wall," *Biochemical Biophysical Research Communications*, vol. 149, pp. 1186–1192 (1987).

Hideki Okunishi et al., "Evidence for A Putatively New Angiotensin II–Generating Enzyme in the Vascular Wall," *Journal of Hypertension*, vol. 2, pp. 277–284 (1984).

*Helv. Chim. Acta*, vol. 9, pp. 980–991 (1926), H. Rupe.

*Primary Examiner*—Matthew V. Grumbling
*Attorney, Agent, or Firm*—Burns, Doane, Swecker & Mathis, L.L.P.

[57] ABSTRACT

A chymase inhibitor containing as its effective ingredient a quinazoline derivative, or a pharmaceutically acceptable salt thereof, having the formula (1):

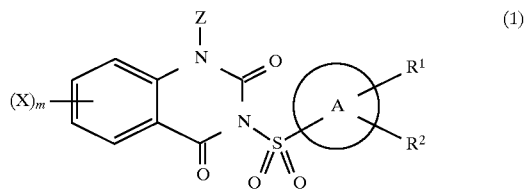

and a pharmaceutical preparation for the prevention of cardiac and circulatory system diseases derived from abnormal exacerbation of Ang II production containing the same as its effective ingredient.

21 Claims, No Drawings

QUINAZOLINE DERIVATIVES AND APPLICATIONS THEREOF

This application claims benefit of priority under 35 U.S.C. §371 from PCT/JP96/02830, filed Sep. 27, 1996.

TECHNICAL FIELD

The present invention relates to a pharmaceutical composition, a medicament for the prevention or treatment of cardiac and circulatory system diseases derived from the abnormal exacerbation of angiotensin II production, and a chymase inhibitor, containing a quinazoline derivative as an effective ingredient, and a novel quinazoline derivative useful as a chymase inhibitor and said pharmaceutical compositions.

BACKGROUND ART

A renin-angiotensin system is one of mechanisms by which the blood pressure of a living body is controlled. Angiotensin I (hereinafter referred to as Ang I) is excised from angiotensinogen biosynthesized in vivo by a renal enzyme renin, and two amino acid residues of C-terminal are cleaved to form angiotensin II (hereinafter referred to as Ang II). It is considered that this Ang II constricts a peripheral blood vessels and stimulates a sympathetic nerve, thereby exhibiting a hypertensive effect. Accordingly, Ang II is an important substance for maintaining the blood pressure. It is however considered that the abnormal acceleration of its production may result in an attack of hypertension or heart failure. From this perspective, attention is paid to the relation between the enzymes converting Ang I to Ang II [angiotensin converting enzymes (hereinafter referred to as ACES)] and diseases of the heart or circulatory organs, including hypertension and various ACE inhibitors have been developed as anti-hypertensive and anti-cardiodysfunctional agents.

Further, recently, it has been revealed that Ang II has, in addition to its actions in constriction of the peripheral blood vessel and stimulation of sympathetic nerves, an action of facilitating cell growth. For example, Naftilan et al. have used cultured cells of a rat vascular smooth muscle to show that Ang II plays an important role in the growth of a vascular smooth muscle cells (see Hypertension, vol. 13, pp. 706–711, 1989). These facts have revealed that Ang II serves as a growth factor for myocardial cells, interstitial cells, angioendothelial cells, and vascular smooth muscle cells and so deeply affects the progress of intravascular stenosis attendant on sclerotic vascular lesions, vascular restenosis after the operation of percutaneous transluminal coronary angioplasty (hereinafter abbreviated as PTCA), arteriosclerosis, peripheral circulatory failure, diabetic and non-diabetic nephropathy, and a morbid state called the remodeling of the ventricle structure after myocardial infarction.

Based on this finding, various attempts have been made to prevent or treat these diseases by suppressing the cell growth-facilitating action of Ang II with an ACE inhibitor. For example, in Europe, the prophylactic effect of the ACE inhibitor cilazapril on vascular restenosis after the operation of PTCA has been evaluated by random multifacility collaboration using a placebo as a control. In this clinical study, however, no statistically significant difference has been recognized between cilazapril and the placebo, therefore the effectiveness of cilazapril in prevention of vascular restenosis after the operation of PTCA could not be confirmed (see Circulation, vol. 86, no. 1, pp. 100–110, 1992).

The results of the above clinical study suggests that Ang II producing pathway in which no ACE participates exists in the human. In fact, Okunishi et al. have identified another enzyme than ACE, which converts Ang I to Ang II in canine, simian, and human arterial tissue (see J. Hypertension, vol. 2, p. 277, 1984 and Biochem. Biophys. Res. Commun., vol. 149, p. 1186, 1987). This enzyme is an enzyme referred to as chymase and belongs to the family of serine proteases. It converts Ang I to Ang II with better efficiency and higher selectivity than ACE. The enzymatic activity of this enzyme is inhibited by chymostatin, but is not inhibited by any ACE inhibitor. Namely, it is considered that in humans, two pathways of the ACE pathway inhibited by an ACE inhibitor and the chymase pathway not inhibited by an ACE inhibitor exist as pathways in which Ang II is produced. In the above clinical study, it is believed that the clinical effect could not be sufficiently achieved even when the ACE pathway was blocked by ACE inhibitor, because the chymase pathway has still functioned.

On the other hand, Urata et al. have purified chymase from the human heart and shown that 70 to 80 percent of the amount of Ang II produced in the heart and blood vessel is accounted for by the chymase pathway (see J. Biol. Chem., vol. 265, pp. 22348–22357, 1990). That is, this report indicated that inhibition of chymase was important for the prevention or treatment of cardiac and circulatory system diseases derived from the abnormal exacerbation of Ang II production and that it was important to inhibit chymase rather than ACE and thereby suggested application of a chymase inhibitor to cardiac and circulatory system diseases.

At the present time, the known inhibitors for chymase are the protein soybean-derived trypsin inhibitor and α-antitrypsin, the peptide derivative chymostatin, the irreversible inhibitor phenylmethylsulfonylfluoride, etc., but the clinical application of the protein soybean-derived trypsin and α-antitrypsin is practically impossible, chymostatin is difficult to put it to practical use since the peptide bonds easily decompose in vivo, and irreversible inhibitor is considered to be impossible to clinical apply it because of its non-selective activity. That is, up to now, no clinically applicable chymase inhibitor has been found. Development of a chymase inhibitor which can be clinically used and would lead to the prevention or treatment of cardiac and circulatory system diseases derived from the abnormal exacerbation of Ang II production is currently being awaited.

DISCLOSURE OF INVENTION

Accordingly, the object of the present invention is to solve the above-mentioned problem and to develop a compound capable of inhibiting chymase and also useful as a medicament for the prevention or treatment of cardiac and circulatory system diseases derived from abnormal exacerbation of Ang II production through intensive synthesis using as an indicator human heart chymase refined by the method of Urata et al. (reference mentioned earlier).

In accordance with the present invention, there are provided a pharmaceutical composition, a medicament for the prevention or treatment of cardiac or circulatory system diseases derived from abnormal exacerbation of Ang II production, and a chymase inhibitor containing, as an effective ingredient, a quinazoline derivative, or a pharmaceutically acceptable salt thereof, having the formula (1):

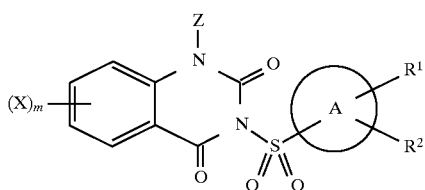

(1)

wherein, the ring A represents a benzene ring, a pyridine ring, a pyrrole ring, or a pyrazole ring, m represents 0, 1, or 2, X represents a hydroxy group, a nitro group, a halogen atom, a $C_1$ to $C_4$ lower alkyl group which may be substituted with a halogen atom, a $C_1$ to $C_4$ lower alkoxy group which may be substituted with a halogen atom, or a $C_7$ to $C_{12}$ aralkyloxy group, or X together with the benzene ring which is shown as substituted with said X, represents a group forming a naphthalene ring or a quinoline ring, $R^1$ and $R^2$ are the same or different and represent a hydrogen atom, a halogen atom, a $C_1$ to $C_4$ lower alkyl group which may be substituted with a halogen atom, a nitro group, a cyano group, a pyrazolyl group, a tetrazolyl group, a carboxyl group which may be esterified with a $C_1$ to $C_4$ lower alkyl group or an allyl group, or a $C_1$ to $C_4$ lower alkoxy group which may be substituted with one or more substituent groups selected from the group consisting of a halogen atom, a morpholino group, a phenylpiperazinyl group, and a carboxyl group which may be esterified with a $C_1$ to $C_4$ lower alkyl group or an allyl group, or, when the ring A represents a benzene ring $R^1$ and $R^2$ together with the benzene ring which is shown as substituted with said $R^1$ and $R^2$ represent a group forming a naphthalene ring or a quinoline ring, and Z represents a hydrogen atom, a $C_1$ to $C_4$ lower alkyl group which may be substituted with a halogen atom, a $C_2$ to $C_5$ alkenyl group, an unsubstituted or substituted aralkyl group, an unsubstituted or substituted aromatic heterocyclic alkyl group, a carboxylmethyl group which may be esterified with a $C_1$ to $C_4$ lower alkyl group or an allyl group, a carbonylmethyl group which is amidated with a primary or secondary or cyclic amine, an unsubstituted or substituted arylcarbonylmethyl group, or an unsubstituted or substituted aralkyloxymethyl group.

BEST MODE FOR CARRYING OUT THE INVENTION

In the general formula (1), the preferable examples of the halogen atom for X are fluorine, chlorine, bromine, or iodine. The examples of the lower alkyl group of the $C_1$ to $C_4$ lower alkyl group for X, which is substituted with a halogen atom, are straight chain alkyl groups such as a methyl group, ethyl group, n-propyl group and n-butyl group, and branched alkyl groups such as an isopropyl group, sec-butyl group and t-butyl group, and, while the examples of the halogen atom of the $C_1$ to $C_4$ lower alkyl group for X which is substituted with a halogen atom, are fluorine, chlorine, bromine and iodine. The examples of the lower alkoxy group of the $C_1$ to $C_4$ lower alkoxy group for X, which is substituted with a halogen atom, are straight chain alkoxy groups such as a methoxy group, ethoxy group, n-propoxy group and n-butoxy group, and branched alkoxy groups such as an isopropoxy group, sec-butoxy group and t-butoxy group, while the examples of the halogen atom of the $C_1$ to $C_4$ lower alkoxy group for X, which is substituted with a halogen atom, are fluorine, chlorine, bromine, and iodine. The examples of the $C_7$ to $C_{12}$ aralkyloxy group for X are a benzyloxy group, phenethyloxy group, phenylpropoxy group and naphthylethyloxy group, etc, preferably the benzyloxy group.

The preferable examples of the halogen atom for $R^1$ or $R^2$ are fluorine, chlorine, bromine, or iodine. The examples of the lower alkyl group of the $C_1$ to $C_4$ lower alkyl group for $R^1$ or $R^2$, which is substituted with a halogen atom, are straight chain alkyl groups such as a methyl group, ethyl group, n-propyl group and n-butyl group, and branched alkyl groups such as an isopropyl group, sec-butyl group and t-butyl group, while the examples of the halogen atom of the $C_1$ to $C_4$ lower alkyl group for $R^1$ or $R^2$, which is substituted with a halogen atom, are fluorine, chlorine, bromine, or iodine. The preferable examples of the $C_1$ to $C_4$ lower alkyl group of the carboxyl group for $R^1$ or $R^2$, which may be esterified with the $C_1$ to $C_4$ lower alkyl group or an allyl group, are straight chain alkyl groups such as a methyl group, ethyl group, n-propyl group and n-butyl group, and branched alkyl groups such as an isopropyl group, sec-butyl group and t-butyl group. The examples of the alkoxy group of the $C_1$ to $C_4$ lower alkoxy group for $R^1$ or $R^2$, which is substituted with one or more substituent groups selected from the group consisting of a halogen atom, a morpholino group, a phenylpiperazinyl group, and a carboxyl group which may be esterified with a $C_1$ to $C_4$ lower alkyl group or an allyl group, are straight chain alkoxy groups such as a methoxy group, ethoxy group, n-propoxy group and n-butoxy group, and branched alkoxy groups such as an isopropoxy group, sec-butoxy group and t-butoxy group. The examples of the halogen atom shown as the above substituent group, are fluorine, chlorine, bromine, or iodine and the preferable examples of the $C_1$ to $C_4$ lower alkyl group of the carboxyl group which is esterified with a $C_1$ to $C_4$ lower alkyl group or an allyl group shown as the above substituent group, are a methyl group, ethyl group, n-propyl group, n-butyl group, and other straight chain alkyl groups and an isopropyl group, sec-butyl group, t-butyl group, and other branched alkyl groups.

The examples of the lower alkyl group of the $C_1$ to $C_4$ lower alkyl group shown as Z which may be substituted with halogen, are straight chain alkyl groups such as a methyl group, ethyl group, n-propyl group and n-butyl group, and branched alkyl groups such as an isopropyl group, sec-butyl group and t-butyl group, while the examples of the halogen atom of the $C_1$ to $C_4$ lower alkyl group which may be substituted with the halogen atom are fluorine, chlorine, bromine, or iodine. The examples of the $C_2$ to $C_5$ alkenyl group for Z are an allyl group, propenyl group, isopropenyl group, butenyl group, etc.

The examples of the aralkyl group of an unsubstituted or substituted aralkyl group shown as Z are a $C_7$ to $C_{12}$ aralkyl group, preferably a benzyl group, phenethyl group, phenylpropyl group, or naphthylethyl group. The preferable examples of the substituent group of an unsubstituted or substituted aralkyl group are a carboxyl group which may be esterified with a $C_1$ to $C_4$ lower alkyl group or an allyl group, a cyano group, a nitro group, a carbonyl group amidized with primary amine, an amine group which may be amidized with a carboxylic acid or an amino acid, and a guanidino group which may be substituted with a lower alkoxycarbonyl group. The examples of the lower alkyl group of the carboxyl group, which may be esterified with a $C_1$ to $C_4$ lower alkyl group or an allyl group are straight alkyl groups such as a methyl group, ethyl group, n-propyl group and n-butyl group, and branched alkyl groups such as an isopropyl group, sec-butyl group and t-butyl group. The examples of the primary amine of the carbonyl group amidized with primary amine are a chain $C_1$ to $C_4$ lower alkylamine or those which may be substituted with carboxyl group, such as, preferably, methylamine, ethylamine, isopropylamine and carboxylmethylanine; amines having monocyclic or polycyclic aromatic hydrocarbon group such as aniline and naphthylamine; amines having aromatic heterocyclic group such as aminopyridine, aminopyrrole, and other. The examples of the carboxylic acid of the amine group which may be amidized with a carboxylic acid or an amino acid are preferably $C_2$ to $C_5$ aliphatic monocarboxylic acids or aliphatic dicarboxylic acids such as pivalic acid and succinic acid, while the examples of the amino acid are amino acids, of which carboxyl group may be esterified or of which amine group may be amidized, such as L-aspartic acid, α-O-t-butyl-N-t-butoxycarbonyl-L-aspartic acid and other. The examples of the guanidino group which may be substituted with a lower alkoxycarbonyl group are preferably a guadinino group which may be substituted with a $C_2$ to $C_5$ lower alkoxycarbonyl group such as a guanidino group and 2, 3-bis-t-butoxycarbonylguanidino group.

The examples of the aromatic heterocyclic alkyl group of an unsubstituted or substituted aromatic heterocyclic alkyl group shown as Z are thienylalkyl groups such as a 2-thenyl group and a 2-thienylethyl group, furylalkyl groups such as a 2-furfuryl group and a 2-furylethyl group, pyridylalkyl groups such as a 2-pyridylmethyl group, 3-pyridylmethyl group, 4-pyridylmethyl group and 4-pyridylethyl group, pyrimidinylalkyl groups such as a 5-pyrimidinylmethyl group, pyrazinylalkyl groups such as a 2-pyrazinylmethyl group, pyridazinylalkyl groups such as a 3-pyridazinylmethyl group tetrazolylalkyl groups such as a 5-tetrazolylmethyl group, isothiazolylalkyl groups such as a 4-isothiazolylmethyl group and a 5-isothiazolylmethyl group, thiazolylalkyl groups such as a 5-thiazolylmethyl group, oxazolylalkyl groups such as a 5-oxazolylmethyl group, and isoxazolylalkyl groups such as a 4-isooxazolylmethyl group and 5-isoxazolylmethyl group. The preferable examples of the substituent group of an unsubstituted or substituted heterocyclic alkyl group, are $C_1$ to $C_4$ lower alkyl groups such as a methyl group and ethyl group, and $C_1$ to $C_4$ carboxyl lower alkyl groups such as a carboxylmethyl group and carboxylethyl group.

The examples of the lower alkyl group of the carboxymethyl group which may be esterified with a $C_1$ to $C_4$ lower alkyl group or an allyl group shown as Z are straight chain alkyl groups such as a methyl group, ethyl group, n-propyl group and n-butyl group, and branched alkyl groups such as an isopropyl group, sec-butyl group and t-butyl group.

The examples of the primary amine of the carbonylmethyl group which may be amidized with primary or secondary or cyclic amine shown as Z are chain $C_1$ to $C_4$ lower alkylamines or those which may be substituted with a carboxyl group such as preferably methylamine, ethylamine, isopropylamine and carboxylmethylamine, and amines having monocyclic saturated hydrocarbon group such as a cyclohexylamine, and amines having monocyclic or polycyclic aromatic hydrocarbon group such as aniline, a benzylamine and a naphthylamine, and amines having aromatic heterocyclic group such as an aminopyridine, an aminomethylpyridine, an aminopyrrole, an aminopyrimidine, an aminoindole and aminoquinoline, wherein the amines having aromatic hydrocarbon group or aromatic heterocyclic group may have on its ring one or more substituent such as 1) hydroxy group,
2) —OPO(OH)$_2$,
3) amino group,
4) oxo group,
5) halogen atom,
6) carboxyl group, which may be esterified with $C_1$ to $C_4$ lower alkyl group such as a methyl group, an ethyl group, an isopropyl group and a t-butyl group, or an allyl group,
7) straight chain or branched $C_1$ to $C_4$ lower alkoxy group such as a methoxy group, an ethoxy group, a n-propoxy group and t-butoxy group, which may be substituted with a carboxyl group, which may be esterified with a $C_1$ to $C_4$ lower alkyl group such as a methyl group, an ethyl group, an isopropyl group and a t-butyl group, or an allyl group,
8) straight chain or branched $C_1$ to $C_4$ lower alkyl groups such as a methyl group, an ethyl group, a n-propyl group, a n-butyl group, an isopropyl group, a sec-butyl group, and t-butyl group, which may be substituted.

Further, the preferable examples of the substituent of the $C_1$ to $C_4$ lower alkyl group, which may be substituted, of the above 8),
  a) a carboxyl group, which may be esterified with $C_1$ to $C_4$ lower alkyl group such as a methyl group, an ethyl group, an isopropyl group and a t-butyl group, or an allyl group,
  b) piperadinyl group, which may be N-substituted with carboxy group which is esterified with $C_1$ to $C_4$ lower alkyl group such as a methyl group, an ethyl group, an isopropyl group and a t-butyl group, or an allyl group,
  c) morpholino group, and
  d) amino group which may be amidized with carboxylic acid or amino acid The examples of the carboxylic acid of amino group of the above d), which may be amidized with carboxylic acid or amino acid, are preferably $C_2$ to $C_5$ aliphatic mono- or dicarboxylic acids such as pivalic acid and succinic acid, while the examples of the amino acid are amino acids of which carboxyl group may be esterified or of which amino group may be amidized, such as a L-aspartic acid, an α-O-t-butyl-N-t-butoxycarbonyl-L-aspartic acid, and a β-O-t-butyl-N-t-butoxycarbonyl-L-aspartic acid. Further, the amine having aromatic heterocyclic group may have the nitrogen atom on its ring, which may be substituted with $C_1$ to $C_4$ lower alkyl group such as a methyl group, and an ethyl group, or carboxy lower alkyl group, which may be esterified, such as a carboxylmethyl group and a t-butoxy carbonylmethyl group.

The examples of the secondary amine of the carbonylmethyl group shown as Z, which is amidized with primary or secondary or cyclic amine are di-lower alkylamines such as a dimethylamine and diethylamine. The examples of the cyclic amine of the carbonylmethyl group shown as Z, which is amidized with primary or secondary or cyclic amine are pyrrolidine and piperidine.

The examples of the arylcarbonylmethyl group of the unsubstituted or substituted arylcarbonylmethyl group shown as Z are a phenylcarbonylmethyl group and a naphthylcarbonylmethyl group, while the preferable examples of the substituent group are a hydroxy group, a nitro group, halogen atoms such as fluorine, chlorine, bromine and iodine, straight or branched $C_1$ to $C_4$ lower alkyl groups, which may be substituted with halogen atom such as methyl group, ethyl group, n-propyl group, n-butyl group, isopropyl group, sec-butyl group and t-butyl group, straight or branched $C_1$ to $C_4$ lower alkoxy groups, which may be substituted with halogen atom, such as methoxy group, ethoxy group, n-propoxy group, n-butoxy group, isopropoxy group, sec-butoxy group and t-butoxy group.

The examples of the aralkyloxymethyl group of the unsubstituted or substituted aralkyloxymethyl group shown as Z, are preferably $C_8$ to $C_{13}$ aralkyloxymethyl groups such as a benzyloxy methyl group, phenethyloxymethyl group and naphthylethyloxymethyl group, while the preferable examples of the substituent group are a hydroxy group, a nitro group, halogen atoms such as fluorine, chlorine, bromine and iodine, straight or branched $C_1$ to $C_4$ lower alkyl groups which may be substituted with halogen atom, such as methyl group, ethyl group, n-propyl group, n-butyl group, isopropyl group, sec-butyl group and t-butyl group, straight or branched $C_1$ to $C_4$ lower alkoxy groups, which may be substituted with halogen atom, such as methoxy group, ethoxy group, n-propoxy group, n-butoxy group, isopropoxy group, sec-butoxy group and t-butoxy group.

Further, the examples of a pharmaceutically acceptable salt are acid salts such as a chlorate and nitrate and alkali metal salts such as a sodium salt, potassium salt.

Further, according to the present invention, there are provided a novel quinazoline derivative, and its pharmaceutically acceptable salts, having the general formula (1'):

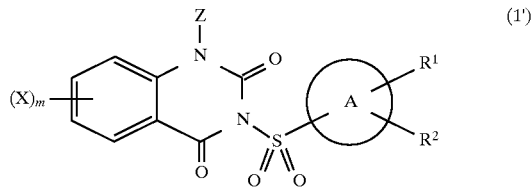

(1')

wherein, the ring A represents a benzene ring, a pyridine ring, a pyrrole ring or a pyrazole ring, m represents 0, 1, or 2, X represents a hydroxy group, a nitro group, a halogen atom, a $C_1$ to $C_4$ lower alkyl group which may be substituted with a halogen atom, a $C_1$ to $C_4$ lower alkoxy group which may be substituted with a halogen atom or $C_7$ to $C_{12}$ aralkyloxy group, or X together with the benzene ring which is shown as substituted with said X represents a group forming a naphthalene ring or a quinoline ring, $R^1$ and $R^2$ are the same or different and represent a hydrogen atom, a halogen atom, a $C_1$ to $C_4$ lower alkyl group which may be substituted with a halogen atom, a nitro group, a cyano group, a pyrazolyl group, a tetrazolyl group, a carboxyl group which may be esterified with a $C_1$ to $C_4$ lower alkyl group or an allyl group, or a $C_1$ to $C_4$ lower alkoxy group which may be substituted with one or more substituent groups selected from the group consisting of a halogen atom, a morpholino group, a phenylpiperazinyl group, and a carboxyl group which may be esterified with a $C_1$ to $C_4$ lower alkyl group or an allyl group, or $R^1$ and $R^2$ together with the benzene ring which is shown as substituted with said $R^1$ and $R^2$, represent a group forming a naphthalene ring or a quinoline ring.

Z represents a hydrogen atom, a $C_1$ to $C_4$ lower alkyl group which may be substituted with a halogen atom, a $C_2$ to $C_5$ alkenyl group, an unsubstituted or substituted aralkyl group, an unsubstituted or substituted aromatic heterocyclic alkyl group, a carboxymethyl group which may be esterified with a $C_1$ to $C_4$ lower alkyl group or an allyl group, a carbonylmethyl group which is amidized with a primary or secondary or cyclic amine, an unsubstituted or substituted arylcarbonylmethyl group, or an unsubstituted or substituted aralkyloxymethyl group, when the ring A represents a benzene ring, Z represents a hydrogen atom and m represents 0, $R^1$ and $R^2$ do not simultaneously represent a hydrogen atom;

when the ring A represents a benzene ring, Z represents a hydrogen atom, m represents 0 and one of $R^1$ or $R^2$ is a hydrogen atom, the other of $R^1$ or $R^2$ represents neither a methyl group nor a chlorine atom;

and when the ring A represents a benzene ring, Z represents a hydrogen atom, m represents 1 and $R^1$ and $R^2$ simultaneously represent a hydrogen atom, X does not represent a chlorine atom, useful as the above pharmaceutical composition, chymase inhibitor, and medicament for the prevention or treatment of cardiac and circulatory system diseases derived from the abnormal exacerbation of angiotensin II production.

In the general formula (1'), the preferable examples of the halogen atom for X are fluorine, chlorine, bromine, or iodine. The examples of the lower alkyl group of the $C_1$ to $C_4$ lower alkyl group for X, which is substituted with a halogen atom, are straight chain alkyl groups such as a methyl group, ethyl group, n-propyl group and n-butyl group, and branched alkyl groups such as an isopropyl group, sec-butyl group and t-butyl group, and, while the examples of the halogen atom of the $C_1$ to $C_4$ lower alkyl group for X which is substituted with a halogen atom, are fluorine, chlorine, bromine and iodine. The examples of the lower alkoxy group of the $C_1$ to $C_4$ lower alkoxy group for X, which is substituted with a halogen atom, are straight chain alkoxy groups such as a methoxy group, ethoxy group, n-propoxy group and n-butoxy group, and branched alkoxy groups such as an isopropoxy group, sec-butoxy group and t-butoxy group, while the examples of the halogen atom of the $C_1$ to $C_4$ lower alkoxy group for X, which is substituted with a halogen atom, are fluorine, chlorine, bromine, and iodine. The examples of the $C_7$ to $C_{12}$ aralkyloxy group for X are a benzyloxy group, phenethyloxy group, phenylpropoxy group and naphthylethyloxy group, etc, preferably the benzyloxy group.

The preferable examples of the halogen atom for $R^1$ or $R^2$ are fluorine, chlorine, bromine, or iodine. The examples of the lower alkyl group of the $C_1$ to $C_4$ lower alkyl group for $R^1$ or $R^2$, which is substituted with a halogen atom, are straight chain alkyl groups such as a methyl group, ethyl group, n-propyl group and n-butyl group, and branched alkyl groups such as an isopropyl group, sec-butyl group and t-butyl group, while the examples of the halogen atom of the $C_1$ to $C_4$ lower alkyl group for $R^1$ or $R^2$, which is substituted with a halogen atom, are fluorine, chlorine, bromine, or iodine. The preferable examples of the $C_1$ to $C_4$ lower alkyl group of the carboxyl group for $R^1$ or $R^2$, which may be esterified with the $C_1$ to $C_4$ lower alkyl group or an allyl group, are straight chain alkyl groups such as a methyl group, ethyl group, n-propyl group and n-butyl group, and branched alkyl groups such as an isopropyl group, sec-butyl group and t-butyl group. The examples of the alkoxy group of the $C_1$ to $C_4$ lower alkoxy group for $R^1$ or $R^2$, which is substituted with one or more substituent groups selected from the group consisting of a halogen atom, a morpholino group, a phenylpiperazinyl group, and a carboxyl group which may be esterified with a $C_1$ to $C_4$ lower alkyl group or an allyl group, are straight chain alkoxy groups such as a methoxy group, ethoxy group, n-propoxy group and n-butoxy group, and branched alkoxy groups such as an isopropoxy group, sec-butoxy group and t-butoxy group. The examples of the halogen atom shown as the above substituent group, are fluorine, chlorine, bromine, or iodine and the preferable examples of the $C_1$ to $C_4$ lower alkyl group of the carboxyl group which is esterified with a $C_1$ to $C_4$ lower alkyl group or an allyl group shown as the above substituent group, are a methyl group, ethyl group, n-propyl group, n-butyl group, and other straight chain alkyl groups and an isopropyl group, sec-butyl group, t-butyl group, and other branched alkyl groups.

The examples of the lower alkyl group of the $C_1$ to $C_4$ lower alkyl group shown as Z which may be substituted with halogen, are straight chain alkyl groups such as a methyl group, ethyl group, n-propyl group and n-butyl group, and branched alkyl groups such as an isopropyl group, sec-butyl group and t-butyl group, while the examples of the halogen atom of the $C_1$ to $C_4$ lower alkyl group which may be substituted with the halogen atom are fluorine, chlorine, bromine, or iodine. The examples of the $C_2$ to $C_5$ alkenyl group for Z are an allyl group, propenyl group, isopropenyl group, butenyl group, etc.

The examples of the aralkyl group of an unsubstituted or substituted aralkyl group shown as Z are a $C_7$ to $C_{12}$ aralkyl group, preferably a benzyl group, phenethyl group, phenylpropyl group, or naphthylethyl group. The preferable examples of the substituent group of an unsubstituted or substituted aralkyl group are a carboxyl group which may be esterified with a $C_1$ to $C_4$ lower alkyl group or an allyl group, a cyano group, a nitro group, a carbonyl group amidized with primary amine, an amine group which may be amidized with a carboxylic acid or an amino acid, and a guanidino group which may be substituted with a lower alkoxycarbonyl group. The examples of the lower alkyl group of the carboxyl group, which may be esterified with a $C_1$ to $C_4$ lower alkyl group or an allyl group are straight alkyl groups such as a methyl group, ethyl group, n-propyl group and n-butyl group, and branched alkyl groups such as an isopropyl group, sec-butyl group and t-butyl group. The examples of the primary amine of the carbonyl group amidized with primary amine are a chain $C_1$ to $C_4$ lower alkylamine or those which may be substituted with carboxyl group, such as, preferably, methylamine, ethylamine, isopropylamine and carboxylmethylamine; amines having monocyclic or polycyclic aromatic hydrocarbon group such as aniline and naphthylamine; amines having aromatic heterocyclic group such as aminopyridine, aminopyrrole, and other. The examples of the carboxylic acid of the amine group which may be amidized with a carboxylic acid or an amino acid are preferably $C_2$ to $C_5$ aliphatic monocarboxylic acids or aliphatic dicarboxylic acids such as pivalic acid and succinic acid, while the examples of the amino acid are amino acids, of which carboxyl group may be esterified or of which amine group may be amidized, such as L-aspartic acid, α-O-t-butyl-N-t-butoxycarbonyl-L-aspartic acid and other. The examples of the guanidino group which may be substituted with a lower alkoxycarbonyl group are preferably a guadinino group which may be substituted with a $C_2$ to $C_5$ lower alkoxycarbonyl group such as a guanidino group and 2, 3-bis-t-butoxycarbonylguanidino group.

The examples of the aromatic heterocyclic alkyl group of an unsubstituted or substituted aromatic heterocyclic alkyl group shown as Z are thienylalkyl groups such as a 2-thenyl group and a 2-thienylethyl group, furylalkyl groups such as a 2-furfuryl group and a 2-furylethyl group, pyridylalkyl groups such as a 2-pyridylmethyl group, 3-pyridylmethyl group, 4-pyridylmethyl group and 4-pyridylethyl group, pyrimidinylalkyl groups such as a 5-pyrimidinylmethyl group, pyrazinylalkyl groups such as a 2-pyrazinylmethyl group, pyridazinylalkyl groups such as a 3-pyridazinylmethyl group tetrazolylalkyl groups such as a 5-tetrazolylmethyl group, isothiazolylalkyl groups such as a 4-isothiazolylmethyl group and a 5-isothiazolylmethyl group, thiazolylalkyl groups such as a 5-thiazolylmethyl group, oxazolylalkyl groups such as a 5-oxazolylmethyl group, and isoxazolylalkyl groups such as a 4-isooxazolylmethyl group and 5-isoxazolylmethyl group. The preferable examples of the substituent group of an unsubstituted or substituted heterocyclic alkyl group, are $C_1$ to $C_4$ lower alkyl groups such as a methyl group and ethyl group, and $C_1$ to $C_4$ carboxyl lower alkyl groups such as a carboxylmethyl group and carboxylethyl group.

The examples of the lower alkyl group of the carboxymethyl group which may be esterified with a $C_1$ to $C_4$ lower alkyl group or an allyl group shown as Z are straight chain alkyl groups such as a methyl group, ethyl group, n-propyl group and n-butyl group, and branched alkyl groups such as an isopropyl group, sec-butyl group and t-butyl group.

The examples of the primary amine of the carbonylmethyl group which may be amidized with primary or secondary or cyclic amine shown as Z are chain $C_1$ to $C_4$ lower alkylamines or those which may be substituted with a carboxyl group such as preferably methylamine, ethylamine, isopropylamine and carboxylmethylamine, and amines having monocyclic saturated hydrocarbon group such as a cyclohexylamine, and amines having monocyclic or polycyclic aromatic hydrocarbon group such as aniline, a benzylamine and a naphthylamine, and amines having aromatic heterocyclic group such as an aminopyridine, an aminomethylpyridine, an aminopyrrole, an aminopyrimidine, an aminoindole and aminoquinoline, wherein the amines having aromatic hydrocarbon group or aromatic heterocyclic group may have on its ring one or more substituent such as 1) hydroxy group,
2) —OPO(OH)$_2$,
3) amino group,
4) oxo group,
5) halogen atom,
6) carboxyl group, which may be esterified with $C_1$ to $C_4$ lower alkyl group such as a methyl group, an ethyl group, an isopropyl group and a t-butyl group, or an allyl group,
7) straight chain or branched $C_1$ to $C_4$ lower alkoxy group such as a methoxy group, an ethoxy group, a n-propoxy group and t-butoxy group, which may be substituted with a carboxyl group, which may be esterified with a $C_1$ to $C_4$ lower alkyl group such as a methyl group, an ethyl group, an isopropyl group and a t-butyl group, or an allyl group,
8) straight chain or branched $C_1$ to $C_4$ lower alkyl groups such as a methyl group, an ethyl group, a n-propyl group, a n-butyl group, an isopropyl group, a sec-butyl group, and t-butyl group, which may be substituted.

Further, the preferable examples of the substituent of the $C_1$ to $C_4$ lower alkyl group, which may be substituted, of the above 8), a) a carboxyl group, which may be esterified with $C_1$ to $C_4$ lower alkyl group such as a methyl group, an ethyl group, an isopropyl group and a t-butyl group, or an allyl group,
b) piperadinyl group, which may be N-substituted with carboxy group which is esterified with $C_1$ to $C_4$ lower alkyl group such as a methyl group, an ethyl group, an isopropyl group and a t-butyl group, or an allyl group, c) morpholino group, and d) amino group which may be amidized with carboxylic acid or amino acid The examples of the carboxylic acid of amino group of the above d), which may be amidized with carboxylic acid or amino acid, are preferably $C_2$ to $C_5$ aliphatic mono- or dicarboxylic acids such as pivalic acid and succinic acid, while the examples of the amino acid are amino acids of which carboxyl group may be esterified or of which amino group may be amidized, such as a L-aspartic acid, an α-O-t-butyl-N-t-butoxycarbonyl-L-aspartic acid, and a β-O-t-butyl-N-t-butoxycarbonyl-L-aspartic acid. Further, the amine having aromatic heterocyclic group may have the nitrogen atom on its ring, which may be substituted with $C_1$ to $C_4$ lower alkyl group such as a methyl group, and an ethyl group, or carboxy lower alkyl group, which may be esterified, such as a carboxylmethyl group and a t-butoxy carbonylmethyl group.

The examples of the secondary amine of the carbonylmethyl group shown as Z, which is amidized with primary or secondary or cyclic amine are di-lower alkylamines such as a dimethylamine and diethylamine. The examples of the cyclic amine of the carbonylmethyl group shown as Z, which is amidized with primary or secondary or cyclic amine are pyrrolidine and piperidine.

The examples of the arylcarbonylmethyl group of the unsubstituted or substituted arylcarbonylmethyl group shown as Z are a phenylcarbonylmethyl group and a naphthylcarbonylmethyl group, while the preferable examples of the substituent group are a hydroxy group, a nitro group, halogen atoms such as fluorine, chlorine, bromine and iodine, straight or branched $C_1$ to $C_4$ lower alkyl groups, which may be substituted with halogen atom such as methyl group, ethyl group, n-propyl group, n-butyl group, isopropyl group, sec-butyl group and t-butyl group, straight or branched $C_1$ to $C_4$ lower alkoxy groups, which may be substituted with halogen atom, such as methoxy group, ethoxy group, n-propoxy group, n-butoxy group, isopropoxy group, sec-butoxy group and t-butoxy group.

The examples of the aralkyloxymethyl group of the unsubstituted or substituted aralkyloxymethyl group shown as Z, are preferably $C_8$ to $C_{13}$ aralkyloxymethyl groups such as a benzyloxy methyl group, phenethyloxymethyl group and naphthylethyloxymethyl group, while the preferable examples of the substituent group are a hydroxy group, a nitro group, halogen atoms such as fluorine, chlorine, bromine and iodine, straight or branched $C_1$ to $C_4$, lower alkyl groups which may be substituted with halogen atom, such as methyl group, ethyl group, n-propyl group, n-butyl group, isopropyl group, sec-butyl group and t-butyl group, straight or branched $C_1$ to $C_4$ lower alkoxy groups, which may be substituted with halogen atom, such as methoxy group, ethoxy group, n-propoxy group, n-butoxy group, isopropoxy group, sec-butoxy group and t-butoxy group.

Further, the examples of a pharmaceutically acceptable salt are acid salts such as a chlorate and nitrate and alkali metal salts such as a sodium salt, potassium salt.

Further, according to the present invention, there is provided a novel quinazoline derivative, and its pharmaceutically acceptable salts, having the general formula (1a):

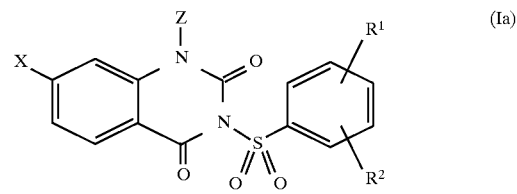

(Ia)

wherein, X represents a hydroxy group, a nitro group, a halogen atom, a $C_1$ to $C_4$ lower alkyl group which may be substituted with a halogen atom, a $C_1$ to $C_4$ lower alkoxy group which may be substituted with a halogen atom, or a $C_7$ to $C_{12}$ aralkyloxy group, or X, together with the benzene ring which is shown as substituted with said X, represents a group forming a naphthalene ring or a quinoline ring, $R^1$ and $R^2$ are the same or different and represent a hydrogen atom, a halogen atom, a $C_1$ to $C_4$ lower alkyl group which may be substituted with a halogen atom, a nitro group, a cyano group, a pyrazolyl group, a tetrazolyl group, a carboxyl group which may be esterified with a $C_1$ to $C_4$ lower alkyl group or an allyl group, or a $C_1$ to $C_4$ lower alkoxy group which may be. substituted with one or more substituent groups selected from the group consisting of a halogen atom, a morpholino group, a phenylpiperazinyl group, and a carboxyl group which may be esterified with a $C_1$ to $C_4$ lower alkyl group or an allyl group, or, $R^1$ and $R^2$ together with the benzene ring which is shown as substituted with said $R^1$ and $R^2$ represent a group forming a naphthalene ring or a quinoline ring, Z represents a hydrogen atom, a $C_1$ to $C_4$ lower alkyl group which may be substituted with a halogen atom, a $C_2$ to $C_5$ alkenyl group, an unsubstituted or substituted aralkyl group, an unsubstituted or substituted aromatic heterocyclic alkyl group, a carboxymethyl group which may be esterified with a $C_1$ to $C_4$ lower alkyl group or an allyl group, a carbonylmethyl group which is amidized with a primary or secondary or cyclic amine, an unsubstituted or substituted arylcarbonylmethyl group, or an unsubstituted or substituted aralkyloxymethyl group, useful as the above pharmaceutical composition, chymase inhibitor, and medicament for the prevention or treatment of cardiac and circulatory system diseases derived from abnormal exacerbation of angiotensin II production and a pharmaceutical composition, chymase inhibitor, and medicament for the prevention or treatment of cardiac and circulatory system diseases derived from abnormal exacerbation of angiotensin II production containing the same as effective ingredients.

In general formula (1a), the preferable examples of the halogen atom for X are fluorine, chlorine, bromine, or iodine. The examples of the lower alkyl group of the $C_1$ to $C_4$ lower alkyl group for X, which is substituted with a halogen atom, are straight chain alkyl groups such as a methyl group, ethyl group, n-propyl group and n-butyl group, and branched alkyl groups such as an isopropyl group, sec-butyl group and t-butyl group, and, while the examples of the halogen atom of the $C_1$ to $C_4$ lower alkyl group for X which is substituted with a halogen atom, are fluorine, chlorine, bromine and iodine. The examples of the lower alkoxy group of the $C_1$ to $C_4$ lower alkoxy group for X, which is substituted with a halogen atom, are straight chain alkoxy groups such as a methoxy group, ethoxy group, n-propoxy group and n-butoxy group, and branched alkoxy groups such as an isopropoxy group, sec-butoxy group and t-butoxy group, while the examples of the halogen atom of the $C_1$ to $C_4$ lower alkoxy group for X, which is substituted with a halogen atom, are fluorine, chlorine, bromine, and iodine. The examples of the $C_7$ to $C_{12}$ aralkyloxy group for X are a benzyloxy group, phenethyloxy group, phenylpropoxy group and naphthylethyloxy group, etc, preferably the benzylqxy group.

The preferable examples of the halogen atom for $R^1$ or $R^2$ are fluorine, chlorine, bromine, or iodine. The examples of the lower alkyl group of the $C_1$ to $C_4$ lower alkyl group for $R^1$ or $R^2$, which is substituted with a halogen atom, are straight chain alkyl groups such as a methyl group, ethyl group, n-propyl group and n-butyl group, and branched alkyl groups such as an isopropyl group, sec-butyl group and t-butyl group, while the examples of the halogen atom of the $C_1$ to $C_4$ lower alkyl group for $R^1$ or $R^2$, which is substituted with a halogen atom, are fluorine, chlorine, bromine, or iodine. The preferable examples of the $C_1$ to $C_4$ lower alkyl group of the carboxyl group for $R^1$ or $R^2$, which may be esterified with the $C_1$ to $C_4$ lower alkyl group or an allyl group, are straight chain alkyl groups such as a methyl group, ethyl group, n-propyl group and n-butyl group, and branched alkyl groups such as an isopropyl group, sec-butyl group and t-butyl group. The examples of the alkoxy group of the $C_1$ to $C_4$ lower alkoxy group for $R^1$ or $R^2$, which is substituted with one or more substituent groups selected from the group consisting of a halogen atom, a morpholino group, a phenylpiperazinyl group, and a carboxyl group which may be esterified with a $C_1$ to $C_4$ lower alkyl group or an allyl group, are straight chain alkoxy groups such as a methoxy group, ethoxy group, n-propoxy group and n-butoxy group, and branched alkoxy groups such as an isopropoxy group, sec-butoxy group and t-butoxy group. The examples of the halogen atom shown as the above substituent group, are fluorine, chlorine, bromine, or iodine and the preferable examples of the $C_1$ to $C_4$ lower alkyl group of the carboxyl group which is esterified with a $C_1$ to $C_4$ lower alkyl group or an allyl group shown as the above substituent group, are a methyl group, ethyl group, n-propyl group, n-butyl group, and other straight chain alkyl groups and an isopropyl group, sec-butyl group, t-butyl group, and other branched alkyl groups.

The examples of the lower alkyl group of the $C_1$ to $C_4$ lower alkyl group shown as Z which may be substituted with halogen, are straight chain alkyl groups such as a methyl group, ethyl group, n-propyl group and n-butyl group, and branched alkyl groups such as an isopropyl group, sec-butyl group and t-butyl group, while the examples of the halogen atom of the $C_1$ to $C_4$ lower alkyl group which may be substituted with the halogen atom are fluorine, chlorine, bromine, or iodine. The examples of the $C_2$ to $C_5$ alkenyl group for Z are an allyl group, propenyl group, isopropenyl group, butenyl group, etc.

The examples of the aralkyl group of an unsubstituted or substituted aralkyl group shown as Z are a $C_7$ to $C_{12}$ aralkyl group, preferably a benzyl group, phenethyl group, phenylpropyl group, or naphthylethyl group. The preferable examples of the substituent group of an unsubstituted or substituted aralkyl group are a carboxyl group which may be esterified with a $C_1$ to $C_4$ lower alkyl group or an allyl group, a cyano group, a nitro group, a carbonyl group amidized with primary amine, an amine group which may be amidized with a carboxylic acid or an amino acid, and a guanidino group which may be substituted with a lower alkoxycarbonyl group. The examples of the lower alkyl group of the carboxyl group, which may be esterified with a $C_1$ to $C_4$ lower alkyl group or an allyl group are straight alkyl groups such as a methyl group, ethyl group, n-propyl group and n-butyl group, and branched alkyl groups such as an isopropyl group, sec-butyl group and t-butyl group. The examples of the primary amine of the carbonyl group amidized with primary amine are a chain $C_1$ to $C_4$ lower alkylamine or those which may be substituted with carboxyl group, such as, preferably, methylamine, ethylamine, isopropylamine and carboxylmethylamine; amines having monocyclic or polycyclic aromatic hydrocarbon group such as aniline and naphthylamine; amines having aromatic heterocyclic group such as aminopyridine, aminopyrrole, and other. The examples of the carboxylic acid of the amine group which may be amidized with a carboxylic acid or an amino acid are preferably $C_2$ to $C_5$ aliphatic monocarboxylic acids or aliphatic dicarboxylic acids such as pivalic acid and succinic acid, while the examples of the amino acid are amino acids, of which carboxyl group may be esterified or of which amine group may be amidized, such as L-aspartic acid, α-O-t-butyl-N-t-butoxycarbonyl-L-aspartic acid and others The examples of the guanidino group which may be substituted with a lower alkoxycarbonyl group are preferably a guadinino group which may be substituted with a $C_2$ to $C_5$ lower alkoxycarbonyl group such as a guanidino group and 2, 3-bis-t-butoxycarbonylguanidino group.

The examples of the aromatic heterocyclic alkyl group of an unsubstituted or substituted aromatic heterocyclic alkyl group shown as Z are thienylalkyl groups such as a 2-thenyl group and a 2-thienylethyl group, furylalkyl groups such as a 2-furfuryl group and a 2-furylethyl group, pyridylalkyl groups such as a 2-pyridylmethyl group, 3-pyridylmethyl group, 4-pyridylmethyl group and 4-pyridylethyl group, pyrimidinylalkyl groups such as a 5-pyrimidinylmethyl group, pyrazinylalkyl groups such as a 2-pyrazinylmethyl group, pyridazinylalkyl groups such as a 3-pyridazinylmethyl group tetrazolylalkyl groups such as a 5-tetrazolylmethyl group, isothiazolylalkyl groups such as a 4-isothiazolylmethyl group and a 5-isothiazolylmethyl group, thiazolylalkyl groups such as a 5-thiazolylmethyl group, oxazolylalkyl groups such as a 5-oxazolylmethyl group, and isoxazolylalkyl groups such as a 4-isooxazolylmethyl group and 5-isoxazolylmethyl group. The preferable examples of the substituent group of an unsubstituted or substituted heterocyclic alkyl group, are $C_1$ to $C_4$ lower alkyl groups such as a methyl group and ethyl group, and $C_1$ to $C_4$ carboxyl lower alkyl groups such as a carboxylmethyl group and carboxylethyl group.

The examples of the lower alkyl group of the carboxymethyl group which may be esterified with a $C_1$ to $C_4$ lower alkyl group or an allyl group shown as Z are straight chain alkyl groups such as a methyl group, ethyl group, n-propyl group and n-butyl group, and branched alkyl groups such as an isopropyl group, sec-butyl group and t-butyl group.

The examples of the primary amine of the carbonylmethyl group which may be amidized with primary or secondary or cyclic amine shown as Z are chain $C_1$ to $C_4$ lower alkylamines or those which may be substituted with a carboxyl group such as preferably methylamine, ethylamine, isopropylamine and carboxylmethylamine, and amines having monocyclic saturated hydrocarbon group such as a cyclohexylamine, and amines having monocyclic or polycyclic aromatic hydrocarbon group such as aniline, a benzylamine and a naphthylamine, and amines having aromatic heterocyclic group such as an aminopyridine, an aminomethylpyridine, an aminopyrrole, an aminopyrimidine, an aminoindole and aminoquinoline, wherein the amines having aromatic hydrocarbon group or aromatic heterocyclic group may have on its ring one or more substituent such as 1) hydroxy group,
2) —OPO(OH)$_2$,
3) amino group,
4) oxo group,
5) halogen atom,
6) carboxyl group, which may be esterified with $C_1$ to $C_4$ lower alkyl group such as a methyl group, an ethyl group, an isopropyl group and a t-butyl group, or an allyl group,
7) straight chain or branched $C_1$ to $C_4$ lower alkoxy group such as a methoxy group, an ethoxy group, a n-propoxy group and t-butoxy group, which may be substituted with a carboxyl group, which may be esterified with a $C_1$ to $C_4$ lower alkyl group such as a methyl group, an ethyl group, an isopropyl group and a t-butyl group, or an allyl group,
8) straight chain or branched $C_1$ to $C_4$ lower alkyl groups such as a methyl group, an ethyl group, a n-propyl group, a n-butyl group, an isopropyl group, a sec-butyl group, and t-butyl group, which may be substituted.

Further, the preferable examples of the substituent of the $C_1$ to $C_4$ lower alkyl group, which may be substituted, of the above 8),
a) a carboxyl group, which may be esterified with $C_1$ to $C_4$ lower alkyl group such as a methyl group, an ethyl group, an isopropyl group and a t-butyl group, or an allyl group,
b) piperadinyl group, which may be N-substituted with carboxy group which is esterified with $C_1$ to $C_4$ lower alkyl group such as a methyl group, an ethyl group, an isopropyl group and a t-butyl group, or an allyl group,
c) morpholino group, and
d) amino group which may be amidized with carboxylic acid or amino acid The examples of the carboxylic acid of amino group of the above d), which may be amidized with carboxylic acid or amino acid, are preferably $C_2$ to $C_5$ aliphatic mono- or di-carboxylic acids such as pivalic acid and succinic acid, while the examples of the amino acid are amino acids of which carboxyl group may be esterified or of which amino group may be amidized, such as a L-aspartic acid, an α-O-t-butyl-N-t-butoxycarbonyl-L-aspartic acid, and a β-O-t-butyl-N-t-butoxycarbonyl-L-aspartic acid. Further, the amine having aromatic heterocyclic group may have the nitrogen atom on its ring, which may be substituted with $C_1$ to $C_4$ lower alkyl group such as a methyl group, and an ethyl group, or carboxy lower alkyl group, which may be esterified, such as a carboxylmethyl group and a t-butoxy carbonylmethyl group.

The examples of the secondary amine of the carbonylmethyl group shown as Z, which is amidized with primary or secondary or cyclic amine are di-lower alkylamines such as a dimethylamine and diethylamine. The examples of the cyclic amine of the carbonylmethyl group shown as Z, which is amidized with primary or secondary or cyclic amine are pyrrolidine and piperidine.

The examples of the arylcarbonylmethyl group of the unsubstituted or substituted arylcarbonylmethyl group shown as Z are a phenylcarbonylmethyl group and a naphthylcarbonylmethyl group, while the preferable examples of the substituent group are a hydroxy group, a nitro group, halogen atoms such as fluorine, chlorine, bromine and iodine, straight or branched $C_1$ to $C_4$ lower alkyl groups, which may be substituted with halogen atom such as methyl group, ethyl group, n-propyl group, n-butyl group, isopropyl group, sec-butyl group and t-butyl group, straight or branched $C_1$ to $C_4$ lower alkoxy groups, which may be substituted with halogen atom, such as methoxy group, ethoxy group, n-propoxy group, n-butoxy group, isopropoxy group, sec-butoxy group and t-butoxy group.

The examples of the aralkyloxymethyl group of the unsubstituted or substituted aralkyloxymethyl group shown as Z, are preferably $C_8$ to $C_{13}$ aralkyloxymethyl groups such as a benzyloxy methyl group, phenethyloxymethyl group and naphthylethyloxymethyl group, while the preferable examples of the substituent group are a hydroxy group, a nitro group, halogen atoms such as fluorine, chlorine, bromine and iodine, straight or branched $C_1$ to $C_4$ lower alkyl groups which may be substituted with halogen atom, such as methyl group, ethyl group, n-propyl group, n-butyl group, isopropyl group, sec-butyl group and t-butyl group, straight or branched $C_1$ to $C_4$ lower alkoxy groups, which may be substituted with halogen atom, such as methoxy group, ethoxy group, n-propoxy group, n-butoxy group, isopropoxy group, sec-butoxy group and t-butoxy group.

Further, the examples of a pharmaceutically acceptable salt are acid salts such as a chlorate and nitrate and alkali metal salts such as a sodium salt, potassium salt.

Among the quinazoline derivatives of general formulae (1), (1'), and (1a) of the present invention, the compounds where both of $R^1$ and $R^2$ are other than a carboxyl group and Z is a hydrogen atom, an unsubstituted or substituted aromatic heterocyclic alkyl group, or an unsubstituted or substituted aralkyl group may be synthesized for example by the Synthesis Method (A) or Synthesis Method (S) shown below.

Synthesis Method (A)

A compound having the formula (2);

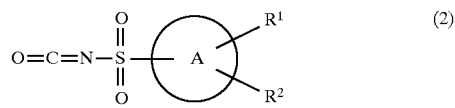

wherein, $R^1$ and $R^2$ represent the same as defined above except for a carboxyl group, or the formula (2a):

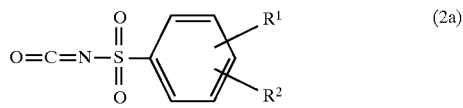

wherein, $R^1$ and $R^2$ represent the same as defined above except for a carboxyl group, is allowed to react with a 2-aminobenzoate derivative having the formula (3):

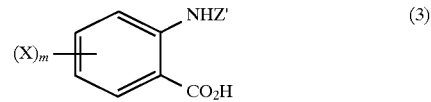

wherein, X and m represent the same as defined above, Z' represents a hydrogen atom, an unsubstituted or substituted aralkyl group or an unsubstituted or substituted aromatic heterocyclic alkyl group, or the formula (3a):

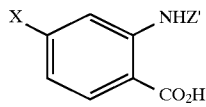

wherein, X represents the same as defined above, Z' represents a hydrogen atom, an unsubstituted or substituted aralkyl group, or an unsubstituted or substituted aromatic heterocyclic alkyl group using, for example, the method described in Japanese Unexamined Patent Publication (Kokai) No. 6-199839, to obtain a compound having the formula (4'):

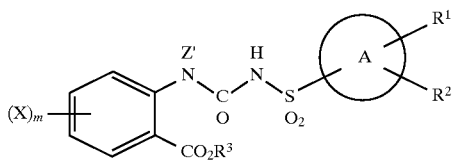

wherein, X and m represent the same as defined above, $R^1$ and $R^2$ represent the same as defined above except for a carboxyl group, Z' represents a hydrogen atom, an unsubstituted or substituted aralkyl group, or an unsubstituted or substituted aromatic heterocyclic alkyl group, and $R^3$ represents a methyl group or ethyl group, or the formula (4'a):

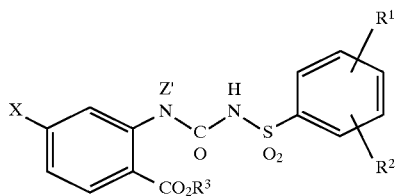

wherein, X represents the same as defined above, $R^1$ and $R^2$ represent the same as defined above except for a carboxyl group, Z' represents a hydrogen atom, an unsubstituted or substituted aralkyl group or an unsubstituted or substituted aromatic heterocyclic alkyl group, and $R^3$ represents a methyl group or ethyl group, then this is hydrolyzed by an alkali to make a urea derivative having the formula (4):

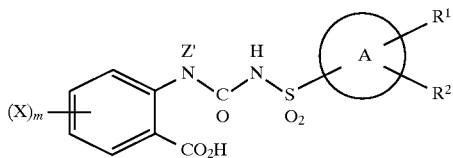

wherein, X and m represent the same as defined above, $R^1$ and $R^2$ represent the same as defined above except for a carboxyl group, Z' represents a hydrogen atom, an unsubstituted or substituted aralkyl group, or an unsubstituted or substituted aromatic heterocyclic alkyl group or the formula (4a):

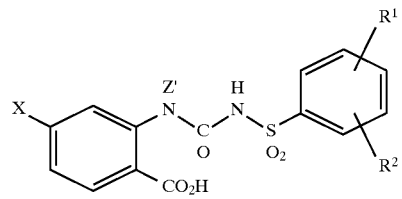

wherein, X represents the same as defined above, $R^1$ and $R^2$ represent the same as defined above except for a carboxyl group, Z' represents a hydrogen atom, an unsubstituted or substituted aralkyl group, or an unsubstituted or substituted aromatic heterocyclic alkyl group, then for example carbonyldiimidazole (hereinafter referred to as CDI) is used to close the quinazoline ring.

The compound having the formula (2) or (2a) used in this reaction may include a commercially available one or one synthesized by a known method. For example, a compound synthesizable from a corresponding sulfonamide derivative using chlorosulfonylisocyanate by the method of synthesis described in European Patent No. 0269141 may be used. For example, benzenesulfonylisocyanate, 4-chlorobenzenesulfonylisocyanate, 2-chlorobenzenesulfonylisocyanate, 4-fluorobenzenesulfonylisocyanate, 2,5-dichlorobenzenesulfonylisocyanate, 2,6-dichlorobenzenesulfonylisocyanate, 4-chloro-2-fluorobenzenesulfonylisocyanate, p-toluenesulfonylisocyanate, 3,4-dimethylbenzenesulfonylisocyanate, 4-trifluoromethylbenzenesulfonylisocyanate, 4-nitrobenzenesulfonylisocyanate, 3-cyanobenzenesulfonylisocyanate, 4-cyanobenzenesulfonylisocyanate, 4-methoxybenzenesulfonylisocyanate, 3,4-dimethoxybenzenesulfonylisocyanate, 3-allyloxycarbonylbenzenesulfonylisocyanate, 4-allyloxycarbonylbenzenesulfonylisocyanate, 4-methoxycarbonylbenzenesulfonylisocyanate, 4-(2-allyloxycarbonylethyl)benzenesulfonylisocyanate, 4-(3-ethyloxycarbonylpropoxy) benzenesulfonylisocyanate, 1-methyl-4-ethoxycarbonylpyrazol-5-sulfonylisocyanate, etc. may be used.

The 2-aminobenzoic acid derivative having the formula (3) or the formula (3a) used in this reaction may include a commercially available one or one synthesized by a known method. For example, 2-aminobenzoic acid and derivatives thereof having, as its substituent group (X)m or X, a 4-chloro group, 4-fluoro group, 5-fluoro group, 5-chloro group, 5-trifluoromethyl group, 6-methyl group, 5-methyl group, 3-methyl group, 4-methyl group, 4-ethyl group, 5-ethyl group, 4-n-propyl group, 5-n-propyl group, 4-iso-propyl group, 5-iso-propyl group, 3-methoxy group, 4-methoxy group, 5-methoxy group, 4-ethoxy group, 5-ethoxy group, 4-nitro group, 5-nitro group, 3,4-dimethyl group, 3,4-dimethoxy group, 4,5-dimethoxy group, 3,4-diethoxy group, 4,5-diethoxy group, 4-benzyloxy group or 5-benzyloxy group, and 3-amino-2-naphthalic acid etc. may be used.

Further, the compounds having the formula (3) or the formula (3a) where Z' represents an unsubstituted or substituted aralkyl group, or an unsubstituted or substituted aromatic heterocyclic alkyl group, may be obtained by reductively N-alkylating a compound having the formula (3) or the formula (3a) where Z' represents hydrogen, using an arylaldehyde or aromatic heterocyclic aldehyde. The arylaldehyde or aromatic heterocyclic aldehyde used in the above method may include a commercially available one or one synthesized by a known method. For example, 2-allyloxycarbonylbenzaldehyde, 2-pyxidinecarboxyaldehyde, 3-pyridinecarboxyaldehyde, 4-pyridinecarboxyaldehyde, 2-furancarboxyaldehyde, 2-thiophencarboxyaldehyde, 5-pyrimidinecarboxyaldehyde, 2-pyradinecarboxyaldehyde, 3-pyridazinecarboxyaldehyde, 5-tetrazolecarboxyaldehyde, 4-isothiazolecarboxyaldehyde, 5-isothiazolecarboxyaldehyde, 5-thiazolecarboxyaldehyde, 5-oxazolecarboxyaldehyde, 4-isoxazolecarboxyaldehyde, 5-isoxazolecarboxyaldehyde, etc. may be used.

The reaction for closing the quinazoline ring from the urea derivative of the formula (4) or (4a) may be performed using an aprotic solvent, for example, ether solvents such as tetrahydrofuran and dioxane, halogen solvents such as methylene chloride or dimethylforinamide etc. at a temperature of –50° C. to 50° C., preferably –20° C. to room temperature. Further, for the ring closing reaction, an ordinary dehydrocondensation agent, for example, carbonyldiimidazole, DCC, and similar carbodiimide compounds, mixed acid anhydrides, etc. may be used.

Synthesis Method (B)

A compound having the formula (5);

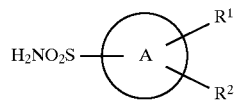

(5)

wherein, $R^1$ and $R^2$ represent the same as defined above except for a carboxyl group or the formula (5a):

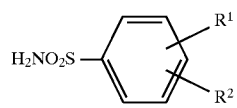

(5a)

wherein, $R^1$ and $R^2$ represent the same as defined above except for a carboxyl group and a 2-aminobenzoic acid ester derivative having the formula (6):

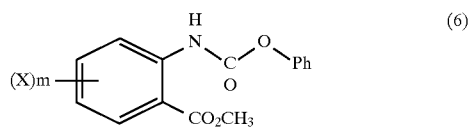

(6)

wherein, X and m represent the same as defined above and Ph represents a phenyl group or the formula (6a):

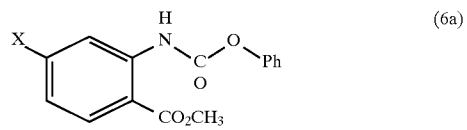

(6a)

wherein, X represents the same as defined above and Ph represents a phenyl group are condensed using, for example, 1,8-diazabicyclo[5,4,0]-7-undecene (hereinafter referred to as DBU) to form a urea derivative methylester, then this is saponified by an alkali to derive the urea derivative having the formula (4) or the formula (4a), then in the same way as in Synthesis Method (A) the quinazoline ring is closed.

The compound of the formula (5) or (5a) used in this reaction may include a commercially available one or one synthesized by a known method. For example, 8-quinoline sulfonamide, 4-toluenesulfonamide, 2-cyanobenzenesulfonamide, 4-chloro-2-cyanobenzenesulfonamide, 4-aminobenzenesulfonamide, 4-acetylbenzenesulfonamide, 4-(5-tetrazole) benzenesulfonamide, 3-pyridinesulfonamide, 2-pyrrolesulfonamide, 1-methyl-2-pyrrolesulfonamide, 3-methyl-4-imidazolesulfonamide, 4-(3-pyrazolyl) benzenesulfonamide, 4-[2-(4-phenyl-1-piperazinyl) ethyloxy]benzenesulfonamide, 4-[2-(1-morpholyl)ethyloxy] benzenesulfonamide, 4-[2-(1-pyrrolidinyl)ethyloxy] benzenesulfonamide, 4-[2-(1-piperizinyl)ethyloxy] benzenesulfonamide, etc. may be used.

The 2-aminobenzoic acid ester derivative of the formula (6) or (6a) used in this reaction may include one which is commercially available or known or can be synthesized by known methods, for example, methyl 4-chloro-2-phenoxycarbonylaminobenzoate, ethyl 4-chloro-2-phenoxycarbonylaminobenzoate, methyl 2-phenoxycarbonylaminobenzoate, ethyl 2-phenoxycarbonylaminobenzoate, etc.

The reaction for causing condensation of the compound having the formula (5) or (5a) and the 2-aminobenzoate derivative having the formula (6) or (6a) to obtain a urea derivative methylester may be performed using an aprotic solvent, for example, ether solvents such as tetrahydrofuran and dioxane, halogen solvents such as methylene chloride, or dimethylformamide, etc. at a temperature of –50° C. to 50° C., preferably –20° C. to room temperature. Further, as the base used in the condensation reaction, organic strong bases such as DBU, inorganic bases such as potassium carbonate, sodium carbonate, potassium hydroxide and sodium hydroxide, or lithium bases such as sodium hydride can be used.

In the reaction for saponification by an alkali of the resultant urea derivative methylester to obtain the formula (4) or (4a) urea derivative, the usual hydrolysis conditions for esters may be used.

Among the quinazoline derivatives having the formula (1), (1'), and (1a), compounds where Z represents a $C_1$ to $C_4$ lower alkyl group which may be substituted with halogen, a $C_2$ to $C_5$ alkenyl group, an unsubstituted or substituted aralkyl group, an unsubstituted or substituted arylcarbonylmethyl group, or an unsubstituted or substituted aralkyloxymethyl group, can, for example, be synthesized by treating the compound where Z represents a hydrogen atom, synthesized in accordance with the above-mentioned Synthesis Method (A) or (B), to alkylation, alkenylation, aralkylation, arylcarbonylmethylation, or aralkyloxymethylation using sodium hydride and a halogenated alkyl, halogenated alkenyl, halogenated aralkyl, halogenated arylcarbonylmethyl, or halogenated aralkyloxymethyl.

Among the above-mentioned compounds, those compounds where Z is a pyridylalkyl group and among the compounds where Z is a carbonylmethyl group which is amidized with a primary or secondary or cyclic amine, the compounds where the primary amine is an amine having aromatic heterocyclic group can have the nitrogen atom on the ring quaternized by a usual technique using alkylating agents such as a halogenated alkyl and a halogenated acetic acid ester.

Further, the substituent group represented by Z in the compounds obtained above may further be suitably modified by known methods. For example, among the compounds where the above-mentioned Z is carbonylmethyl group amidized with a primary or secondary or cyclic amine when Z is a carbonylmethyl group, which is amidized with amine having an aromatic hydrocarbon group and there is a hydroxy group as the substituent group on its ring, N,N'-diethyl-1,5-dihydro-2,4,3-benzodioxaphosphepin-3-amine and other phosphatizing agent may be used to make a phosphoric acid ester.

Note that the above reaction may be performed while protecting the functional groups not involved in the reaction. For example, it may be performed by the step of introducing a carboxymethyl group into a compound where Z is a hydrogen atom, a step of introducing an amidized carbonylmethyl group, a step of quaternizing the nitrogen atom, and a step of introducing a phosphate group.

Further, the protective group used above may be removed by using chemical reduction, catalytic reduction, or an ordinary agent for removing protection in accordance with the type of the protective group. For example, when the protective group is a t-butyl group or t-butoxycarbonyl group, trifluoroacetic acid may be used, while when the protective group is an allyl group, tetrakis (triphenylphosphine) palladium(O) and other palladium catalysts may be used.

Among the quinazoline derivatives having the formula (1), (1'), and (1a), compounds where one of $R^1$ or $R^2$ or both of $R^1$ and $R^2$ are carboxyl groups, for example, can be synthesized from compounds synthesized according to the above Synthesis Method (A) or Synthesis Method (B) where one of $R^1$ or $R^2$ or both of $R^1$ and $R^2$ are an allyloxycarbonyl group by deallylation.

Further, the pharmaceutically acceptable salts of the compound according to the present invention can be obtained by making acid salts or alkali metal salts by the ordinary method.

The chymase inhibitive activity shown by the quinazoline derivatives of the present invention was determined by measuring the rate of conversion of Ang I to Ang II using human heart chymase refined by the method of Urata et al. (see previous reference) and using the method described in that reference (Evaluation Example 1). At the same time, further, the inhibitive activities on the serine protease cathepsin G (evaluation Example 2) and α-chymotrypsin (Evaluation Example 3) were measured. As shown in Table I and Table II, the quinazoline derivatives of the present invention show various strengths of enzyme inhibitive activity with respect to these three types of enzymes. That is, it became clear that by combining in the formula (1), X, $R^1$, $R^2$, Z, and m in various ways, chymase inhibitors with various enzyme inhibitive spectrums could be obtained.

To use the effective ingredient of the present invention as a pharmaceutical preparation for the prevention or treatment of cardiac and circulatory system diseases derived from the abnormal exacerbation of Ang II production, one or more of the compounds of the present invention may be mixed and formed into a form suited to the method of administration by an ordinary method. Examples of preparation forms for oral administration include capsules, tablets, granules, fine granules, syrups, dry syrups, and other preparations, while examples of preparation forms for non-oral administration include injections and besides suppositories such as rectal suppositories and vaginal suppositories, transnasal preparations such as sprays and ointments, and percutaneous preparations such as tapes for percutaneous absorption. Further, in order to enhance the effects of the effective ingredients of the present invention, ACE inhibitors such as alacepril, captopril, cilazapril, which are being clinically applied may be used jointly.

The clinical dose of the compound of the present invention varies according to the diseased condition, degree of seriousness, age, presence of complication, etc. and also varies according to its preparation form. In the case of oral administration, however, it may be dosed usually, in terms of effective ingredients, 1 to 1000 mg per adult per day, preferably 1 to 500 mg, more preferably 5 to 100 mg. In the case of non-oral administration, it is sufficient to administer $\frac{1}{10}$ to $\frac{1}{2}$ the amount of the case of oral administration. These dosages can be suitably adjusted in accordance with the age, the diseased condition, and the like of the patient to be dosed.

The toxicity of the compound according to the present invention is low. For example, the acute toxicity values $LD_{50}$ of the compounds of the later mentioned Examples 1 and 2, upon elapsed time of 24 hours after oral administration to male mice aged 5 weeks were not lower than 1 g/kg. This value is at least 50 times of the clinical dose envisaged, and therefore, the safety of these compounds is judged to be high.

Okunishi et al. (see Hideki Okunishi, Naotaka Shiota, Shinji Takai, Mizuo Miyazaki, "Inflammation" (in Japanese), vol. 14, no. 3, pp. 193–197, 1994) used, as models of balloon injury of the common carotid artery, dogs having the same Ang II producing pathway as the human to study the role of chymase in restenosis after PTCA. This paper reported that when balloon injury is inflicted on the common carotid artery of beagles, hypertrophy occurs in the artery on the injured side, and so ACE and chymase on the injured artery side increase to 4.6 times and 22 times, respectively, at the enzymatic activity level, and also to 4.8 times and 3.4 times, respectively, at the mRNA level as compared with the artery on the control side. It was also described that even in the vascular histological aspect, the Ang II concentration on the injured side increases to about twice the control side. From these experimental findings, Okunishi et al. considered that when physical injury by balloon catheter is inflicted on the vascular wall, gene expression in of both chymase and ACE rises in response to such infliction, and so their enzymatic activities increase, and concluded that the fact that the enzymatic activity of chymase increases about 5 times as much as that of ACE through ACE rather increases than chymase at the mRNA level indicates that chymase plays an important part in the restenosis after PTCA.

From this report, it is considered that topical increase the production of Ang II at the injured site, in which chymase participates, is tied, through the growth factor-like activity of Ang II, with the wandering of the smooth muscle into the tunica intima, its growth in the tunica intima, and the exacerbation of production of extracellular substrate, and consequently causes the restenosis. The quinazoline derivatives according to the present invention, as shown in the later evaluation examples, inhibit human heart chymase. This strongly suggests that the compounds according to the present invention suppress the excess production of Ang II through inhibition of the chymase activity and thereby lead to the prevention or treatment of cardiac and circulatory system diseases derived from the abnormal exacerbation of Ang II production.

As examples of such diseases, cardiac insufficiency, hypercardia, stasis cardiac diseases, hypertension, arteriosclerosis, peripheral circulatory disorders, revasoconstriction after PCTA, diabetic renal disorders or non-diabetic renal disorders, etc. may be given as examples. These diseases are caused by enlargement of the heart or angioendothelia due to the growth factor-like activity of Ang II in the heart, peripheral arteries, and kidneys, and therefore, the quinazoline derivatives of the present invention are believed to lead to the prevention or treatment of these cardiac and circulatory system diseases through inhibition of the chymase activity.

EXAMPLES

The present invention will now be further illustrated by, but is by no means limited to, the following Examples.

Example 1
Synthesis of 7-chloro-3-(-4-chlorobenzenesulfonyl)-2,4(1H,3H)-quinazolinedione (Compound 1)

Following Synthesis Method (A), into 200 ml of anhydrous tetrahydrofuran (hereinafter referred to as THF) was dissolved 4.90 g (22.5 mmol) of 4-chlorobenzenesulfonylisocyanate, then 3.51 g (20.5 mmol) of 2-amino-4-chlorobenzoic acid was added and the mixture was stirred at room temperature for two hours. The reaction solution was cooled by ice water, then 3.98 g (24.55 mmol) of CDI was added and the mixture was stirred under ice cooling for 30 minutes. An excess amount of water was poured into the reaction solution, then the precipitated crystal was obtained by filtration and the obtained crystal was washed by water, then was washed by ethyl acetate to obtain 5.03 g of the above-identified compound (yield 66.5%). Properties: colorless crystal, Melting point: 286°–287° C., PMR ($\delta$ppm, DMSO-$d_6$): 7.12 (1H,s), 7.23 (1H,d), 7.26 (2H,d), 7.86 (1H,d), 8.17 (2H,d), 11.71 (1H,br).

Example 2
Synthesis of 3-(4-chlorobenzenesulfonyl)-5-methyl-2,4(1H,3H)-quinazolinedione (Compound 2)

2.00 g (9.19 mmol) of 4-chlorobenzenesulfonylisocyanate and 1.26 g (8.33 mmol) of 2-amino-6-methylbenzoic acid were treated in the same way as in Example 1 to obtain 2.50 g of the above-identified compound (yield 85.6%). Properties: colorless crystal, Melting point: >250° C., PMR ($\delta$ppm, DMSO-$d_6$): 2.56 (3H,s), 6.99 (2H,t), 7.49 (1H,t), 7.77 (2H,d), 8.20 (2H,d), 11.54 (1H,br).

Example 3
Synthesis of 3-(4-chlorobenzenesulfonyl)-6-methyl-2,4 (1H,3H)-quinazolinedione (Compound 3)

2.75 g (12.6 mmol) of 4-chlorobenzenesulfonylisocyanate and 1.74 g (11.5 mmol) of 2-amino-5-methylbenzoic acid were treated in the same way as in Example 1 to obtain 2.47 g of the above-identified compound (yield 53.3%). Properties: colorless crystal, Melting point: 251°–253° C., PMR ($\delta$ppm, DMSO-$d_6$): 2.32 (3H,s), 7.03 (1H,d), 7.48 (1H,t), 7.66 (2H,d), 7.75 (2H,d), 8.16 (2H,d), 11.53 (1H,br).

Example 4
Synthesis of 3-(4-chlorobenzenesulfonyl)-8-methyl-2,4(1H,3H)-quinazolinedione (Compound 4)

2.00 g (9.19 mmol) of 4-chlorobenzenesulfonylisocyanate and 1.26 g (8.33 mmol) of 2-amino-3-methylbenzoic acid were treated in the same way as in Example 1 to obtain 2.86 g of the above-identified compound (yield 98.0%). Properties: colorless crystal, Melting point: 221°–225° C., PMR ($\delta$ppm, DMSO-$d_6$): 2.32 (3H,s), 7.12 (1H,t), 7.51 (1H,d), 7.72 (1H,d), 7.76 (2H,d), 8.19 (2H,d), 11.10 (1H,br).

Example 5
Synthesis of 3-(4-allyloxycarbonylbenzenesulfonyl)-7-chloro-2,4(1H,3H)-quinazolinedione (Compound 5)

1.10 g (4.15 mmol) of 4-allyloxycarbonylbenzenesulfonylisocyanate and 712 mg (4.15 mmol) of 2-amino-4-chlorobenzoic acid were treated in the same way as in Example 1 to obtain 657 mg of the above-identified compound (yield 37.6%). Properties: colorless crystal, Melting point: 130°–132° C., PMR ($\delta$ppm, DMSO-$d_6$): 4.59 (2H,d), 5.18 (1H,d), 5.27 (1H,d), 5.87–5.94 (1H,m), 7.13 (1H,s), 7.22 (1H,d), 7.62–7.70 (2H,m), 7.86 (1H,d), 8.09 (2H,d), 11.63 (1H,br).

Example 6
Synthesis of 3-(4-carboxybenzenesulfonyl)-7-chloro-2,4(1H,3H)-quinazolinedione (Compound 6)

538 mg (1.28 mmol) of the compound 5 was dissolved in 20 ml of a THF/formic acid (9/1) mixture, then 150 mg of triphenylphosphine was added. Next, the reaction vessel was reduced in pressure and the inside replaced with nitrogen, then 150 mg of tetrakis(triphenylphosphine)palladium(0) was added and the mixture was stirred while blocked from light at room temperature for 16 hours. The reaction solution was concentrated under reduced pressure and the obtained solid was washed by dichloromethane to obtain 342 mg of the above-identified compound (yield 70.2%). Properties: colorless crystal, Melting point: >200° C., PMR ($\delta$ppm, DMSO-$d_6$): 7.13 (1H,s), 7.23 (1H,d), 7.61–7.69 (2H,m), 7.86 (1H,d), 8.05 (2H,d), 12.07 (1H,br).

Example 7
Synthesis of 3-(4-chlorobenzenesulfonyl)-8-methoxy-2,4(1H,3H)-quinazolinedione (Compound 7)

2.00 g (9.19 mmol) of 4-chlorobenzenesulfonylisocyanate and 1.40 g (8.38 mmol) of 2-amino-3-methoxybenzoic acid were treated in the same way as in Example 1 to obtain 2.58 g of the above-identified compound (yield 84.0%). Properties: colorless crystal, Melting point: 220°–222° C., PMR ($\delta$ppm, DMSO-$d_6$): 3.88 (3H,s), 7.16 (1H,t), 7.32 (1H,d), 7.43 (1H,d), 7.76 (2H,d), 8.17 (2H,d), 10.95 (1H,br).

Example 8
Synthesis of 7-chloro-3-(3-cyanobenzenesulfonyl)-2,4(1H,3H)-quinazolinedione (Compound 8)

1.14 g (5.49 mmol) of 3-cyanobenzenesulfonylisocyanate and 943 mg (5.50 mmol) of 2-amino-4-chlorobenzoic acid were treated in the same way as in Example 1 to obtain 399 mg of the above-identified compound (yield 20.0%). Properties: colorless crystal, Melting point: 225°–226° C., PMR ($\delta$ppm, DMSO-$d_6$); 7.13 (1H,s), 7.24 (1H,d), 7.89 (2H,m), 8.24 (1H,d), 8.43 (1H,d), 8.55 (1H,s), 11.76 (1H,br).

Example 9
Synthesis of 7-chloro-3-(3,4-dimethylbenzenesulfonyl)-2,4(1H,3H)-quinazolinedione (Compound 9)

582 mg (2.76 mmol) of 3,4-dimethylbenzenesulfonylisocyanate and 473 mg (2.76 mmol) of 2-amino-4-chlorobenzoic acid were treated in the same way as in Example 1 to obtain 190 mg of the above-identified compound (yield 18.9%). Properties: colorless crystal, Melting point: >250° C., PMR ($\delta$ppm, DMSO-$d_6$): 2.33 (6H,s), 7.12 (1H,s), 7.23 (1H,d), 7.43 (1H,d), 7.84–7.91 (3H,m), 11.64 (1H,br).

Example 10
Synthesis of 7-chloro-3-(3,4-dimethoxybenzenesulfonyl)-2,4(1H,3H)-quinazolinedione (Compound 10)

897 mg (3.69 mmol) of 3,4-dimethoxybenzenesulfonylisocyanate and 633 mg (3.69 mmol) of 2-amino-4-chlorobenzoic acid were treated in the same way as in Example 1 to obtain 512 mg of the above-identified compound (yield 35.0%). Properties: colorless crystal, Melting point: >250° C., PMR ($\delta$ppm, DMSO-$d_6$): 3.85 (3H,s), 3.88 (3H,s), 7.12 (1H,s), 7.22 (2H,d), 7.67 (1H,s), 7.77 (1H,d), 7.86 (1H,d), 11.63 (1H,br).

Example 11
Synthesis of 7-chloro-3-benzenesulfonyl-2,4 3(1H,3H)-quinazolinedione (Compound 11)

1.09 g (5.46 mmol) of benzenesulfonylisocyanate and 929 mg (5.41 mmol) of 2-amino-4-chlorobenzoic acid were treated in the same way as in Example 1 to obtain 1.27 g of the above-identified compound (yield 69.7%). Properties: colorless crystal, Melting point: 282°–284° C., PMR (δppm, DMSO-$d_6$): 7.12 (1H,s), 7.22 (1H,d), 7.68 (2H,t), 7.79 (1H,t), 7.86 (1H,d), 8.17 (2H,d), 11.66 (1H,br).

Example 12
Synthesis of 3-(4-chlorobenzenesulfonyl)-6-methoxy-2,4 (1H,3H)-quinazolinedione (Compound 12)

1.00 g (4.59 mmol) of 4-chlorobenzenesulfonylisocyanate and 698 mg (4.18 mmol) of 2-amino-5-methoxybenzoic acid were treated in the same way as in Example 1 to obtain 992 mg of the above-identified compound (yield 64.8%). Properties: colorless crystal, Melting point: 192°–194° C., PMR (δppm, DMSO-$d_6$): 3.79 (3H,s), 7.08 (1H,d), 7.30 (2H,m), 7.75 (2H,d), 8.16 (2H,d), 11.48 (1H,br).

Example 13
Synthesis of 7-chloro-3-(4-nitrobenzenesulfonyl)-2,4(1H, 3H)-quinazolinedione (Compound 13)

1.13 g (4.95 mmol) of 4-nitrobenzenesulfonylisocyanate and 849 mg (4.95 mmol) of 2-amino-4-chlorobenzoic acid were treated in the same way as in Example 1 to obtain 610 mg of the above-identified compound (yield 32.3%). Properties: colorless crystal, Melting point: >250° C., PMR (δppm, DMSO-$d_6$): 7.13 (1H,s), 7.24 (1H,d), 7.87 (1H,d), 8.42 (2H,d), 8.48 (2H,d), 11.93 (1H,br).

Example 14
Synthesis of 7-chloro-1-(3-allyloxycarbonylbenzenesulfonyl)-2,4(1H,3H)-quinazolinedione (Compound 14)

1.66 g (6.22 mmol) of 3-allyloxycarbonylbenzenesulfonylisocyanate and 1.07 g (6.24 mmol) of 2-amino-4-chlorobenzoic acid were treated in the same way as in Example 1 to obtain 1.07 g of the above-identified compound (yield 40.9%). Properties: colorless crystal, Melting point: 187°–189° C., PMR (δppm, DMSO-$d_6$): 4.88 (2H,d), 5.31 (1H,d), 5.44 (1H,d), 6.02–6.12 (1H,m), 7.11 (1H,s), 7.22 (1H,d), 7.84–7.93 (2H, m), 8.35 (1H,d), 8.44 (1H,d), 8.73 (1H,s), 11.68 (1H,br).

Example 15
Synthesis of 3-(3-carboxybenzenesulfonyl)-7-chloro-2,4 (1H,3H)-quinazolinedione (Compound 15)

500 mg (1.19 mmol) of the compound 14 was treated in the same way as in Example 6 to obtain 338 mg of the above-identified compound (yield 74.6%). Melting point: >250° C., PMR (δppm, DMSO-$d_6$): 7.12 (1H,s), 7.23 (1H, d), 7.81–7.88 (2H,m), 8.30 (1H,d), 8.39 (1H,d), 8.69 (1H,s), 11.63 (1H,br), 13.49 (1H,br).

Example 16
Synthesis of 7-choro-3-(4-fluorobenzenesulfonyl)-2,4(1H, 3H)-quinazolinedione (Compound 16)

1.72 g (8.57 mmol) of 4-fluorobenzenesulfonylisocyanate and 1.47 g (8.57 mmol) of 2-amino-4-chlorobenzoic acid were treated in the same way as in Example 1 to obtain 815 mg of the above-identified compound (yield 26.8%). Properties: colorless crystal, Melting point: >250° C., PMR (δppm, DMSO-$d_6$): 7.12 (1H,s), 7.23 (1H,d), 7.49–7.55 (2H,m), 7.86 (1H,d), 8.23–8.28 (2H,m), 11.90 (1H,br).

Example 17
Synthesis of sodium 4-[[7-chloro-2,4 (1H,3H)-quinazolinedion-3-yl]sulfonyl]benzoate (Compound 17)

50 mg (0.13 mmol) of the compound 6 was suspended in 10 ml of water, 130 μl (0.13 mmol) of a 1N sodium hydroxide aqueous solution was added dropwise, and the mixture was vigorously agitated. When becoming transparent, the reaction solution was freeze dried to obtain (quantitatively) 53 mg of the above-identified compound as a colorless amorphous powder. Melting point; >250° C., PMR (δppm, DMSO-$d_6$): 6.91–6.97 (2H,m), 7.51 (1H,t), 7.58 (1H,d), 7.72 (1H,d), 7.94 (1H,d), 7.99 (1H,s).

Example 18
Synthesis of sodium 3-[[7-chloro-2,4(1H,3H)-quinazolinedion-3-yl]sulfonyl]benzoate (Compound 18)

50 mg (0.13 mnol) of the compound 15 was treated by the same method as used in Example 17 to obtain (quantitatively) 54 mg of the above-identified compound as a colorless amorphous powder. Melting point: >230° C., PMR (δppm, DMSO-$d_6$): 7.10 (1H,s), 7.11 (1H,d), 7.60 (1H,t), 7.81 (1H,d), 8.12 (1H,d), 8.21 (1H,d), 8.61 (1H,s).

Example 19
Synthesis of 7-chloro-3-(4-methoxycarbonylbenzenesulfonyl)-2,4(1H,3H)-quinazolinedione (Compound 19)

1.12 g (4.65 mmol) of 4-methoxycarbonylbenzenesulfonylisocyanate and 798 mg (4.65 mmol) of 2-amino-4-chlorobenzoic acid were treated in the same way as in Example 1 to obtain 1.08 g of the above-identified compound (yield 58.9%). Properties: colorless crystal, Melting point: >230° C., PMR (δppm, DMSO-$d_6$): 3.91 (3H,s), 7.13 (1H,s), 7.23 (1H,d), 7.86 (1H,d), 8.20 (2H,d), 8.29 (2H,d), 11.80 (1H,br).

Example 20
Synthesis of 3-(4-chlorobenzenesulfonyl)-7,8-dimethyl-2,4 (1H,3H)-quinazolinedione (Compound 20)

365 mg (1.68 mmol) of 4-chlorobenzenesulfonylisocyanate and 230 mg (1.40 mmol) of 2-amino-3,4-dimethylbenzoic acid were treated in the same way as in Example 1 to obtain 272 mg of the above-identified compound (yield 53.6%). Properties: colorless crystal, Melting point; 241°–245° C., PMR (δppm, DMSO-$d_6$): 2.21 (3H,s), 2.32 (3H,s), 7.06 (1H,d), 7.63 (1H,d), 7.75 (2H,d), 8.18 (2H,d), 10.64 (1H,br).

Example 21
Synthesis of 3-(4-chlorobenzenesulfonyl)-6,7-dimethyl-2,4 (1H,3H)-quinazolinedione (Compound 21)

365 mg (1.68 mmol) of 4-chlorobenzenesulfonylisocyanate and 230 mg (1.40 mmol) of 2-amino-4,5-dimethylbenzoic acid were treated in the same way as in Example 1 to obtain 80 mg of the above-identified compound (yield 15.7%). Properties: colorless crystal, Melting point: 221°–222° C., PMR (δppm, DMSO-$d_6$): 2.23 (3H,s), 2.27 (3H,s), 6.89 (1H,s), 7.60 (1H,s), 7.75 (2H,d), 8.15 (2H,d), 11.40 (1H,br).

Example 22
Synthesis of 3-(4-chlorobenzenesulfonyl)-6,7-dimethoxy-2, 4(1H,3H)-quinazolinedione (Compound 22)

2.36 g (10.8 mmol) of 4-chlorobenzenesulfonylisocyanate and 1.94 g (9.84 mmol) of 2-amino-4,5-dimethoxybenzoic acid were treated in the same way as in Example 1 to obtain 2.86 g of the above-identified compound (yield 73.3%). Properties: colorless crystal, Melting point: >250° C., PMR (δppm, DMSO-$d_6$): 3.79 (3H,s), 3.84 (3H,s), 6.62 (1H,s), 7.22 (1H,s), 7.74 (2H,d), 8.15 (2H,d), 11.36 (1H,br).

Example 23
Synthesis of 3-(4-chlorobenzenesulfonyl)-2,4(1H,3H)-quinazolinedione (Compound 23)

3.10 g (14.3 mmol) of 4-chlorobenzenesulfonylisocyanate and 2.00 g (14.4 mmol) of 2-aminobenzoic acid were treated in the same way as in Example 1 to obtain 4.60 g of the above-identified compound (yield 94.4%). Properties: colorless crystal, Melting point: 214°–215° C., PMR (δppm, DMSO-$d_6$): 7.10 (1H,d), 7.20 (1H,t), 7.66 (2H,d), 7.70 (2H,d), 7.84 (1H,d), 7.15 (2H,d).

Example 24
Synthesis of 3-(4-chlorobenzenesulfonyl)-7-nitro-2,4(1H,3H)-quinazolinedione (Compound 24)

2.90 g (13.3 mmol) of 4-chlorobenzenesulfonylisocyanate and 2.21 g (14.1 mmol) of 2-amino-4-nitrobenzoic acid were treated in the same way as in Example 1 to obtain 7.02 g of the above-identified compound (yield 57.9%). Properties: colorless crystal, Melting point: 258°–260° C., PMR (δppm, DMSO-$d_6$): 7.10 (1H,s), 7.77 (2H,d), 7.92 (1H,d), 8.10 (1H,d), 8.19 (2H,d).

Example 25
Synthesis of 1-t-butoxycarbonylmethyl-7-chloro-3-(4-chlorobenzenesulfonyl)-2,4(1H,3H)-quinazolinedione (Compound 25)

Into 10 ml of dimethylformamide was dissolved 1.00 g (2.70 mmol) of the compound 1. Under ice cooling, 129 mg of sodium hydride (60%, in oil, 3.23 mol) was added and the mixture was stirred at room temperature for 30 minutes. Into the reaction solution was added drop-wise t-butyl bromacetate (478 μl, 3.24 mmol), then the mixture was stirred for one hour. Next, the same amount of sodium hydride (60%, in oil) and the same amount of t-butyl bromacetate were added and the mixture stirred for a further one hour. Ice water was poured into the reaction solution, extraction was performed by ethyl acetate, then the organic layer was washed by water and saturated saline, then was concentrated and dried under reduced pressure to obtain a crude product which was then purified by silica gel column chromatography (ethyl acetate/n-hexane=⅓) to obtain 545 mg of the above-identified compound (yield 41.6%). Properties: colorless crystal, Melting point: 188°–190° C., PMR (δppm, CDCl$_3$): 1.44 (9H,s), 4.65 (2H,s), 6.90 (1H,s), 7.22 (1H,d), 7.55 (2H,d), 8.06 (1H,d), 8.28 (2H,d).

Example 26
Synthesis of 1-allyloxycarbonylmethyl-3-(4-chlorobenzenesulfonyl)-2,4(1H,3H)-quinazolinedione (Compound 26)

500 mg of the compound 23 (1.49 mmol) and 208 μl of allyl chloroacetate (1.79 mmol) were treated in the same way as in Example 25 to obtain 343 mg of the above-identified compound (53.3%). Properties: colorless crystal, Melting point: 164°–166° C., PMR (δppm, CDCl$_3$): 4.65 (2H,d), 4.82 (2H,s), 5.25 (1H,d), 5.30 (1H,d), 5.80–5.90 (1H,m), 6.92 (1H,d), 7.27 (1H,d), 7.59 (2H,d), 8.14 (1H,d), 8.30 (2H,d).

Example 21
Synthesis of 7-chloro-3-(4-chlorobenzenesulfonyl)-1-methyl-2,4(1H,3H)-quinazolinedione (Compound 27)

500 mg of the compound 1(1.35 mmol) and 101 μl of methyl iodide (1.62 mmol) were treated in the same way as in Example 25 to obtain 308 mg of the above-identified compound (yield 59.2%). Properties: colorless crystal, Melting point: 205°–208° C., PMR (δppm, CDCl$_3$): 3.49 (3H,s), 7.14 (1H,s), 7.23 (1H,d), 7.56 (2H,d), 8.05 (1H,d), 8.30 (2H,d).

Example 28
Synthesis of 1-allyl-7-chloro-3-(4-chlorobenzenesulfonyl)-2,4(1H,3H)-quinazolinedione (Compound 28)

500 mg of the compound 1 (1.35 mmol) and 77 μl of allyl bromide (1.62 mmol) were treated in the same way as in Example 25 to obtain 249 mg of the above-identified compound (yield 45.0%). Properties: colorless crystal, Melting point: 161°–163° C., PMR (δppm, CDCl$_3$); 4.62 (3H,s), 5.26 (1H,d), 5.32 (1H,d), 5.81–5.90 (1H,m), 7.11 (1H,s), 7.21 (1H,d), 7.56 (2H,d), 8.04 (1H,d), 8.30 (2H,d).

Example 29
Synthesis of 1-carboxymethyl-7-chloro-3-(4-chlorobenzenesulfonyl)-2,4(1H,3H)-quinazolinedione (Compound 29)

Into 5 ml of dichloromethane was dissolved 479 mg (0.99 mmol) of the compound 25. 10 ml of trifluoroacetic acid (TFA) was added, then the mixture was stirred at room temperature for 3.5 hours. The reaction solution was concentrated to obtain a residue which was then washed by diethyl ether to obtain 420 mg of the above-identified compound (quantitatively). Properties: colorless crystal, Melting point: 194°–195° C., PMR (δppm, DMSO-$d_6$):4.75 (2 H,s), 7.36 (1H,d), 7.56 (1H,s), 7.78 (2H,d), 7. 98 (1H,d), 8.18 (2H,d).

Example 30
Synthesis of 3-benzenesulfonyl-2,4(1H,3H)-quinazolinedione (Compound 30)

3.00 g (16.4 mmol) of benzenesulfonylisocyanate and 2.04 g (14.9 mmol) of 2-aminobenzoic acid were treated in the same way as in Example 1 to obtain 3.26 g of the above-identified compound (yield 72.4%). Properties: colorless crystal, Melting point: 211°–213° C., PMR (δppm, DMSO-$d_6$): 7.13 (1H,d), 7.20 (1H,t), 7.61–7.70 (3 H,m), 7.78 (1H,t), 7.87 (1H,d), 8.17 (2H,d), 11.51 (1H,br).

Example 31
Synthesis of 3-(4-chlorobenzenesulfonyl)-7-fluoro-2,4(1H,3H)-quinazolinedione (Compound 31)

2.31 g (10.6 mmol) of 4-chlorobenzenesulfonylisocyanate and 1.50 g (9.67 mmol) of 2-amino-4-fluorobenzoic acid were treated in the same way as in Example 1 to obtain 2.87 g of the above-identified compound (yield 83.7%). Properties: colorless crystal, Melting point: >200° C., PMR (δppm, DMSO-$d_6$): 6.86 (1H,d), 7.04 (1H,t), 7.76 (2H,d), 7.93 (1H,dd), 8.17 (2H,d), 11.65 (1H,br).

Example 32
Synthesis of [7-chloro-3-(4-benzenesulfonyl)-2,4(1H,3H)-quinazolinedione-1-yl]acetic acid pyrrxolidinamide (Compound 32)

In 15 ml of dichloromethane was suspended 197 mg (0.46 mmol) of the compound 29. 46 μl (0.55 mmol) of pyrrolidine and 106 mg (0.55 mmol) of 1-(3-dimethylaminopropyl)-3-ethylcarbodiimide hydrochloride were added, then the mixture was stirred at room temperature for 20 minutes. The reaction solution was washed with water and saturated saline, then dried over anhydrous magnesium sulfate and concentrated to dryness under reduced pressure to obtain a crude product. Next, the crude product thus obtained was purified by silica gel column chromatography (0.5–1% methanol/dichloromethane) to obtain 75 mg of the above-identified compound (yield 33.8%). Properties: colorless crystal, Melting point: 212°–214° C., PMR (δppm, CDCl$_3$): 1.87–2.16 (4H,m), 3.49 (2H,t), 3.56 (2H,t), 4.72 (2H,s), 6.96 (1H,s), 7.19 (1H,d), 7.55 (2H,d), 8.04 (1H,d), 8.27 (2H,d).

Example 33
Synthesis of-3-(4-chlorobenzenesulfonyl)-6-fluoro-2,4(1H,3H)-quinazolinedione (Compound 33)

2.31 g (10.6 mmol) of 4-chlorobenzenesulfonylisocyanate and 1.50 g (9.67 mmol) of 2-amino-5-fluorobenzoic acid were treated in the same way as in Example 1 to obtain 1.04 g of the above-identified compound (yield 30.3%). Properties: colorless crystal, Melting point: >200° C., PMR (δppm, DMSO-$d_6$): 7.16 (1H,dd), 7.52–7.61 (2H,m), 7.75 (2H,d), 8.17 (2H,d), 11.59 (1H,br).

Example 34

Synthesis of 6-chloro-3-(4-chlorobenzenesulfonyl)-2,4(1H,3H)-quinazolinedione (Compound 34)

630 mg (2.90 mmol) of 4-chlorobenzenesulfonylisocyanate and 500 mg (2.92 mmol) of 2-amino-5-chlorobenzoic acid were treated in the same way as in Example 1 to obtain 520 mg of the above-identified compound (yield 47.9%). Properties; colorless crystal, Melting point: 223°–225° C., PMR (δppm, DMSO-$d_6$): 7.11 (1H,d), 7.69 (1H,q), 7.78 (3H,m), 8.15 (2H,d), 11.67 (1H,s).

Example 35

Synthesis -of 3-(4chlorobenzenesulfonyl)-2,4(1H,3H)-benzo[g]quinazolinedione (Compound 35)

1.10 g (5.06 mmol) of 4-chlorobenzenesulfonylisocyanate and 1.00 g (5.35 mmol) of 3-amino-2-naphthalic acid were treated in the same way as in Example 1 to obtain 1.60 g of the above-identified compound (yield 77.4%). Properties: colorless crystal, Melting point: 243°–246° C., PMR (δppm, DMSO-$d_6$): 7.47 (2H,m), 7.62 (1H,t), 7.78 (2H,d), 7.90 (1H,d), 8.09 (1H,d), 8.19 (2H,d), 8.62 (1H,s), 11.62 (1H,s).

Example 36

Synthesis of 7-chloro-3-(8-quinolinesulfonyl)-2,4(1H,3H)-quinazolinedione (Compound 36)

Following Synthesis Method (B), 200 mg (0.96 mmol) of 8-quinolinesulfonamide and 190 mg (1.25 mmol) of DBU were dissolved in 10 ml of THF, 320 mg (1.05 mmol) of methyl 4-chloro-2-phenoxycarbonylaminobenzoate was added, and the mixture was stirred at room temperature for 8 hours. The resultant crystal was obtained by filtration to obtain 390 mg of N-(5-chloro-2-methoxycarbonyl)-N'-(8-quinolyl)sulfonylurea (yield 96.4%). The resultant urea derivative (380 mg, 0.90 mmol) was dissolved in a mixture of 1N-sodium hydroxide aqueous solution (8 ml) and methanol (4 ml) and reacted at 60° C. for 30 minutes. The reaction solution was adjusted to pH3, the resultant crystal was obtained by filtration, and the corresponding carboxylate was obtained (280 mg, yield 76.7%). The resultant carboxylate (100 mg, 0.25 mmol) was suspended in a mixture of THF (10 ml) and dimethylformamide (2 ml), was ice-cooled and added with 100 mg (0.62 mmol) of CDI, then was agitated for 30 minutes. The solvent was distilled off under reduced pressure, then water was added, then the resultant crystal was washed by methanol to obtain 80 mg of the above-identified compound (84.0%). Properties: colorless crystal, Melting point: 284°–286° C., PMR (δppm, DMSO-$d_6$): 7.07 (1H,s), 7.21 (1H,d), 7.60 (1H,m), 7.83 (2H,m), 8.37 (1H,d), 8.52 (2H,d), 8.65 (1H,d), 11.57 (1H,s).

Example 37

Synthesis of 7-chloro-3-(4-toluenesulfonyl)-2,4(1H,3H)-quinazolinedione (Compound 37)

Following Synthesis Method (B), in 30 ml of anhydrous THF was dissolved 541 mg (1.77 mmol) of methyl 4-chloro-2-phenoxycarbonylaminobenzoate. To this were added 332 mg (1.94 mmol) of 4-toluenesulfonamide and 317 μl (2.12 mmol) of DBU. The mixture was then stirred at room temperature for 2 hours and 30 minutes. The reaction solution was diluted by water, then extraction was performed by ethyl acetate, the organic layer was washed by water and then saturated saline, then the result was concentrated and dried under reduced pressure to obtain 648 mg of a crude product of a sulfonylurea. The crude product thus obtained was dissolved in 3 ml of THF, then 4 ml of 1N-sodium hydroxide was added under ice cooling and the result was agitated for 5 hours. The reaction solution was diluted by water, then adjusted to pH 2 to 3 by 1N-hydrochloric acid, then extraction was performed by ethyl acetate, the organic layer was washed with water and then saturated saline, then the result was concentrated and dried under reduced pressure to obtain a crude product of a carboxylate. The crude product thus obtained was dissolved in 10 ml of anhydrous THF, then 286 mg (1.76 mmol) of CDI was added under ice cooling and the result was stirred for 30 minutes. The reaction solution was concentrated under reduced pressure, then extraction was performed by ethyl acetate/THF. The organic layer was washed by water, then saturated saline, then was concentrated and dried under reduced pressure to obtain a crude product. The resultant crude product was washed by ethyl acetate and acetone to obtain 150 mg of the above-identified compound (yield 24.2%). Properties: colorless crystal, Melting point: >200° C., PMR (δppm, DMSO-$d_6$): 2.43 (3H,s), 7.11 (1H,s), 7.20 (1H,d), 7.48 (2H,d), 7.85 (1H,d), 8.04 (2H,d), 11.33 (1H,br).

Example 38

Synthesis of [7-chloro-3-(4-chlorobenzenesulfonyl)-2,4(1H,3H)-quinazolinedion-1-yl]-N-phenylacetamide (Compound 38)

500 mg (1.16 mmol) of the compound 29 was dissolved in 15 ml of anhydrous THF, 246 mg (1.28 mmol) of 1-(3-dimethylaminopropyl)-3-ethyl carbodiimide hydrochloride and 119 mg (1.28 mmol) of aniline were added, and the result was stirred for 3 hours. Water was added to the reaction solution and the resultant crystals were obtained by filtration and washed by ethyl acetate to obtain 580 mg of the above-identified compound (yield 99.2%). Properties: colorless crystal, Melting point: 217°–218° C., PMR (δppm, DMSO-$d_6$): 4.86 (2H,s), 7.07 (1H,t), 7.30–7.38 (3H,m), 7.55 (2H,d), 7.60 (1H,s), 7.78 (2H,d), 7.99 (1H,s), 8.20 (2H,d), 10.30 (1H,s).

Example 39

Synthesis of [7-chloro-3-(4-chlorobenzenesulfonyl)-2,4(1H,3H)-quinazolinedion-1-yl]-N-(4-hydroxyphenyl)acetamide (Compound 39)

The same method as in Example 38 was used to obtain from 212 mg (0.49 mmol) of the compound 29 and 54 mg (0.49 mmol) of 4-hydroxyaniline 148 mg of the above-identified compound (yield 58.0%). Properties: colorless crystal, Melting point: 216°–218° C., PMR (δppm, DMSO-$d_6$): 4.8 (2H,s), 6.69 (2H,d), 7.30 (2H,d), 7.36 (1H,d), 7.55 (1H,s), 7.78 (2H,d), 7.99 (1H,d), 8.20 (2H,d), 9.20 (1H,s), 10.00 (1H,s).

Example 40

Synthesis of [7-chloro-3-(4-chlorobenzenesulfonyl)-2,4(1H,3H)-quinazolinedion-1-yl]-N-(3-hydroxyphenyl)acetamide (Compound 40)

The same method as in Example 38 was used to obtain from 212 mg (0.49 mmol) of the compound 29 and 54 mg (0.49 mmol) of 3-hydroxyaniline 223 mg of the above-identified compound (yield 87.5%). Properties: colorless crystal, Melting point: 215°–217° C., PMR (δppm, DMSO-$d_6$): 4.83 (2H,s), 6.47 (1H,d), 6.93 (1H,d), 7.05–7.10 (2H, m), 7.35 (1H,s), 7.57 (1H,s), 7.78 (2H,d), 7.99 (1H,d), 8.20 (2H,d), 9.33 (1H,s), 10.12 (1H,s).

Example 41
Synthesis of [7-chloro-3-(4-chlorobenzenesulfonyl)-2,4(1H,3H)-quinazolinedion-1-yl]-N-(2-hydroxyphenyl)acetamide (Compound 41)

The same method as in Example 38 was used to obtain from 212 mg (0.49 mmol) of the compound 29 and 54 mg (0.49 mmol) of 2-hydroxyaniline 223 mg of the above-identified compound (yield 87.5%). Properties: colorless crystal, Melting point: 203°–205° C., PMR (δppm, DMSO-$d_6$): 4.97 (2H,s), 6.74 (1H,t), 6.88–6.94 (2H,m), 7.36 (1H,d), 7.53 (1H,s), 7.78 (2H,d), 8.10 (1H,d), 8.20 (2H,d), 9.59 (1H,s), 9.84 (1H,s).

Example 42
Synthesis of [7-chloro-3-4-chlorobenzenesulfonyl)-2,4(1H,3H)-quinazolinedion-1-yl]-N-(4-allyloxycarbonylphenyl) acetamide (Compound 42)

The same method as in Example 38 was used to obtain from 300 mg (0.70 mmol) of the compound 29 and 134 mg (0.49 mmol) of 4-aminobenzoic acid allylester 324 mg of the above-identified compound (yield 76.8%). Properties: colorless crystal, Melting point: 235°–238° C., PMR (δppm, DMSO-$d_6$): 3.65 (2H,s), 4.55 (2H,d), 4.85 (2H,s), 5.21 (2H,dd), 5.86–5.93 (1H,m), 7.22 (2H,d), 7.36 (1H,d), 7.49 (2H,d), 7.58 (1H,s), 7.77 (2H,d), 7.99 (1H,d), 8.20 (2H,d), 9.33 (1H,s), 10.26 (1H,s).

Example 43
Synthesis of [7-chloro-3-(4-chlorobenzenesulfonyl)-2,4(1H,3H)-quinazolinedion-1-yl]-N-(4-carboxyphenyl)-acetamide (Compound 43)

The same method as in Example 6 was used to obtain from 310 mg (0.52 mmol) of the compound 42 106 mg of the above-identified compound (yield 36.2%). Properties: colorless crystal, Melting point: 219°–221° C., PMR (δppm, DMSO-$d_6$): 3.54 (2H,s), 4.86 (2H,s), 7.20 (2H,d), 7.35 (1H,d), 7.48 (2H,d), 7.57 (1H,s), 7.77 (2H,d), 7.95 (1H,s), 7.99 (2H,d), 8.20 (2H,d), 10.24 (1H,s), 12.20 (1H,s).

Example 44
Synthesis of [7-chloro-3-(4-chlorobenzenesulfonyl)-2,4(1H,3H)-quinazolinedion-1-yl]-N-(4-morpholinomethylphenyl) acetamide (Compound 44)

The same method as in Example 38 was used to obtain from 155 mg (0.36 mmol) of the compound 29 and 69 mg (0.36 mmol) of 4-morpholinomethylaniline 150 mg of the above-identified compound (yield 69.0%). Properties: colorless crystal, Melting point: 226°–227° C., PMR (δppm, DMSO-$d_6$): 2.33 (4H,t), 3.56 (4H,t), 4.85 (2H,s), 7.24 (2H,d), 7.37 (1H,d), 7.50 (2H,d), 7.59 (1H,s), 7.79 (2H,d), 7.99 (1H,d), 8.20 (2H,d), 10.29 (1H,s).

Example 45
Synthesis of [7-chloro-3-(4-chlorobenzenesulfonyl)-2,4(1H,3H)-quinazolinedion-1-yl]-N-(4-t-butoxycarbonylaminomethylphenyl)acetamide (Compound 45)

The same method as in Example 38 was used to obtain from 300 mg (0.70 mmol) of the compound 29 and 155 mg (0.70 mmol) of 4-t-butoxycarbonylaminomethylaniline 256 mg of the above-identified compound (yield 57.7%). Properties: colorless crystal, Melting point: 229°–232° C., PMR (δppm, DMSO-$d_6$); 1.39 (9H,s), 4.08 (2H,d), 4.85 (2H,d), 7.18 (2H,d), 7.37 (1H,d), 7.48 (2H,d), 7.60 (1H,s), 7.78 (2H,d), 7.99 (1H,d), 8.20 (2H,d), 10.27 (1H,s).

Example 46
Synthesis of [7-chloro-3-(4-chlorobenzenesulfonyl)-2,4(1H,3H)-quinazolinedion-1-yl]-N-(4-aminomethylphenyl) acetamide (Compound 46)

The same method as in Example 29 was used to obtain from 302 mg (0.47 mmol) of the compound 45 207 mg of the above-identified compound (yield 81.4%). Properties: colorless crystal, Melting point: 210°–211° C., PMR (δppm, DMSO-$d_6$): 4.00 (2H,d), 4.88 (2H,s), 7.36–7.42 (3H,m), 7.60–7.61 (3H,m), 7.78 (2H,s), 7.99 (1H,d), 8.19–8.28 (4H,m), 10.48 (1H,s).

Example 47
Synthesis of [7-chloro-3-(4-chlorobenzenesulfonyl)-2,4(1H,3H)-quinazolinedion-1-yl]-N-4-((3-t-butoxycarbonyl)-2-S-(t-butoxycarbonylamino)propionyl)-aminomethyl phenyl) acetamide (Compound 47)

The same method as in Example 38 was used to obtain from 322 mg (0.75 mmol) of the compound 29 and 304 mg (0.75 mmol) of β-O-t-butyl-N-t-butoxycarbonyl-L-aspartic acid 4-aminobenzylamide 504 mg of the above-identified compound (yield 62.6%). Properties: colorless crystal, Melting point: 213°–214° C., PMR (δppm, DMSO-$d_6$): 1.39 (18H,s), 2.41–2.68 (2H,m), 4.22–4.33 (3H,m), 4.85 (2H,m), 7.02 (1H,d), 7.18 (2H,d), 7.35 (1H,d), 7.47 (2H,d), 7.58 (1H,s), 7.99 (1H,d), 8.20 (2H,d), 8.26 (2H,t), 10.26 (1H,s).

Example 48
Synthesis of [7-chloro-3-(4-chlorobenzenesulfonyl)-2,4(1H,3H)-quinazolinedion-1-yl]-N-(4-α-L-aspartylaminomethylphenyl)acetamide (Compound 48)

The same method as in Example 29 was used to obtain from 477 mg (0.59 mmol) of the compound 47,380 mg of the above-identified compound (yield 99.3%). Properties: colorless crystal, Melting point: 211°–214° C., PMR (δppm, DMSO-$d_6$): 2.80–2.84 (2H,m), 4.05 (1H), 4.28–4.34 (2H, m), 4.86 (2H,s), 7.23 (2H,d), 7.36 (1H,d), 7.52 (2H,d), 7.58 (1H,s), 7.77 (2H,d), 7.99 (1H,d), 8.19–8.28 (4H,m), 8.87 (1H,t), 10.35 (1H,s).

Example 49
Synthesis of [7-chloro-3-(4-chlorobenzenesulfonyl)-2,4(1H,3H)-quinazolinedion-1-yl]-N-(4-((3-t-butoxycarbonyl)-3-S-(t-butoxycarbonylamino)propionyl)aminomethylphenyl) acetamide (Compound 49)

The same method as in Example 38 was used to obtain from 322 mg (0.75 mmol) of the compound 29 and 304 mg (0.75 mmol) of α-O-t-butyl-N-t-butoxycarbonyl-L-aspartic acid 4-aminobenzylamide 519 mg of the above-identified compound (yield 86.0%). Properties: colorless crystal, Melting point: 220°–222° C., PMR (δppm, DMSO-$d_6$): 1.39 (18H,s), 2.51–2.57 (2H,m), 4.19–4.30 (3H,m), 4.86 (2H,s), 6.83 (1H,d), 7.19 (2H,d), 7.34 (1H,d), 7.48 (2H,d), 7.55 (1H,s), 7.76 (2H,d), 7.99 (1H,d), 8.20 (2H,d), 8.28 (2H,t), 10.22 (1H,s).

Example 50
Synthesis of [7-chloro-3-(4-chlorobenzenesulfonyl)-2,4(1H,3H)-quinazolinedion-1-yl]-N-(4-β-L-aspartylaminomethylphenyl)acetamide (Compound 50)

The same method as in Example 29 was used to obtain from 400 mg (0.50 mmol) of the compound 49 322 mg of the above-identified compound (yield 100%). Properties: colorless crystal, Melting point: 201°–204° C., PMR (δppm, DMSO-$d_6$): 2.77–2.80 (2H,m), 4.17–4.28 (3H,m), 4.85 (2H, s), 7.22 (2H,d), 7.36 (1H,d), 7.50 (2H,d), 7.57 (1H,s), 7.78 (2H,d), 7.99 (1H,d), 8.10–8.31 (4H,m), 8.65 (1H,t), 10.29 (1H,s).

Example 51
Synthesis of [7-chloro-3-(4-chlorobenzenesulfonyl)-2,4(1H,3H)-quinazolinedion-1-yl]-N-3-((3-t-butoxycarbonyl)-3-S-

(t-butoxycarbonylamino)propionyl)aminomethylphenyl) acetamide (Compound 51)

The same method as in Example 38 was used to obtain from 137 mg (0.32 mmol) of the compound 29 and 129 mg (0.32 mmol) of α-O-t-butyl-N-t-butoxycarbonyl-L-aspartic acid 3-aminobenzylamide 188 mg of the above-identified compound (yield 73.0%). Properties: amorphous, PMR (δppm, DMSO-$d_6$): 1.39 (18H,s), 4.22–4.40 (3H,m), 4.86 (2H,s), 6.84 (1H,d), 6.98 (1H,d), 7.23 (1H,t), 7.35 (1H,d), 7.43 (1H,d), 7.48 (1H,s), 7.56 (1H,s), 7.76 (2H,d), 7.99 (1H,d), 8.19–8.35 (3H,m), 10.26 (1H,s).

Example 52
Synthesis of [7-chloro-3-(4-chlorobenzenesulfonyl)-2,4(1H, 3H)-quinazolinedion-1-yl]-N-(3-β-L-aspartylaminomethylphenyl)acetamide (Compound 52)

The same method as in Example 29 was used to obtain from 100 mg (0.124 mmol) of the compound 51 80 mg of the above-identified compound (yield 100%). Properties; colorless crystal, Melting point: >200° C. (decomposition), PMR (δppm, DMSO-$d_6$): 2.77–2.81 (2H,m), 4.14–4.28 (3H, m), 4.86 (2H,s), 7.00 (1H,d), 7.27 (1H,t), 7.32–7.40 (2H,m), 7.56 (2H,s), 7.78 (2H,d), 7.99 (1H,d), 8.10–8.30 (4H,m), 10.32 (1H,s).

Example 53
Synthesis of [7-chloro-3-(4-chlorobenzenesulfonyl)-2,4(1H, 3H)-quinazolinedion-1-yl]-N-(3-pyridyl)acetamide (Compound 53)

The same method as in Example 38 was used to obtain from 300 mg (0.70 mmol) of the compound 29 and 66 mg (0.70 mmol) of 3-aminopyridine 250 mg of the above-identified compound (yield 70.7%). Properties: colorless crystal, Melting point: 216°–220° C., PMR (δppm, DMSO-$d_6$): 4.89 (2H,s), 7.35 (2H,t), 7.62 (1H,s), 7.77 (2H,d), 8.00 (2H,d), 8.20 (2H,d), 8.29 (1H,d), 8.72 (1H,s), 10.52 (1H,s).

Example 54
Synthesis of [7-chloro-3-(4-chlorobenzenesulfonyl)-2,4(1H, 3H)-quinazolinedion-1-yl]-N-(4-pyridyl)acetamide (Compound 54)

The same method as in Example 38 was used to obtain from 300 mg (0.70 mmol) of the compound 29 and 66 mg (0.70 mmol) of 4-aminopyridine 26 mg of the above-identified compound (yield 7.4%). Properties: colorless crystal, Melting point: >180° C. (decomposition), PMR (δppm, DMSO-$d_6$): 4.88 (2H,s), 7.38 (1H,d), 7.53 (2H,d), 7.65 (1H,s), 7.78 (2H,d), 7.99 (1H,d), 8.18 (2H,d), 8.45 (2H,d), 10.68 (1H,s).

Example 55
Synthesis of [7-chloro-3-(4-chlorobenzenesulfonyl)-2,4(1H, 3H)-quinazolinedion-1-yl]-N-(2-pyridyl)acetamide (Compound 55)

The same method as in Example 38 was used to obtain from 300 mg (0.70 mmol) of the compound 29 and 66 mg (0.70 mmol) of 2-aminopyridine 150 mg of the above-identified compound (yield 42.4%). Properties: colorless crystal, Melting point: >180° C. (decomposition), PMR (δppm, DMSO-$d_6$): 4.94 (2H,s), 7.11 (2H,t), 7.35 (1H,d), 7.58 (1H,s), 7.76–8.33 (8H,m), 10.81 (1H,s).

Example 56
Synthesis of 3-{[7-chloro-3-(4-chlorobenzenesulfonyl)-2,4 (1H,3H)-quinazolinedion-1-yl]acetylamino}-N-ethylpyridinium iodide (Compound 56)

In 60 ml of acetonitrile was suspended 1.50 g (2.97 mmol) of the compound 53, then 2.37 ml(29.6 mmol) of ethyl iodide was added and the mixture was heated and refluxed for 13 hours. The reaction solution was allowed to cool to room temperature, then the resultant crystal was obtained by filtration and washed by acetone to obtain 1.5 g of the above-identified compound (yield 76.4%). Properties: light yellow crystal, Melting point: 171°–172° C. (decomposition), PMR (δppm, DMSO-$d_6$): 1.53 (3H,t), 4.66 (2H,q), 4.98 (2H,s), 7.41 (1H,d), 7.67 (1H,s), 7.82 (2H,d), 8.01 (1H,d), 8.13 (1H,dd), 8.19 (2H,d), 8.39 (1H,d), 8.85 (1H,d), 9.43 (1H,s), 11.42 (1H,s).

Example 57
Synthesis of 3-{[7-chloro-3-(4-chlorobenzenesulfonyl)-2,4 (1H,3H)-quinazolinedion-1-yl]acetylamino}-N-methylpyridinium iodide (Compound 57)

The same method as in Example 56 was used to obtain from 200 mg (0.396 mmol) of the compound 53 169 mg of the above-identified compound (yield 65.9%). Properties: light yellow crystal, Melting point: 177°–178° C. (decomposition), PMR (δppm, DMSO-$d_6$): 4.37 (3H,s), 4.98 (2H,s), 7.41 (1H,d), 7.67 (1H,s), 7.82 (2H,d), 8.01 (1H,d), 8.10 (1H,dd), 8.19 (2H,d), 8.38 (1H,d), 8.73 (1H,d), 9.35 (1H,s), 11.38 (1H,s).

Example 58
Synthesis of 4-{[7-chloro-3-(4-chlorobenzenesulfonyl)-2,4 (1H,3H)-quinazolinedion-1-yl]acetylamino}-N-methylpyridinium iodide (Compound 58)

The same method as in Example 56 was used to obtain from 46 mg (0.091 mmol) of the compound 54 29 mg of the above-identified compound (yield 49.2%). Properties: light yellow crystal, Melting point: 178°–181° C. (decomposition), PMR (δppm, DMSO-$d_6$): 4.20 (3H,s), 4.97 (2H,s), 7.41 (1H,d), 7.71 (1H,s), 7.81 (2H,d), 8.00–8.04 (3H,m), 8.18 (2H,d), 8.73 (2H,d), 11.83 (1H,br).

Example 59
Synthesis of 1-benzyl-7-chloro-3-(4-chlorobenzenesulfonyl)-2,4(1H,3H)-quinazolinedione (Compound 59)

In 15 ml of dimethylformamide was dissolved 1.00 g (2.70 mmol) of the compound 1. Under ice cooling, 140 mg of sodium hydride (60%, in oil, 3.23 mol) was added and the mixture was stirred at room temperature for 30 minutes. To the reaction solution was further added dropwise benzylbromide (385 μl, 3.24 mmol) after which the mixture was stirred at room temperature overnight. An excess amount of ice water was poured into the reaction solution, the precipitated crystal was obtained by filtration and washed by a small amount of water and diethyl ether, then was concentrated under reduced pressure to obtain 777 mg of the above-identified compound (yield 62.4%). Properties; colorless crystal, Melting point: 242°–244° C., PMR (δppm, CDCl$_3$): 5.21 (2H,s), 7.07 (1H,s), 7.17–7.37 (6H,m), 7.57 (2H,d), 8.04 (1H,d), 8.31 (2H,d)

Example 60
Synthesis of 7-chloro-3-(4-chlorobenzenesulfonyl)-1-(4-cyanobenzyl)-2,4(1H,3H)-quinazolinedione (Compound 60)

The same method as in Example 59 was used to obtain from 1.0 g (2.69 mmol) of the compound 1 and 540 mg (2.75 mmol) of 4-cyanobenzylbromide 460 mg of the above-identified compound (yield 34.9%). Properties: colorless crystal, Melting point: >200° C. (decomposition), PMR (δppm, DMSO-$d_6$): 5.33 (2H,s), 7.28 (1H,s), 7.33 (1H,d), 7.50 (2H,d), 7.79 (2H,d), 7.98 (2H,d).

Example 61
Synthesis of 7-chloro-3-(4-chlorobenzenesulfonyl)-1-(3-cyanobenzyl)-2,4(1H,3H)-quinazolinedione (Compound 61)

The same method as in Example 59 was used to obtain from 1.0 g (2.69 mmol) of the compound 1 and 540 mg (2.75 mmol) of 3-cyanobenzylbromide 420 mg of the above-identified compound (yield 32.0%). Properties: colorless crystal, Melting point: >200° C. (decomposition), PMR (δppm, DMSO-$d_6$): 5.29 (2H,s), 7.29 (1H,s), 7,32 (1H,d), 7.5–7.6 (1H,m), 7.6–7.8 (5H,m), 7.98 (1H,d), 8.20 (2H,d).

Example 62
Synthesis of 7-chloro-3-(4-chlorobenzenesulfonyl)-1-(2-cyanobenzyl)-2,4(1H,3H)-quinazolinedione (Compound 62)

The same method as in Example 59 was used to obtain from 1.0 g (2.69 mmol) of the compound 1 and 540 mg (2.75 mmol) of 2-cyanobenzylbromide 310 mg of the above-identified compound (yield 23.8%). Properties: colorless crystal, Melting point: >200° C. (decomposition), PMR (δppm, DMSO-$d_6$): 5.38 (2H,s), 7.3–7.4 (2H,m), 7.4–7.5 (2H,m), 7.5–7.7 (1H,m), 7.77 (2H,d), 7.84 (1H,d), 8.00 (1H,d), 8.17 (2H,d).

Example 63
Synthesis of 1-(4-allyloxycarbonyl-benzyl)-7-chloro-3-(4-chlorobenzenesulfonyl)-2,4(1H,3H)-quinazolinedione (Compound 63)

The same method as in Example 59 was used to obtain from 2.0 g (5.39 mmol) of the compound 1 and 1.6 g (6.27 mmol) of 4-bromomethylbenzoic acid allylester 1.32 g of the above-identified compound (yield 44.9%). Properties: colorless crystal, Melting point: 190°–191° C. (decomposition), PMR (δppm, DMSO-$d_6$): 4.78 (2H,d), 5.2–5.4 (4H,m), 5.9–6.1 (1H,m), 7.2–7.4 (4H,m), 7.7–8.0 (6H,m), 8.1–8.3 (2H,m).

Example 64
Synthesis of 1-(3-carboxybenzyl)-7-chloro-3-(4-chlorobenzenesulfonyl)-2,4(1H,3H)-quinazolinedione (Compound 64)

The same method as in Example 6 was used to obtain from 1.0 g (1.83 mmol) of the compound 63 750 mg of the above-identified compound (yield 80.9%). Properties: colorless crystal, Melting point: >250° C. (decomposition), PMR (δppm, DMSO-$d_6$): 5.16 (2H,s), 7.1–7.3 (4H,m), 7.64 (2H,d), 7.72 (2H,d), 7.83 (1H,d), 8.04 (2H,d), 12.8 (1H,s,br).

Example 65
Synthesis of 1-(3-allyloxycarbonyl-benzyl)-7-chloro-3-(4-chlorobenzenesulfonyl)-2,4(1H,3H)-quinazolinedione (Compound 65)

The same method as in Example 59 was used to obtain from 2.0 g (5.39 mmol) of the compound 1 and 1.6 g (6.27 mmol) of 3-bromomethylbenzoic acid allylester 1.85 g of the above-identified compound (yield 62.9%). Properties: colorless crystal, Melting point: >200° C. (decomposition), PMR (δppm, DMSO-$d_6$): 4.78 (2H,d), 5.2–5.4 (4H,m), 5.9–6.1 (1H,m), 7.2–7.4 (4H,m), 7.7–8.0 (6H,m), 8.1–8.3 (2H,m).

Example 66
Synthesis of 1-(3-carboxybenzyl)-7-chloro-3-(4-chlorobenzenesulfonyl)-2,4(1H,3H)-quinazolinedione (Compound 66)

The same method as in Example 6 was used to obtain from 1.5 g (2.75 mmol) of the compound 65 1.28 g of the above-identified compound (yield 92.0%). Properties: colorless crystal, Melting point: >250° C. (decomposition), PMR (δppm, DMSO-$d_6$): 5.30 (2H,s), 7.3–7.5 (4H,m), 7.7–7.9 (3H,m), 7.9–8.0 (2H,m), 8.19 (2H,d), 13.2 (1H,s,br).

Example 67
Synthesis of 7-chloro-3-(4-chlorobenzenesulfonyl)-1-(4-(3-pyridyl)aminocarbonylbenzyl)-2,4(1H,3H)-quinazolinedione (-Compound 67)

The same method as in Example 38 was used to obtain from 100 mg (0.2 mmol) of the compound 64 and 19 mg (0.2 mmol) of 3-aminopyridine 91 mg of the above-identified compound (yield 80.0%). Properties: colorless crystal, Melting point: >150° C. (decomposition), PMR (δppm, DMSO-$d_6$): 5.34 (2H,s), 7.2–7.5 (6H,m), 7.7–8.0 (5H,m), 8.1–8.3 (4H,m), 8.90 (1H,s), 10.41 (1H,s).

Example 68
Synthesis of 7-chloro-3-(4-chlorobenzenesulfonyl)-1-(3-(3-pyridyl)aminocarbonyl-benzyl)-2,4(1H,3H)-quinazolinedione (Compound 68)

The same method as in Example 38 was used to obtain from 100 mg (0.2 mmol) of the compound 66 and 19 mg (0.2 mmol) of 3-aminopyridine 96 mg of the above-identified compound (yield 85.0%). Properties: colorless crystal, Melting point: >150° C. (decomposition), PMR (δppm, DMSO-$d_6$): 5.33 (2H,s), 7.3–7.5 (6H,m), 7.7–8.0 (5H,m), 8.1–8.3 (4H,m), 8.90 (1H,s), 10.46 (1H,s).

Example 69
Synthesis of 4-(7-chloro-3-(4-chlorobenzenesulfonyl)-2,4(1H,3H)-quinazolinedion-1-yl)methylbenzoylglycine (Compound 69)

The same method as in Example 38 was used to obtain from 250 mg (0.5 mmol) of the compound 64 and 85 mg (0.2 mmol) of glycine-t-butyl ester 310 mg of the corresponding t-butyl ester derivative.

This derivative was treated by the same method as in Example 29 to obtain 230 mg of the above-identified compound (yield 82.0%). Properties: colorless crystal, Melting point: >170° C. (decomposition), PMR (δppm, DMSO-$d_6$): 3.89 (2H,d), 5.29 (2H,s), 7.2–7.4 (4H,m), 7.7–8.0 (5H,m), 8.20 (1H,d), 8.80 (1H,t), 11.95 (1H,s,br).

Example 70
Synthesis of 3-(7-chloro-3-(4-chlorobenzenesulfonyl)-2,4(1H,3H)-quinazolinedion-1-yl)methylbenzoylglycine (Compound 70)

The same method as in Example 38 was used to obtain from 250 mg (0.5 mmol) of the compound 66 and 85 mg (0.2 mmol) of glycine-t-butyl ester 310 mg of the corresponding t-butyl ester derivative.

This derivative was treated by the same method as in Example 29 to obtain 220 mg of the above-identified compound (yield 78.0%). Properties: colorless crystal, Melting point: >170° C. (decomposition), PMR (δppm, DMSO-$d_6$): 3.91 (2H,d), 5.28 (2H,s), 7.3–7.5 (4H,m), 7.7–8.0 (5H,m), 8.20 (2H,d), 8.83 (1H,t), 12.60 (1H,s,br).

Example 71
Synthesis of 7-chloro-3-(4-chlorobenzenesulfonyl)-1-(4-nitrobenzyl)-2,4(1H,3H)-quinazolinedione (Compound 71)

The same method as in Example 59 was used to obtain from 3.71 g (10 mmol) of the compound 1 and 2.38 g (11 mmol) of 4-nitrobenzylbromide 4.96 g of the above-identified compound (yield 98.0%). Properties: colorless crystal, Melting point: >235° C. (decomposition), PMR (δppm, DMSO-$d_6$): 5.39 (2H,s), 7.33–8.21 (11H,m).

Example 72
Synthesis of 1-(4-aminobenzyl)-7-chloro-3-(4-chlorobenzenesulfonyl)-2,4(1H,3H)-quinazolinedione (Compound 72)

1.0 g (1.98 mmol) of the compound 71 was dissolved in a mixed solution of THF (100 ml) and acetic acid (5 ml), 400 mg of platinum (IV) oxide was added, then the result was hydrolyzed. After six hours, the catalyst was filtered out and the solvent was distilled off under reduced pressure. The resultant residue was purified by silica gel column chromatography (methylene chloride:ethyl acetate=30:1) and the result crystallized by isopropyl ether to obtain 425 mg of the above-identified compound (yield 45.2%). Properties: colorless crystal, Melting point: 191°–192° C., PMR (δppm, CDCl$_3$): 3.08 (2H,br), 5.08 (2H,s), 6.62–8.33 (11H,m).

Example 73
Synthesis of 7-chloro-3-4-chlorobenzenesulfonyl)-1-(4-succinylaminobenzyl)-2,4(1H,3H)-quinazolinedione (Compound 73)

300 mg (0.63 mmol) of the compound 72 and 100 mg (1 mmol) of anhydrous succinic acid were dissolved in THF (10 ml). The resultant mixture was heated and refluxed for 2 hours. The reaction solution was distilled under reduced pressure and recrystallized from chloroform to obtain 253 mg of the above-identified compound (yield 69.7%). Properties: colorless crystal, Melting point: 175°–177° C., PMR (δppm, CDCl$_3$): 2.50 (4H,m), 5.18 (2H,s), 7.20–8.23 (11H, m), 9.94 (1H,s), 12.07 (1H,s).

Example 74
Synthesis of 7-chloro-3-(4-chlorobenzenesulfonyl)-1-(2-t-butoxycarbonylaminobenzyl)-2,4(1H,3H)-quinazolinedione (Compound 74)

The same method as in Example 59 was used to obtain from 1.05 g (2.83 mmol) of the compound 1 and 894 mg (3.12 mmol) of 2-t-butoxycarbonylaminobenzylbromide 1.08 mg of the above-identified compound (yield 66.3%). Properties: colorless crystal, Melting point: 176°–178° C., PMR (δppm, CDCl$_3$): 1.52 (9H,s), 5.20 (2H,s), 6.64 (1H,s), 6.96–8.31 (11H,m).

Example 75
Synthesis of 1-(2-aminobenzyl)-7-chloro-3-(4-chlorobenzenesulfonyl)-2,4(1H,3H)-quinazolinedione (Compound 75)

The same method as in Example 29 was used to obtain from 950 mg (1.65 mmol) of the compound 74,751 mg of the above-identified compound (yield 95.7%). Properties: colorless crystal, Melting point: 228°–230° C., PMR (δppm, DMSO-d$_6$): 4.96 (2H,s), 5.15 (2H,s), 6.44–8.22 (11H,m).

Example 76
Synthesis of 7-chloro-3-(4-chlorobenzenesulfonyl)-1-(2-succinylaminobenzyl)-2,4(1H,3H)-quinazolinedione (Compound 76)

The same method as in Example 73 was used to obtain from 100 mg (1.65 mmol) of the compound 75,94 mg of the above-identified compound (yield 77.7%). Properties: colorless crystal, Melting point: 148°–152° C., PMR (δppm, DMSO-d$_6$): 2.58 (4H,m), 5.08 (2H,s), 7.00–8.22 (11H,m), 9.77 (1H,s).

Example 77
Synthesis of [3-(3-allyloxycarbonylbenzenesulfonyl)-7-chloro-2,4(1H,3H)-quinazolinedion-1-yl]-N-(3-pyridyl)acetamide (Compound 77)

The compound 14 was used as the starting substance and the same method as in Example 25 was applied to obtain [3-(3-allyloxycarbonylbenzenesulfonyl)-7-chloro-2,4(1H,3H)-quinazolinedion-1-yl]acetic acid t-butyl ester then the same method as in Example 29 was used to obtain [3-(3-allyloxycarbonylbenzenesulfonyl)-7-chloro- 2,4(1H,3H)-quinazolinedion-1-yl]acetic acid.

Next, the same method as in Example 38 was used to obtain from 500 mg (1.04 mmol) of [3-(3-allyloxycarbonylbenzenesulfonyl)-7-chloro-2,4(1H,3H)-quinazolinedion-1-yl]acetic acid and 98 mg (1.04 mmol) of 3-aminopyridine 332 mg of the above-identified compound (yield 55.8%). Properties: colorless crystal, Melting point: >200° C. (decomposition), PMR (δppm, CDCl$_3$):4.83 (2H, d), 4.92 (2H,s), 5.30 (1H,d), 5.42 (1H,d), 5.95–6.03 (1H,m), 7.17 (1H,q), 7.23 (1H,d), 7.38 (1H,s), 7.69 (1H,t), 7.94 (1H,d), 8.02 (1H,d), 8.33 (1H,d), 8.51 (1H,d), 8.56 (1H,s), 8.83 (1H,s), 8.95 (1H,s).

Example 78
Synthesis of [3-(3-carboxybenzenesulfonyl)-7-chloro-2,4(1H,3H)-quinazolinedion-1-yl]-N-(3-pyridyl)acetamide (Compound 78)

The same method as in Example 6 was used to obtain from 286 mg (0.52 mmol) of the compound 77,230 mg of the above-identified compound (yield 86.7%). Properties: colorless crystal, Melting point: >200° C. (decomposition), PMR (δppm, DMSO-d$_6$):4.88 (2H,s), 7.38 (2H,d), 7.64 (1H,s), 7.86 (1H,t), 8.01 (2H,d), 8.31 (2H,t), 8.41 (1H,d), 8.72 (2H,s), 10.52 (1H,s), 13.4 (1H,br).

Example 79
Synthesis of 3-{[3-(3-allyloxycarbonylbenzenesulfonyl)-7-chloro-2,4(1H,3H)-quinazolinedion-1-yl]acetylamino}-N-ethylpyridinium iodide (Compound 79)

The same method as in Example 56 was used to obtain from 100 mg (0.19 mmol) of the compound 78,65 mg of the above-identified compound (yield 49.9%). Properties: colorless crystal, Melting point: >200° C. (decomposition), PMR (δppm, DMSO-d$_6$): 1.53 (3H,t), 4.66 (2H,q), 4.98 (2H,s), 7.41 (1H,d), 7.67 (1H,s), 7.87 (1H,t), 7.96 (1H,s), 8.02 (1H,d), 8.13 (1H,t), 8.33 (1H,d), 8.41 (1H,d), 8.71 (1H,s), 9.43 (1H,s), 11.41 (1H,s), 13.35 (1H,br).

Example 80
Synthesis of [7-chloro-3-( 4-chlorobenzenesulfonyl)-2,4(1H,3H)-quinazolinedion-1-yl]-N-benzylacetamide (Compound 80)

The same method as in Example 38 was used to obtain from 300 mg (0.70 mmol) of the compound 29 and 76 μl (0.70 mmol) of 3-aminopyridine 250 mg of the above-identified compound (yield 68.9%). Properties: colorless crystal, Melting point: 215°–216° C., PMR (8ppm, DMSO-d$_6$):4.30 (2H,d), 4.75 (2H,s), 7.15 (2H,d), 7.23–7.40 (5H,m), 7.81 (2H,d), 7.98 (1H,d), 8.21 (2H,d), 8.66 (1H,t).

Example 81
Synthesis of [7-chloro-3-(4-chlorobenzenesulfonyl)-2,4(1H,3H)-quinazolinedion-1-yl]-N-(4-picolyl)acetamide (Compound 81)

The same method as in Example 38 was used to obtain from 300 mg (0.70 mmol) of the compound 29 and 71 μl (0.70 mmol) of 4-aminomethylpyridine, 160 mg of the above-identified compound (yield 44.0%). Properties: colorless crystal, Melting point: >200° C. (decomposition), PMR (δppm, DMSO-d$_6$):4.31 (2H,d), 4.79 (2H,s), 7.16 (2H,d), 7.39 (1H,d), 7.45 (1H,s), 7.81 (2H,d), 7.98 (1H,d), 8.21 (2H,d), 8.46 (2H,d), 8.93 (1H,t)

Example 82
Synthesis of [7-chloro-3-(4-chlorobenzenesulfonyl)-2,4(1h,3H)-quinazolinedion-1-yl]-N-(5-indolyl)acetamide (Compound 82)

The same method as in Example 38 was used to obtain from 300 mg (0.70 mmol) of the compound 29 and 92 mg (0.70 mmol) of 5-aminoindole 257 mg of the above-identified compound (yield 67.6%). Properties: colorless crystal, Melting point: 222°–224° C., PMR (δppm, DMSO-$d_6$):4.86 (2H,s), 6.37 (1H,s), 7.16 (1H,d), 7.31–7.40 (3H,m), 7.59 (1H,s), 7.77–7.82 (3H,m), 8.00 (1H,d), 8.21 (2H,d), 10.04 (1H,s), 11.01 (1H,s).

Example 83

Synthesis of 3-{[7-chloro-3-(4-chlorobenzenesulfonyl)-2,4(1H,3H)-quinazolinedion-1-yl]acetylamino}-(N-t-butoxycarbonylmethylpyridinium) bromide (Compound 83)

The same method as in Example 56 was used to obtain from 100 mg (0.20 mmol) of the compound 53 and 58 μl (0.39 mmol) of t-butyl bromoacetate 113 mg of the above-identified compound (yield 81.5%). Properties: colorless crystal, Melting point: >200° C. (decomposition), PMR (δppm, DMSO-$d_6$):1.44 (9H,s), 4.97 (2H,s), 5.59 (2H,s), 7.39 (1H,d), 7.69 (1H,s), 7.80 (2H,d), 7.99 (1H,d), 8.18–8.20 (3H,m), 8.47 (1H,d), 8.77 (1H,d), 9.49 (1H,s), 11.51 (1H,s).

Example 84

Synthesis of 3-{[7-chloro-3-(4-chlorobenzenesulfonyl)-2,4(1H,3H)-quinazolinedion-1-yl]acetylamino}-N-carboxymethylpyridinium bromide (Compound 84)

The same method as in Example 29 was used to obtain (quantitatively) from 94 mg (0.13 mmol) of the compound 83 82 mg of the above-identified compound. Properties: colorless crystal, Melting point: 156°–157° C., PMR (δppm, DMSO-$d_6$):4.98 (2H,s), 5.60 (2H,s), 7.40 (1H,d), 7.70 (1H,s), 7.82 (2H,d), 8.00 (1H,d), 8.19 (3H,m), 8.49 (1H,d), 8.79 (1H,d), 9.49 (1H,s), 11.56 (1H,s).

Example 85

Synthesis of [7-chloro-3-(4-chlorobenzenesulfonyl)-2,4(1H,3H)-quinazolinedion-1-yl]-N-(4-pyrimidinyl)acetamide (Compound 85)

The same method as in Example 38 was used to obtain from 300 mg (0.70 mmol) of the compound 29 and 67 mg (0.70 mmol) of 4-aminopyrimidine 60 mg of the above-identified compound (yield 16.9%). Properties: colorless crystal, Melting point: 217°–219° C., PMR (δppm, DMSO-$d_6$):4.96 (2H,s), 7.38 (1H,d), 7.79 (1H,s), 7.81 (2H,d), 7.99 (2H,d), 8.19 (2H,d), 8.68 (1H,d), 8.93 (1H,s), 11.27 (1H,s).

Example 86

Synthesis of [7-chloro-3-(4-chlorobenzenesulfonyl)-2,4(1H,3H)-quinazolinedion-1-yl]-N-isopropylacetamide (Compound 86)

The same method as in Example 38 was used to obtain from 300 mg (0.70 mmol) of the compound 29 and 59 ml (0.70 mmol) of isopropylamine 130 mg of the above-identified compound (yield 39.5%). Properties: colorless crystal, Melting point: 223°–224° C., PMR (δppm, DMSO-$d_6$):1.02 (3H,s), 1.04 (3H,s), 3.81–3.86 (1H,m), 4.58 (2H,s), 7.30 (1H,s), 7.35 (1H,d), 7.79 (2H,d), 7.96 (1H,d), 8.04 (1H,d), 8.17 (2H,d).

Example 87

Synthesis of [7-chloro-3-(4-chlorobenzenesulfonyl)-2,4(1H,3H)-quinazolinedion-1-yl]-N-(4-(2-aminopyrimidinyl))acetamide (Compound 87)

The same method as in Example 38 was used to obtain from 300 mg (0.70 mmol) of the compound 29 and 77 mg (0.70 mmol) of 2,5-diaminopyrimidine 190 mg of the above-identified compound (yield 52.1%). Properties: colorless crystal, Melting point: >200° C. (decomposition), PMR (δppm, DMSO-$d_6$):4.83 (2H,s), 6.49 (2H,s), 7.37 (1H,d), 7.57 (1H,s), 7.89 (2H,d), 7.97 (1H,d), 8.18 (2H,d), 8.34 (2H,s), 10.30 (1H,s).

Example 88

Synthesis of [7-chloro-3-(4-chlorobenzenesulfonyl)-2,4(1H,3H)-quinazolinedion-1-yl]-N-cytosinacetamide (Compound 88)

The same method as in Example 38 was used to obtain from 300 mg (0.70 mmol) of the compound 29 and 85 mg (0.70 mmol) of cytosine 101 mg of the above-identified compound (yield 27.6%). Properties: colorless crystal, Melting point: >200° C. (decomposition), PMR (δppm, DMSO-$d_6$):4.92 (2H,s), 6.96 (1H,d), 7.38 (1H,d), 7.65 (1H,s), 7.80 (2H,d), 7.85 (1H,d), 7.98 (1H,d), 8.19 (2H,d), 11.08 (1H,br), 11.58 (1H,br).

Example 89

Synthesis of [7-chloro-3-(4-methoxybenzenesulfonyl)-2,4(1H,3H)-quinazolinedion-1-yl]-N-(3-pyridyl)acetamide (Compound 89)

The compound 135 was used as the starting substance and the same method was used as in Example 25 to obtain [7-chloro-3-(4-methoxybenzenesulfonyl)-2,4(1H,3H)-quinazolinedion-1-yl]acetic acid t-butyl ester then the same method was used as in Example 29 to obtain [7-chloro-3-(4-methoxybenzenesulfonyl)-2,4(1H,3H)-quinazolinedion-1-yl]acetic acid.

Next, the same method as in Example 38 was used to obtain from 300 mg (0.71 mmol) of [7-chloro-3-(4-methoxybenzenesulfonyl)-2,4(1H,3H)-quinazolinedion-1-yl]acetic acid and 66 mg (0.71 mmol) of 3-aminopyridine 261 mg of the above-identified compound (yield 73.4%). Properties: colorless crystal, Melting point: >200° C. (decomposition), PMR (δppm, DMSO-$d_6$):3.86 (3H,s), 4.88 (2H,s), 7.21 (2H,d), 7.35 (2H,t), 7.62 (1H,s), 7.98 (2H,d), 8.12 (2H,d), 8.28 (1H,d), 8.70 (1H,s), 10.52 (1H,s).

Example 90

Synthesis of 3-{[7-chloro-3-(4-methoxybenzenesulfonyl-2,4(1H,3H)-quinazolinedion-1-yl]acetylamino}-N-ethylpyridinium iodide (Compound 90)

The same method as in Example 56 was used to obtain from 200 mg (0.40 mmol) of the compound 89 229 mg of the above-identified compound (yield 87.2%). Properties: colorless crystal, Melting point: 170°–172° C., PMR (δppm, DMSO-$d_6$):1.50 (3H,t), 3.87 (3H,s), 4.64 (2H,q), 4.97 (2H,s), 7.22 (2H,d), 7.39 (1H,d), 7.65 (1H,s), 7.99 (1H,d), 8.12 (2H,d), 8.37 (1H,d), 8.83 (1H,d), 9.42 (1H,s), 11.40 (1H,s).

Example 91

Synthesis of [7-chloro-3-(4-chlorobenzenesulfonyl)-2,4(1H,3H)-quinazolinedion-1-yl]-N-(5-quinolyl)acetamide (Compound 91)

The same method as in Example 38 was used to obtain from 300 mg (0.70 mmol) of the compound 29 and 101 mg (0.70 mmol) of 5-aminoquinoline 245 mg of the above-identified compound (yield 63.0%). Properties: colorless crystal, Melting point: 218°–220° C., PMR (δppm, DMSO-$d_6$):5.02 (2H,s), 7.39 (1H,d), 7.64 (1H,t), 7.72–7.81 (5H,m), 7.89 (1H,d), 8.00 (1H,d), 8.21 (2H,d), 8.36 (1H,d), 8.92 (1H,d), 10.32 (1H,s).

Example 92

Synthesis of [7-chloro-3-(4-chlorobenzenesulfonyl)-2,4(1H,3H)-quinazolinedion-1-yl]-N-4-(4-t-butoxycarbonylpiperazin-1-yl)acetamide (Compound 92)

The same method as in Example 38 was used to obtain from 500 mg (1.17 mmol) of the compound 29 and 323 mg (1.17 mmol) of 4-(1-t-butoxycarbonylpiperazin-4-yl)aniline 608 mg of the above-identified compound (yield 76.9%). Properties: colorless crystal, Melting point: 195°–197° C., PMR (δppm, DMSO-$d_6$):1.40 (9H,s), 3.02 (4H,br), 3.43(4H, br), 4.80 (2H,s), 6.90 (2H,d), 7.38 (3H,t), 7.55 (1H,s), 7.80 (2H,d), 7.97 (1H,d), 8.18 (2H,d), 10.05 (1H,s).

Example 93

Synthesis of [7-chloro-3-(4-chlorobenzenesulfonyl)-2,4(1H, 3H)-quinazolinedion-1-yl]-N-(4-piperazin-1-yl)acetamide (Compound 93)

The same method as in Example 29 was used to obtain from 406 mg (0.69 mmol) of the compound 92 220 mg of the above-identified compound (yield 54.2%). Properties: colorless crystal, Melting point: 176°–178° C., PMR (δppm, DMSO-$d_6$):3.14–3.21 (8H,m), 4.81 (2H,s), 6.93 (2H,d), 7.34–7.42 (3H,m), 7.55 (1H,s), 7.79 (2H,d), 7.97 (1H,d), 8.18 (2H,d), 10.11 (1H,br).

Example 94

Synthesis of [7-chloro-3-(4-methylbenzenesulfonyl)-2,4 (1H,3H)-quinazolinedion-1-yl]-N-(3-pyridyl)acetamide (Compound 94)

The compound 37 was used as the starting substance and the same method was applied as in Example 25 to obtain [7-chloro-3-(4-methylbenzenesulfonyl)-2,4(1H,3H)-quinazolinedion-1-yl]acetic acid t-butyl ester then the same method was used as in Example 29 to obtain [7-chloro-3-(4-methylbenzenesulfonyl)-2,4(1H,3H)-quinazolinedion-1-yl]acetic acid.

Next, the same method as in Example 38 was used to obtain from 1.0 g (2.45 mmol) of the compound 29 and 230 mg (2.45 mmol) of [7-chloro-3-(4-methylbenzenesulfonyl)-2,4(1H,3H)-quinazolinedion-1-yl]acetic acid 1.0 g of the above-identified compound (yield 84.2%). Properties: colorless crystal, Melting point: 151°–153° C., PMR (δppm, DMSO-$d_6$):2.41 (3H,s), 4.88 (2H,s), 7.35 (2H,t), 7.51 (2H, d), 7.61 (1H,s), 7.97 (2H,d), 8.06 (2H,d), 8.28 (1H,d), 8.70 (1H,d), 10.53 (1H,s).

Example 95

Synthesis of 3-{7-chloro-[3-(4-methylbenzene-sulfonyl)-3-(4-methoxybenzenesulfonyl)-2,4(1H,3H)-quinazolinedion-1-yl]acetylamino}-N-ethylpyridinium iodide (Compound 95)

The same method as in Example 56 was used to obtain from 500 mg (1.03 mmol) of the compound 94 460 mg of the above-identified compound (yield 69.7%). Properties: colorless crystal, Melting point: 157°–159° C., PMR (δppm, DMSO-$d_6$):1.51 (3H,t), 2.42 (3H,s), 4.64 (2H,q), 4.97 (2H, s), 7.39 (1H,d), 7.51 (21,d), 7.64 (1H,s), 7.98–8.11 (4H,m), 8.37 (1H,d), 8.82 (1H,d), 9.41 (1H,s), 11.38 (1H,s).

Example 96

Synthesis of [3-benzenesulfonyl-7-chloro-2,4(1H,3H)-quinazolinedion-1-yl]-N-(3-pyridyl)acetamide (Compound 96)

Compound 11 was used as the starting substance and the same method was applied as in Example 25 to obtain [3-benzenesulfonyl-7-chloro-2,4(1H,3H)-quinazolinedion-1-yl]acetic acid t-butyl ester then the same method was used as in Example 29 to obtain [3-benzenesulfonyl-7-chloro-2, 4(1H,3H)-quinazolinedion-1-yl]acetic acid.

Next, the same method as in Example 38 was used to obtain from 500 mg (1.30 mmol) of [3-benzenesulfonyl-7-chloro-2,4(1H,3H)-quinazolinedion-1-yl]acetic acid and 123 mg (1.30 mmol) of 3-aminopyridine 390 mg of the above-identified compound (yield 63.7%). Properties: colorless crystal, Melting point: >200° C. (decomposition), PMR (δppm, DMSO-$d_6$):4.87 (2H,s), 7.34–7.39 (2H,m), 7.62 (1H,s), 7.70 (2H,t), 7.80 (1H,t), 7.98 (2H,d), 8.19 (2H,d), 8.29 (1H,d), 8.70 (1H,s), 10.50 (1H,s).

Example 97

Synthesis of 3-[(3-benzenesulfonyl-7-chloro-3-(4-methoxybenzenesulfonyl)-2,4(1H,3H)-quinazolinedion-1-yl)acetylamino]-N-ethylpyridinium iodide (Compound 97)

The same method as in Example 56 was used to obtain from 200 mg (0.42 mmol) of the compound 96 100 mg of the above-identified compound (yield 38.0%). Properties: colorless crystal, Melting point: 99°–101° C., PMR (δppm, DMSO-$d_6$):1.52 (3H,t), 4.66 (2H,q), 4.97 (2H,s), 7.41 (1H, d), 7.67 (1H,s), 7.73 (2H,t), 8.01 (1H,d), 8.13 (1H,t), 8.20 (2H,d), 8.39 (1H,t), 8.85 (1H,d), 9.43 (1H,s), 11.40 (1H,s).

Example 98

Synthesis of [7-chloro-3-(4-chlorobenzenesulfonyl)-2,4(1H, 3H)-quinazolinedion-1-yl]-N-(4-S-(2-t-butoxycarbonyl-2-t-butoxycarbonylamino)ethylphenyl)acetamide (Compound 96)

The same method as in Example 38 was used to obtain from 500 mg (1.30 mmol) of the compound 29 and 392 mg (1.17 mmol) of 4-aminobutoxycarbonylmethylaniline 500 mg of the above-identified compound (yield 63.1%). Properties: colorless crystal, Melting point: >200° C. (decomposition), PMR (δppm, DMSO-$d_6$):1.34 (18H,s), 2.79–2.86 (2H,m), 3.95–4.03 (2H,s), 4.83 (2H,s), 7.16 (2H, d), 7.37 (1H,d), 7.43 (2H,d), 7.56 (1H,s), 7.78 (2H,d), 7.98 (1H,d), 8.17 (2H,d), 10.19 (1H,s).

Example 99

Synthesis of [7-chloro-3-(4-chlorobenzenesulfonyl)-2,4(1H, 3H)-quinazolinedion-1-yl]-N-(4-L-phenylalaninyl) acetamide (Compound 99)

The same method as in Example 29 was used to obtain (quantitatively) from 400 mg (0.59 mmol) of the compound 98 310 mg of the above-identified compound. Properties: colorless crystal, Melting point: 191°–193° C., PMR (δppm, DMSO-$d_6$):2.97–3.10 (2H,m), 4.14 (1H,br), 4.85 (2H,s), 7.21 (2H,d), 7.37 (1H,d), 7.50 (2H,d), 7.56 (1H,s), 7.80 (2H,d), 7.98 (1H,d), 8.16–8.21 (4H,m), 10.32 (1H,s).

Example 100

Synthesis of [7-chloro-3-(4-chlorobezenesulfonyl)-2,4 (1H, 3H)-quinazolinedion-1-yl]-N-(2,4-di-t-butoxycarbonylphenyl)acetamide (Compound 100)

The same method as in Example 38 was used to obtain from 500 mg (1.17 mmol) of the compound 29 and 342 mg (1.17 mmol) of 2,4-di-t-butoxycarbonylaniline 239 mg of the above-identified compound (yield 62.3%). Properties: colorless crystal, Melting point: >200° C. (decomposition), PMR (δppm, DMSO-$d_6$):1.57 (18H,s), 4.87 (2H,s), 7.40 (1H,d), 7.65 (1H,s), 7.80 (2H,d), 8.00 (1H,d), 8.11 (1H,s), 8.20 (2H,d), 8.36 (2H,s), 10.68 (1H,s).

Example 101

Synthesis of [7-chloro-3-(4-chlorobenzenesulfonyl)-2,4 (1H,3H)-quinazolinedion-1-yl]-N-(2,4-dicarboxylphenyl) acetamide (Compound 101)

The same method as in Example 29 was used to obtain from 304 mg (0.43 mmol) of the compound 100 239 mg of the above-identified compound (yield 93.8%). Properties: colorless crystal, Melting point: 218°–220° C., PMR (δppm, DMSO-$d_6$):4.86 (2H,s), 7.38 (1H,d), 7.65 (1H,s), 7.78 (2H, d), 7.99 (1H,d), 8.17–8.19 (3H,m), 8.39 (2H,s), 10.62 (1H,s)

Example 102
Synthesis of 7chloro-3-(1-methylpyrrole-3-sulfonyl-2,4(1H,3H)-quinazolinedione (Compound 102)

As the starting substances, methyl 4-chloro-2-phenoxycarbonylaminobenzoate and 1-methylpyrrole-3-sulfonamide were used and the same method was applied as in Example 36 to obtain N-(1-methylpyrrole-3-sulfonyl)-N'-(2-methoxycarbonyl-5-chlorophenyl)urea and further to obtain from 1.89 g (5.08 mmol) of N-(1-methylpyrrole-3-sulfonyl)-N'-(2-carboxy-5-chlorophenyl)urea 712 mg of the above-identified compound (yield 41.3%). Properties: colorless crystal, Melting point: >200° C. (decomposition), PMR (δppm, DMSO-$d_6$):3.71 (3H,s), 6.61 (1H,s), 6.90 (1H,s), 7.12 (1H,s), 7.23 (1H,d), 7.72 (1H,s), 7.86 (1H,d), 11.59 (1H,br).

Example 103
Synthesis of [7-chloro-3-(1-methylpyrrole-3-sulfonyl)-2,4(1H,3H)-quinazolinedion-1-yl]-N-(3-pyridyl)acetamide (Compound 103)

The compound 102 was used as a starting material and the same method as in Example 25 was applied to obtain [7-chloro-3-(1-methylpyrrole-3-sulfonyl)-2,4(1H,3H)-quinazolinedion-1-yl] acetic acid t-butyl ester and further the same method was used as in Example 29 to obtain [7-chloro-3-(1-methylpyrrole-3-sulfonyl)-2,4(1H,3H)-quinazolinedion-1-yl]acetic acid.

Next, the same method as in Example 38 was used to obtain from 410 mg (1.03 mmol) of 3-[7-chloro-3-(1-methylpyrrole-3-sulfonyl)-2,4(1H,3H)-quinazolinedion-1-yl]acetic acid and 97 mg (1.03 mmol) of 3-aminopyridine 45 mg of the above-identified compound (yield 9.2%). Properties: colorless crystal, Melting point: >200° C. (decomposition), PMR (δppm, DMSO-$d_6$):4.92 (2H,s), 6.64 (1H,s), 6.92 (1H,s), 7.36 (1H,d), 7.42 (1H,q), 7.62 (1H,s), 7,76 (1H,s), 7.98 (1H,d), 8.03 (1H,d), 8.33 (1H,d), 8.76 (1H,s), 10.60 (1H,s).

Example 104
Synthesis of 7-chloro-3-(4-ethoxycarbonyl-1-methylpyrazole-5-sulfonly)-2,4(1H,3H)-quinazolinedione (Compound 104)

1.26 g (4.89 mmol) of 1-methyl-4-ethoxycarbonylpyrazol-5-sulfonylisocyanate and 839 mg (4.89 mmol) of 2-amino-4-chlorobenzoic acid were treated in the same way as in Example 1 to obtain 712 mg of the above-identified compound (yield 35.3%). Properties: colorless crystal, Melting point: 222°–224° C., PMR (δppm, DMSO-$d_6$):1.05 (3H,t), 2.09 (3H,s), 4.04 (2H,q), 4.25 (2H,s), 7.15 (1H,s), 7.29 (1H,s), 7.91 (1H,d), 8.02 (1H,s), 11.92 (1H,br).

Example 105
Synthesis of 3-(7-chloro-3-(4-chlorobenzenesulfonyl)-2,4(1H,3H)-quinazolinedion-1-yl) acetylaminophenoxyphosphoric acid (Compound 105)

Into 35 ml of anhydrous THF and 2 ml of dimethylformamide was dissolved 1.00 g (1.92 mmol) of the compound 40, 606 mg (8.65 mmol) of tetrazole and 689 mg (2.88 mmol) of N,N'-diethyl-1,5-dihydro-2,4,3-benzodioxaphosphepin-3-amine were added, then the mixture was agitated at room temperature for one and a half hours. An excess amount of water was poured into the reaction solution and extraction was performed by ethyl acetate. The resultant organic layer was washed with water and saturated saline, then dried over anhydrous magnesium sulfate and concentrated under reduced pressure to obtain a crude product. The obtained crude product was refined by silica gel chromatography (ethyl acetate:n-hexane=1:3) to obtain 687 mg of 3-[7-chloro-3-(4-chlorobenzenesulfonyl)-2,4(1H,3H)-quinazolinedion-1-yl]acetylaminophenoxy-2,4,3-benzodioxaphosphepin.

Next, in 10 ml of dichloromethane was suspended 595 mg (0.87 mmol) of 3-[7-chloro-3-(4-chlorobenzenesulfonyl)-2,4(1H,3H)-quinazolinedion-1-yl]acetylaminophenoxy-2,4,3-benzodioxaphosphepin and the mixture was cooled to −25° C. Under cooling, 256 mg (1.48 mmol) of m-chloroperbenzoic acid was added and the mixture agitated for 30 minutes. An excess amount of water was poured into the reaction solution, then extraction was performed by ethyl acetate. The organic layer was washed by a saturated aqueous solution of sodium hydrogencarbonate, water, and saturated saline, then was dried over magnesium sulfate and concentrated to obtain a crude product of a phosphate. The obtained crude product was suspended in 20 ml of dioxane, then 70 mg of palladium carbon (10%) was added and the mixture was agitated overnight under a flow of hydrogen. The reaction solution was filtered on Celite, then was washed by a small amount of dimethylformamide and the filtrate was concentrated. The obtained oily substance was crystallized by ethyl acetate, then dried to obtain 256 mg of the above-identified compound (yield 49.2%). Properties: colorless crystal, Melting point: >200° C. (decomposition), PMR (δppm, DMSO-$d_6$):4.85 (2H,s), 6.89 (1H,d), 7.27 (1H,t), 7.33–7.40 (2H,m), 7.48 (1H,s), 7.62 (1H,s), 7.81 (2H,d), 7.99 (1H,d), 8.20 (2H,d), 10.41 (1H,s).

Example 106
Synthesis of 1-[4-(2,3-bis-t-butoxycarbonylguanidino) benzyl-7-chloro-3-(4-chlorobenzenesulfonyl)-2,4(1H,3H)-quinazolinedione (Compound 106)

200 mg (0.42 mmol) of the compound 72, 174 mg (0.63 mmol) of N,N'-t-butoxycarbonylthiourea, and 121 mg (0.63 mmol) of 1-(3-dimethylaminopropyl)-3-ethylcarbodiimidechlorate were dissolved in 5 ml of DMF and the mixture was agitated at room temperature for seven hours. The solvent of the reaction solution was distilled off under reduced pressure, then the residue was dissolved in ethyl acetate and washed by a 10% citric acid aqueous solution and saturated saline. The result was dried over magnesium sulfate, then concentrated under reduced pressure. The residue obtained was subjected to silica gel column chromatography and eluted by dichloromethane. The target product fraction was concentrated under reduced pressure, then isopropyl ether was added to the resultant crystal which was then obtained by filtration and heated and dried under reduced pressure to obtain 132 mg of the identified compound (yield 43.7%). Properties: colorless crystal, Melting point: 180° C. (decomposition), PMR (δppm, CDCl$_3$): 1.49 (9H,s), 1.53 (9H,s), 5.17 (2H,s), 7.08–8.33 (11H,m), 10.35 (1H,s), 11.60 (1H,s).

Example 107
Synthesis of 7-chloro-3-(4-chlorobenzenesulfonyl)-1-(4-guanidinobenzyl)-2,4(1H,3H)-quinazolinedione (Compound 107)

The same method as in Example 29 was used to obtain from 218 mg (0.30 mmol) of the compound 106 103 mg of the above-identified compound (yield 65;6%). Properties: colorless crystal, Melting point: 163°–165° C. (decomposition), PMR (δppm, DMSO-$d_6$):5.25 (2H,s), 7.0–8.2 (15H,m).

Example 108
Synthesis of 7-chloro-3-(4-chlorobenzenesulfonyl)-1-phenacyl-2,4(1H,3H)-quinazolinedione (Compound 108)

371 mg of the compound 1 (1.00 mmol) and 239 mg of phenacyl bromide (1.20 mmol) were treated by the same method as in Example 25 to obtain 437 mg of the above-identified compound (yield 89.4%). Properties: colorless crystal, Melting point: 269°–270° C. (decomposition), PMR (δppm, DMSO-$d_6$):5.67 (2H,s), 7.3–8.2 (12H,m).

Example 109
Synthesis of 1-(benzyloxy methyl)-7-chloro-3-(4-chlorobenzenesulfonyl)-2,4(1H,3H)-quinazolinedione (Compound 109)

371 mg of the compound 1 (1.00 mmol) and 192 mg of benzyloxymethyl chloride (1.20 mmol) were treated by the same method as in Example 25 to obtain 407 mg of the above-identified compound (yield 82.9%). Properties: colorless crystal, Melting point: 186°–187° C. (decomposition), PMR (δppm, $CDCl_3$): 4.66 (2H,s), 5.56 (2H,s), 7.1–8.3 (12H,m).

Example 110
Synthesis of [7-chloro-3-(4-chlorobenzenesulfonyl)-2,4(1H, 3H)-quinazolinedion-1-yl]-N-(4-[3-(t-butyloxycarbonyl) propoxy)phenyl)acetamide (Compound 110)

The same method as in Example 38 was used to obtain from 500 mg (1.16 mmol) of the compound 29 and 300 mg (1.19 mmol) of t-butyl 4-(4-aminophenoxy)butyrate 119 mg (1.28 mmol) to 510 mg of the above-identified compound (yield 66.4%). Properties: colorless crystal, Melting point: 204°–205° C., PMR (δppm, DMSO-$d_6$):1.39 (9H,s), 1.8–1.9 (2H, m), 2.34 (2H,t), 3.92 (2H,t), 4.80 (2H,s), 6.87 (2H,d), 7.3–7.5 (3H,m), 7.58 (1H,s), 7.79 (2H,d), 7.97 (1H,d), 8.18 (2H,d), 10.12 (1H,s)

Example 111
Synthesis of [7-chloro-3-(4-chlorobenzenesulfonyl)-2,4(1H, 3H)-quinazolinedion-1-yl]-N-(4-(3-carboxylpropyloxy) phenyl)acetamide (Compound 111)

The same method as in Example 29 was used to obtain from 350 mg (0.53 mmol) of the compound 110 230 mg of the above-identified compound (yield 71.8%). Properties: colorless crystal, Melting point: >200° C. (decomposition), PMR (δppm, DMSO-$d_6$):1.8–2.0 (2H,m), 2.36 (2H,t), 3.93 (2H,t), 4.80 (2H,s), 6.87 (2H,d), 7.3–7.5 (3H,m), 7.58 (1H, s), 7.79 (2H,d), 7.97 (1H,d), 8.18 (2H,d), 10.13 (1H,s)

Example 112
Synthesis of 1-(2-allyloxycarbonylbenzyl)-7-chloro-3-(4-chlorobenzenesulfonyl)-2,4(1H,3H)-quinazolinedione (Compound 112)

1.38 g (6.36 mmol) of 4-chlorobenzenesulfonylisocyanate and 2.00 g (5.78 mmol) of 2-(2-allyloxycarbonylbenzyl) amino-4-chlorobenzoic acid were treated in the same way as in Example 1 to obtain 1.50 g of the above-identified compound (yield 47.6%). Properties: colorless crystal, Melting point: 155°–156° C., PMR (δppm, DMSO-$d_6$):4.83 (2H,d), 5.2–5.5 (4H,m), 6.0–6.2 (1H,m), 7.1–7.2 (2H,m), 7.3–7.5 (5H,m), 7.7–7.8 (2H,m), 7.9–8.1 (2H,m), 8.1–8.2 (2H,m)

Example 113
Synthesis of 1-(2-carboxylbenzyl)-7-chloro-3-(4-chlorobenzenesulfonyl)-2,4(1H,3H)-quinazolinedione (Compound 113)

1.25 g (2.29 mmol) of the compound 112 was treated in the same way as in Example 6 to obtain 704 mg of the above-identified compound (yield 60.7%). Melting point: >250° C., PMR (δppm, DMSO-$d_6$):5.53 (2H,s), 7.1–7.2 (2H,m), 7.3–7.5 (3H,m), 7.7–7.9 (2H,m), 7.9–8.0 (2H,m), 8.1–8.2 (2H,m)

Example 114
Synthesis of 7-chloro-3-(4-chlorobenzenesulfonyl)-1-(3-pyridylmethyl)-2,4(1H,3H)-quinazolinedione (Compound 114)

580 mg (2.68 mmol) of 4-chlorobenzenesulfonylisocyanate and 600 mg (2.28 mmol) of 4-chloro-2-(3-pyridylmethyl)aminobenzoic acid were treated in the same way as in Example 1 to obtain 175 mg of the above-identified compound (yield 16.6%). Properties: colorless crystal, Melting point: >190° C. (decomposition), PMR (δppm, DMSO-$d_6$):5.29 (2H,s), 7.3–7.4 (2H,m), 7.39 (1H,s), 7.68 (1H,d), 7.79 (2H,d), 7.97 (1H,d), 8.20 (2H,d), 8.46 (1H,d), 8.57 (1H,d).

Example 115
Synthesis of 7-chloro-3-(4-chlorobenzenesulfonyl)-1-(2-pyridylmethyl)-2,4(1H,3H)-quinazolinedione (Compound 115)

950 mg (4.35 mmol) of 4-chlorobenzenesulfonylisocyanate and 950 mg (3.61 mmol) of 4-chloro-2-(2-pyridylmethyl)aminobenzoic acid were treated in the same way as in Example 1 to obtain 600 mg of the above-identified compound (yield 36.0%). Properties: colorless crystal, Melting point: >180° C. (decomposition), PMR (δppm, DMSO-$d_6$):5.29 (2H,s), 7.3–7.5 (4H,rn), 7.7–7.8 (3H,m), 7.97 (1H,d), 8.17 (2H,d), 8.48 (1H,d)

Example 116
Synthesis of 7-chloro-3-(4-chlorobenzenesulfonyl)-1-(4-pyridylmethyl)-2,4(1H,3H)-quinazolinedione (Compound 116)

655 mg (3.01 mmol) of 4-chlorobenzenesulfonylisocyanate and 620 mg (2.35 mmol) of 4-chloro-2-(4-pyridylmethyl)aminobenzoic acid were treated in the same way as in Example 1 to obtain 220 mg of the above-identified compound (yield 16.6%). Properties: colorless crystal, Melting point: >240° C. (decomposition), PMR (δppm, DMSO-$d_6$):5.35 (2H,s), 7.2–7.4 (5H,m), 7.4–7.8 (4H,m), 8.01 (1H,d), 8.50 (2H,d), 11.85 (1H,s)

Example 117
Synthesis of 3-{[7-chloro-3-(4-chlorobenzenesulfonyl)-2,4 (1H,3H)-quinazolinedion-1-yl]methyl}-N-ethylpyridinium iodide (Compound 117)

The same method was used as in Example 56 to obtain from 60 mg (0.130 mmol) of the compound 114 60 mg of the above-identified compound (yield 74.6%). Properties: light yellow crystal, Melting point: >150° C. (decomposition), PMR (δppm, DMSO-$d_6$): 1.49 (3H,t), 4.56 (2H,s), 5.43 (2H,s), 7.38 (1H,d), 7.49 (1H,s), 7.80 (2H,d), 8.01 (1H,d), 8.1–8.2 (3H,m), 8.52 (1H,d), 9.0–9.1 (2H,m)

Example 118
4-{[3-(4-chlorobenzenesulfonyl)-7-chloro-2,4(1H,3H)-quinazolinedion-1-yl]methyl}-N-ethylpyridinium iodide (Compound 118)

The same method was used as in Example 56 to obtain from 100 mg (0.217 mmol) of the compound 116 75 mg of the above-identified compound (yield 54.5%). Properties: light yellow crystal, Melting point: >250° C. (decomposition), PMR (δppm, DMSO-$d_6$): 1.51 (3H,t), 4.57 (2H,d), 5.59 (2H,s), 7.3–7.4 (3H,m), 7.58 (1H,d), 8.0–8.1 (3H,m), 8.98 (2H,d), 11.89 (1H,s)

Example 119
Synthesis of 2-{[7-chloro-3-4-chlorobenzenesulfonyl)-2,4 (1H,3H)-quinazolinedion-1-yl]methyl}-N-carboxymethylpyridinium bromide (Compound 119)

The same method as in Example 56 was used to react 40 mg (0.087 mmol) of the compound 114 and 70 μl (0.47 mmol) of t-butyl bromoacetate to synthesize 2-{[3-(4-chlorobenzenesulfonyl)-7-chloro-2,4(1H,3H)-quinazolinedion-1-yl]methyl}-N-t-butyloxycarbonylmethyl-pyridiniumbromide, then the same method as in Example 29 was used to obtain 10 mg of the above-identified compound (yield 19.5%). Properties: colorless crystal, Melting point: >200° C. (decomposition), PMR (δppm, DMSO-d$_6$):5.43 (2H,s), 5.47 (2H,s), 7.38 (1H,d), 7.47 (1H,s), 7.80 (2H,d), 8.01 (1H,d), 8.1–8.2 (2H, m), 8.63 (1H,d), 8.95 (2H,s)

Example 120

Synthesis of 7-chloro-3-[4-(3-pyrazolyl)benzenesulfonyl]-2,4(1H,3H)-quinazolinedione (Compound 120)

As the starting substances, methyl 4-chloro-2-phenoxycarbonylaminobenzoate and 4-(3-pyrazolyl)benzenesulfonamide were used and the same method was applied as in Example 36 to obtain N-[4-(3-pyrazolyl)benzenesulfonyl]-N-(2-methoxycarbonyl-5-chlorophenyl)urea and further to obtain from 1.70 g (4.04 mmol) of N-[4-(3-pyrazolyl)benzenesulfonyl]-N'-(2-carboxyl-5-chlorophenyl)urea 870 mg of the above-identified compound (yield 53.5%). Properties: colorless crystal, Melting point: 124°–126° C. (decomposition), PMR (δppm, CDCl$_3$-CD$_3$OD):6.73 (1H,s), 7.09 (1H,s), 7.16 (2H,d), 7.48 (1H,s), 7.66 (1H,s), 7.9–8.1 (3H,m), 8.32 (2H,d).

Example 121

Synthesis of {7-chloro-3-[4-(3-pyrazolyl)benzenesulfonyl]-2,4(1H,3H)-quinazolinedion-1-yl}-N-(3-pyridlyl)acetamide (Compound 121)

Compound 120 was used as the starting substance and the same method as in Example 25 was applied to obtain {7-chloro-3-[4-(3-pyrazolyl)benzenesulfonyl]-2,4(1H,3H)-quinazolinedion-1-yl}acetic acid t-butyl ester, then the same method was used as in Example 29 to obtain {7-chloro-3-[4-(3-pyrazolyl)benzenesulfonyl]-2,4(1H,3H)-quinazolinedion-1-yl}acetic acid.

Next, the same method as in Example 38 was used to obtain from 200 mg (0.43 mmol) of 3-[7-chloro-3-{7-chloro-3-[4-(3-pyrazolyl)benzenesulfonyl]-2,4(1H,3H)-quinazolinedion-1-yl}acetic acid and 45 mg (0.48 mmol) of 3-aminopyridine 140 mg of the above-identified compound (yield 60.5%). Properties: colorless crystal, Melting point: 238.5°–240° C., PMR (δppm, DMSO-d$_6$):4.87 (2H,s), 6.89 (1H,s), 7.3–7.4 (2H,m), 7.64 (1H,s), 7.8–8.3 (8H,m), 8.70 (1H,s), 10.54 (1H,s).

Example 122

Synthesis of 7-chloro-3-(pyridine-3-sulfonyl)-2,4(1H,3H)-quinazolinedione (Compound 122)

As the starting substances, methyl 4-chloro-2-phenoxycarbonylaminobenzoate and pyridine-3-sulfonamide were used and the same method was applied as in Example 36 to obtain N-(3-pyridine sulfonyl)-N'-(2-methoxycarbonyl-5-chlorophenyl)urea and further to obtain from 1.3 g (3.66 mmol) of N-(3-pyridine sulfonyl)-N'-(2-carboxyl-5-chlorophenyl)urea 1.1 g of the above-identified compound (yield 88.3%). Properties: colorless crystal, Melting point: >226° C. (decomposition), PMR (δppm, DMSO-d$_6$):7.10 (1H,s), 7.24 (1H,d), 7.73 (1H,t), 7.85 (1H,d), 8.50 (1H,d), 7.93 (1H,d), 9.23 (1H,s), 11.68 (1H,s).

Example 123

Synthesis of [7-chloro-3-(pyridine-3-sulfonyl)-2,4-(1H,3H)-quinazolinedion-1-yl]-N-(3-pyridyl)acetamide (Compound 123)

Compound 122 was used as the starting substance and the same method as in Example 25 was applied to obtain [7-chloro-3-(pyridine-3-sulfonyl)-2,4(1H,3H)-quinazolinedion-1-yl]acetic acid t-butyl ester and further the same method as in Example 29 was used to obtain [7-chloro-3-(pyridine-3-sulfonyl)-2,4(1H,3H)-quinazolinedion-1-yl] acetic acid.

Next, the same method as in Example 38 was used to obtain from 300 mg (0.76 mmol) of [7-chloro-3-(pyridine-3-sulfonyl)-2,4(1H,3H)-quinazolinedion-1-yl]acetic acid and 78 mg (0.83 mmol) of 3-aminopyridine 120 mg of the above-identified compound (yield 33.6%). Properties: colorless crystal, Melting point: 262°–263° C., PMR (δppm, DMSO-d$_6$):4.86 (2H,s), 7.36 (2H,m), 7.64 (1H,s), 7.76 (1H,m), 8.00 (2H,d), 8.29 (1H,d), 8.54 (1H,d), 8.71 (1H,s), 8.95 (1H,d), 9.26 (1H,s), 10.50 (1H,s).

Example 124

Synthesis of 3-{[7-chloro-3-(pyridine-3-sulfonyl)-2,4(1H,3H)-quinazolinedion-1-yl]acetylamino}-N-ethylpyridinium iodide (Compound 124)

The same method as in Example 56 was used to obtain from 100 mg (0.21 mmol) of the compound 123 100 mg of the above-identified compound (yield 76.2%). Properties: colorless crystal, Melting point: 156°–159° C., PMR (δppm, DMSO-d$_6$):1.51 (3H,t), 4.64 (2H,q), 4.95 (2H,s), 7.39 (1H, d), 7.42 (1H,s), 7.77 (1H,m), 8.00 (1H,d), 8.12 (1H,m), 8.35 (1H,d), 8.53 (1H,d), 8.83 (1H,d), 8.95 (1H,d), 9.26 (1H,s), 9.42 (1H,s), 11.39 (1H,s).

Example 125

Synthesis of 7-chloro-3-(pyrrole-2-sulfonyl)-2,4(1H,3H)-quinazolinedione (Compound 125)

As the starting substances, methyl 4-chloro-2-phenoxycarbonylaminobenzoate and pyrrole-2-sulfonamide were used and the same method was applied as in Example 36 to obtain N-(pyrrole-2-sulfonyl)-N'-(2-methoxycarbonyl-5-chlorophenyl)urea and further to obtain from 750 mg (2.16 mmol) of N-(pyrrole-2-sulfonyl)-N'-(2-carboxyl-5-chlorophenyl)urea 550 mg of the above-identified compound (yield 77.3%). Properties: colorless crystal, Melting point: >280° C. (decomposition), PMR (δppm, DMSO-d$_6$) :7.10 (1H,s), 7.24 (1H,d), 7.73 (1H,t), 7.85 (1H,d), 8.50 (1H,d), 7.93 (1H,d), 9.23 (1H,s), 11.68 (1H,s).

Example 126

Synthesis of 7-chloro-3-(4-cyanobenzenesulfonyl)-2,4(1H,3H)-quinazolinedione (Compound 126)

1.14 g (5.49 mmol) of 4-cyanobenzenesulfonylisocyanate and 943 mg (5.50 mmol) of 2-amino-4-chlorobenzoic acid were treated in the same way as in Example 1 to obtain 349 mg of the above-identified compound (yield 17.6%). Properties: colorless crystal, Melting point: >250° C. (decomposition), PMR (δppm, DMSO-d$_6$):7.13 (1H,s), 7.24 (1H,d), 7.86 (1H,d), 8.16 (2H,d), 8.32 (2H,d), 11.9 (1H,br).

Example 127

Synthesis of 7-chloro-3-(2-chlorobenzenesulfonyl)-2,4(1H,3H)-quinazolinedione (Compound 127)

1.14 g (5.22 mmol) of 2-chlorobenzenesulfonylisocyanate and 896 mg (5.22 mmol) of 2-amino-4-chlorobenzoic acid were treated in the same way as in Example 1 to obtain 1.00 g of the above-identified compound (yield 51.6%). Properties: colorless crystal, Melting point: 275°–276° C., PMR (δppm, DMSO-d$_6$):7.16 (1H,s), 7.23 (1H,d), 7.63–7.76 (4H, m), 7.86 (1H,d), 8.20 (1H,d), 11.79 (1H,br).

Example 128

Synthesis of 3-(4-chlorobenzenesulfonyl)-1-ethyloxycarbonylmethyl-2,4(1H,3H)-quinazolinedione (Compound 128)

1.00 g of compound 1 (2.70 mmol) and 359 μl (3.24 mmol) of ethyl bromoacetate were treated by the same method as in Example 25 to obtain 1.10 g of the above-identified compound (yield 89.1%). Properties: colorless crystal, Melting point: 208°–209° C., PMR (δppm, CDCl$_3$): 1.28 (3H,t), 4.25 (2H,q), 4.74 (2H,s), 6.91 (1H,s), 7.23 (1H,d), 7.56 (2H,d), 8.06 (1H,d), 8.28 (2H,d).

Example 129
Synthesis of 3(4-chlorobenzenesulfonyl)-1-phenethyl-2,4 (1H,3H)-quinazolinedione (Compound 129)

1.00 g of compound 1(2.70 mmol) and 442 μl of phenethyl bromide (3.24 mmol) were treated in the same method as in Example 25 to obtain 164 mg of the above-identified compound (yield 12.8%). Properties: colorless crystal, Melting point: 200°–202° C., PMR (δppm, CDCl$_3$): 2.98 (2H,t), 4.19 (2H,t), 7.05 (1H,s), 7.18–7.29 (6H,m), 7.56 (2H,d), 8.03 (1H,d), 8.28 (2H,d).

Example 130
Synthesis of 7-chloro-3-(2,5-dichlorobenzenesulfonyl)-2,4 (1H,3H)-quinazolinedione (Compound 130)

1.12 g (4.42 mmol) of 2,5-dichlorobenzenesulfonylisocyanate and 882 mg (4.42 mmol) of 2-amino-4-chlorobenzoic acid were treated in the same way as in Example 1 to obtain 1.06 g of the above-identified compound (yield 58.6%). Properties: colorless crystal, Melting point: 254°–256° C., PMR (δppm, DMSO-d$_6$):7.17 (1H,s), 7.24 (1H,d), 7.71 (1H,d), 7.80–7.89 (2H,m), 8.18 (1H,s).

Example 131
Synthesis of 7-chloro-3-(2,6-dichlorobenzenesulfonyl)-2,4 (1H,3H)-quinazolinedione (Compound 131)

1.12 g (4.42 mmol) of 2,6-dichlorobenzenesulfonylisocyanate and 882 mg (4.42 mmol) of 2-amino- 4-chlorobenzoic acid were treated in the same way as in Example 1 to obtain 725 mg of the above-identified compound (yield 40.5%). Properties: colorless crystal, Melting point: 260°–261° C., PMR (δppm, DMSO-d$_6$):7.18 (1H,s), 7.22 (1H,br), 7.63 (3H,br), 7.88 (1H,d), 11.83 (1H,br).

Example 132
Synthesis of 3-(4-chlorobenzenesulfonyl)-7-methoxy-2,4 (1H,3H)-quinazolinedione (Compound 132)

313 mg (1.44 mmol) of 4-chlorobenzenesulfonylisocyanate and 200 mg (1.20 mmol) of 2-amino-4-methoxybenzoic acid were treated in the same way as in Example 1 to obtain 252 mg of the above-identified compound (yield 62.8%). Properties: colorless crystal, Melting point: 205°–206° C., PMR (δppm, DMSO-d$_6$):3.79 (3H,s), 7.08 (1H,d), 7.28–7.30 (2H,m), 7.75 (2H,d), 8.16 (2H,d), 11.42 (1H,br).

Example 133
Synthesis of 7-methoxy-3-(4-toluenesulfonyl)-2,4(1H,3H)-quinazolinedione (Compound 133)

269 mg (1.36 mmol) of p-toluenesulfonylisocyanate and 190 mg (1.20 mmol) of 2-amino-4-methoxybenzoic acid were treated in the same way as in Example 1 to obtain 211 mg of the above-identified compound (yield 53.5%). Properties: colorless crystal, Melting point: 228°–231° C., PMR (δppm, DMSO-d$_6$):2.43 (3H,s), 3.79 (3H,s), 7.07 (1H,d), 7.29 (2H,br), 7.45–7.54 (2H,m), 8.04 (2H,d), 11.37 (1H,s).

Example 134
Synthesis of 7-chloro-3-(4-chloro-2-fluorobenzenesulfonyl)-2,4(1H,3H)-quinazolinedione (Compound 134)

1.12 g (4.77 mmol) of 4-chloro-2-fluorobenzenesulfonylisocyanate and 819 mg (4.77 mmol) of 2-amino-4-chlorobenzoic acid were treated in the same way as in Example 1 to obtain 742 mg of the above-identified compound (yield 40.0%). Properties: colorless crystal, Melting point: 267°–268° C., PMR (δppm, DMSO-d$_6$):7.16 (1H,s), 7.24 (1H,d), 7.56 (1H,t), 7.73 (1H,d), 7.87 (1H,d), 8.10 (1H,t), 12.2 (1H,br).

Example 135
Synthesis of 7-chloro-3-(4-methoxybenzenesulfonyl)-2,4 (1H,3H)-quinazolinedione (Compound 135)

1.14 g (5.35 mmol) of 4-methoxybenzenesulfonylisocyanate and 938 mg (5.35 mmol) of 2-amino-4-chlorobenzoic acid were treated in the same way as in Example 1 to obtain 938 mg of the above-identified compound (yield 64.3%). Properties: colorless crystal, Melting point: >200° C. (decomposition), PMR (δppm, DMSO-d$_6$):3.88 (3H,s), 7.12 (1H,s), 7.17–7.23 (3H,m), 7.85 (1H,d), 8.10 (2H,d), 11.68 (1H,br).

Example 136
Synthesis of 7-chloro-3-(4-trifluoromethylbenzenesulfonyl) -2,4(1H,3H)-quinazolinedione (Compound 134)

1.67 g (6.67 mmol) of 4-trifluoromethylbenzenesulfonylisocyanate and 1.14 g (6.67 mmol) of 2-amino-4-chlorobenzoic acid were treated in the same way as in Example 1 to obtain 888 mg of the above-identified compound (yield 32.9%). Properties: colorless crystal, Melting point: >200° C. (decomposition), PMR (δppm, DMSO-d$_6$):7.13 (1H,s), 7.23 (1H,d), 7.87 (1H,d), 8.06 (2H,d), 8.39 (2H,d), 11.78 (1H,br).

Example 137
Synthesis of 3-[4-(2-allyloxycarbonylethyloxy) benzenesulfonyl]-7-chloro-2,4(1H,3H)-quinazolinedione (Compound 137)

1.09 g (3.53 mmol) of 4-(2-allyloxycarbonylmethyl) benzenesulfonylisocyanate and 606 mg (3.53 mmol) of 2-amino-4-chlorobenzoic acid were treated in the same way as in Example 1 to obtain 505 mg of the above-identified compound (yield 30.8%). Properties: colorless crystal, Melting point: >200° C. (decomposition), PMR (δppm, DMSO-d$_6$):2.87 (2H,t), 4.35 (2H,t), 4.60 (2H,d), 5.20 (1H,d), 5.30 (1H,d), 5.89–5.94 (1H,m), 7.12 (1H,s), 7.20 (3H,t), 7.85 (1H,d), 8.10 (2H,d).

Example 138
Synthesis of 3-(4-allyloxycarbonylbenzenesulfonyl)-7-chloro-2,4(1H,3H)-quinazolinedione (Compound 138)

1.76 g (6.60 mmol) of 4-allyloxycarbonylbenzenesulfonylisocyanate and 1.13 mg (6.60 mmol) of 2-amino-4-chlorobenzoic acid were treated in the same way as in Example 1 to obtain 965 mg of the above-identified compound (yield 34.8%). Properties: colorless crystal, Melting point: >200° C. (decomposition), PMR (δppm, DMSO-d$_6$):4.87 (2H,d), 5.31 (1H,d), 5.43 (1H,d), 6.00–6.11 (1H,m), 7.12 (1H,s), 7.22 (1H,d), 7.85 (1H,d), 8.23 (2H,d), 8.32 (2H,d), 11.69 (1H,br).

Example 139
Synthesis of 3-[4-(2-carboxyethyloxy)benzenesulfonyl]-7-chloro-2,4(1H,3H)-quinazolinedione (Compound 139)

200 mg (0.43 mmol) of the compound 137 was treated in the same way as in Example 6 to obtain 105 mg of the above-identified compound (yield 57.5%). Melting point: 200° C. or more, PMR (δppm, DMSO-d$_6$):2.73 (2H,t), 4.30 (2H,t), 7.12 (1H,s), 7.20 (3H,t), 7.85 (1H,d), 8.10 (2H,d), 12.09 (1H,br).

Example 140
Synthesis of [7-chloro-3-(4-chlorobenzenesulfonyl)-2,4(1H,3H)-quinazolinedion-1-yl]-N-(4-chlorophenyl)acetamide (Compound 140)

The same method as in Example 38 was used to quantitatively obtain from 300 mg (0.70 mmol) of the compound 29 and 89 mg (0.70 mmol) of 4-chloroaniline 400 mg of the above-identified compound. Properties: colorless crystal, Melting point: >200° C. (decomposition), PMR (δppm, DMSO-$d_6$):4.85 (2H,s), 7.36 (3H,d), 7.60 (3H,t), 7.79 (2H, d), 7.99 (1H,d), 8.19 (2H,d), 10.45 (1H,s).

Example 141
Synthesis of [7-chloro-3-(4-chlorobenzenesulfonyl)-2,4(1H,3H)-quinazolinedion-1-yl]-N-cyclohexylacetamide (Compound 141)

The same method as in Example 38 was used to obtain from 300 mg (0.70 mmol) of the compound 29 and 80 μl (0.70 mmol) of cyclohexylamine 324 mg of the above-identified compound (yield 76.8%). Properties: colorless crystal, Melting point: >200° C. (decomposition), PMR (δppm, DMSO-$d_6$):1.05–1.78 (10H,m), 3.51–3.62 (1H,m), 4.71 (2H,s), 7.38 (1H,d), 7.78–7.82 (3H,m), 8.00 (1H,d), 8.21 (2H,d).

Example 142
Synthesis of 7-chloro-3-[4-(3-ethyloxycarbonylpropyloxy)benzenesulfonyl]-2,4(1H,3H)-quinazolinedione (Compound 142)

763 mg (2.44 mmol) of 4-(3-ethyloxycarbonylpropyloxy)benzenesulfonylisocyanate and 418 mg (2.44 mmol) of 2-amino-4-chlorobenzoic acid were treated in the same way as in Example 1 to obtain 306 mg of the above-identified compound (yield 27.0%). Properties: colorless crystal, Melting point: 167°–169° C., PMR (δppm, DMSO-$d_6$):1.18 (3H,s), 1.98–2.03 (1H,m), 2.46 (2H,t), 4.04–4.14 (4H,m), 7.12 (1H,s), 7.16 (2H,d), 7.21 (1H,d), 7.85 (1H,d), 8.09 (2H,d), 11.58 (1H,s).

Example 143
Synthesis of 7-chloro-3-(2-cyanobenzenesulfonyl)-2,4(1H,3H)-quinazolinedione (Compound 143)

As the starting substances, ethyl 4-chloro-2-phenoxycarbonylaminobenzoate and 2-cyanobenzenesulfonamide were used and the same method was applied as in Example 36 to obtain N-(2-cyanobenzenesulfonyl)-N'-(2-ethyloxycarbonyl-5-chlorophenyl)urea and further to obtain from 1.52 g (3.73 mmol) of N-(2-cyanobenzenesulfonyl)-N'-(2-carboxyl-5-chlorophenyl)urea 810 mg of the above-identified compound (yield 60.1%). Properties: colorless crystal, Melting point: 160°–161° C., PMR (δppm, DMSO-$d_6$):3.71 (3H,s), 6.61 (1H,s), 6.90 (1H,s), 7.12 (1H,s), 7.23 (1H,d), 7.72 (1H,s), 7.86 (1H,d), 11.59 (1H,br).

Example 144
Synthesis of 7-chloro-3-[4-(2-morpholinethyloxy)benzenesulfonyl]-2,4(1H,3H)-quinazolinedione (Compound 144)

As the starting substances, ethyl 4-chloro-2-phenoxycarbonylaminobenzoate and 4-(2-morpholinoethyloxy)benzenesulfonamide were used and the same method was applied as in Example 36 to obtain N-[4-(2-morpholinoethyloxy)benzenesulfonyl]-N'-(2-ethyloxycarbonyl-5-chlorophenyl)urea and further to obtain from 500 mg (0.98 mmol) of N-[4-(2-morpholinoethyloxy)benzenesulfonyl]-N'-(2-carboxyl-5-chlorophenyl)urea 120 mg of the above-identified compound (yield 27.2%). Properties: colorless crystal, Melting point: >200° C. (decomposition), PMR (δppm, DMSO-$d_6$):2.48 (4H,t), 2.73 (2H,t), 3.57 (4H,t), 4.22 (2H,t), 7.12 (1H,s), 7.20 (3H,t), 7.85 (1H,d), 8.09 (2H,d), 11.56 (1H,br).

Example 145
Synthesis of 7-chloro-3-[4-(2-bromoethyloxy)benzenesulfonyl]-2,4(1H,3H)-quinazolinedione (Compound 145)

As the starting substances, ethyl 4-chloro-2-phenoxycarbonylaminobenzoate and 4-(2-bromoethyloxy)benzenesulfonamide were used and the same method was applied as in Example 36 to obtain N-[4-(2-bromoethyloxy)benzenesulfonyl]-N'-(2-ethyloxycarbonyl-5-chlorophenyl)urea and further to obtain from 760 mg (1.50 mmol) of N-[4-(2-bromoethyloxy)benzenesulfonyl]-N'-(2-carboxyl-5-chlorophenyl)urea 320 mg of the above-identified compound (yield 46.4%). Properties: colorless crystal, Melting point: >200° C. (decomposition), PMR (δppm, DMSO-$d_6$):3.82 (2H,t), 4.46 (2H,t), 7.12 (1H,s), 7.12–7.23 (3H,m), 7.85 (1H,d), 8.11 (2H,d), 11.59 (1H,s).

Example 146
Synthesis of 7-chloro-3-{4-[2-(4-phenylpiperazin-1-yl)ethyloxy]benzenesulfonyl}-2,4(1H,3H)-quinazolinedione (Compound 146)

As the starting substances, ethyl 4-chloro-2-phenoxycarbonylaminobenzoate and 4-[2-(4-phenylpiperazin-1-yl)ethyloxy)benzenesulfonamide were used and the same method was applied as in Example 36 to obtain N-{4-[2-(4-phenylpiperazin-1-yl)ethyloxy]benzenesulfonyl}-N'-(2-ethyloxycarbonyl-5-chlorophenyl)urea and to obtain from 813 mg (1.39 mmol) of N-{4-(2-(4-phenylpiperazin-1-yl)ethyloxy] benzenesulfonyl}-N'-(2-carboxy-5-chlorophenyl)urea 115 mg of the above-identified compound (yield 15.3%). Properties: colorless crystal, Melting point: 177°–179° C., PMR (δppm, DMSO-$d_6$):2.65 (4H,t), 2.80 (2H,t), 3.13 (4H,t), 4.26 (2H,t), 6.75 (1H,t), 6.90 (2H,d), 7.12 (1H,s), 7.17–7.22 (5H,m), 7.85 (1H,d), 8.10 (2H,d), 11.59 (1H,br).

Example 147
Synthesis of-7-chloro-3-(4-chloro-2-cyanobenzenesulfonyl)-2,4(1H,3H)-quinazolinedione (Compound 147)

As the starting substances, ethyl 4-chloro-2-phenoxycarbonylaminobenzoate and 4-chloro-2-cyanobenzenesulfonamide were used and the same method was applied as in Example 36 to obtain N-(4-chloro-2-cyanobenzenesulfonyl)-N'-(2-ethyloxycarbonyl-5-chlorophenyl)urea and further to obtain from 1.04 g (2.35 mmol) of N-(4-chloro-2-cyanobenzenesulfonyl)-N'-(2-carboxy-5-chlorophenyl)urea 31 mg of the above-identified compound (yield 3.3%). Properties: colorless crystal, Melting point: >200° C. (decomposition), PMR (δppm, DMSO-$d_6$):7.32–7.36 (2H,m), 7.99 (1H,d), 8.05 (1H,d), 8.38 (1H,d), 8.54 (1H,s), 12.16 (1H,br).

Example 148
Synthesis of 3-(4-aminobenzenesulfonyl)-7-chloro-2,4(1H,3H)-quinazolinedione (Compound 148)

As the starting substances, methyl 4-chloro-2-phenoxycarbonylaminobenzoate and 4-aminobenzenesulfonamide were used and the same method was applied as in Example 36 to obtain N-(4-aminobenzenesulfonyl)-N'-(2-methoxycarbonyl-5-chlorophenyl)urea and further to obtain from 470 mg (1.27 mmol) of N-(4-aminobenzenesulfonyl)-N'-(2-carboxy-5-chlorophenyl)urea 270 mg of the above-identified compound (yield 60.5%). Properties: colorless crystal, Melting point: >250° C. (decomposition), PMR (δppm, DMSO-$d_6$) :6.39 (2H,s), 6.63 (2H,d), 7.09 (1H,s), 7.22 (2H,d), 7.76 (2H,d), 7.83 (2H,d), 11.51 (1H,s).

Example 149

Synthesis of 3-(4-acetylbenzenesulfonyl)-7-chloro-2,4(1H, 3H)-quinazolinedione (Compound 149)

As the starting substances, methyl 4-chloro-2-phenoxycarbonylaminobenzoate and 4-acetylbenzenesulfonamide were used and the same method was applied as in Example 36 to obtain N-(4-acetylbenzenesulfonyl)-N'-(2-methoxycarbonyl-5-chlorophenyl)urea and further to obtain from 300 mg (0.76 mmol) of N-(4-acetylbenzenesulfonyl)-N'-(2-carboxyl-5-chlorophenyl)urea 170 mg of the above-identified compound (yield 59.1%). Properties: colorless crystal, Melting point: >250° C. (decomposition), PMR (δppm, DMSO-$d_6$) :2.64 (3H,s), 7.10 (1H,s), 7.24 (1H,q), 7.85 (1H,d), 8.17 (2H,d), 8.27 (2H,d).

Example 150

Synthesis of 7chloro-3-[4(5-tetrazolyl)benzenesulfonyl]-2,4 (1H,3H)-quinazolinedione (Compound 150)

As the starting substances, methyl 4-chloro-2-phenoxycarbonylaminobenzoate and 4-(5-tetrazolyl) benzenesulfonamide were used and the same method was applied as in Example 36 to obtain N-[4-(5-tetrazolyl) benzenesulfonyl]-N'-(2-methoxycarbonyl-5-chlorophenyl) urea and further to obtain from 2.00 g (4.44 mmol) of N-[4-(5-tetrazolyl)benzenesulfonyl]-N'-(2-carboxyl-5-chlorophenyl)urea 602 mg of the above-identified compound (yield 33.5%). Properties: colorless crystal, Melting point: >200° C. (decomposition), PMR (δppm, DMSO-$d_6$) :7.14 (1H,s), 7.24 (1H,d), 7.87 (2H,d), 8.34 (4H,q), 11.66 (1H,br).

Example 151

Synthesis of 3-(4-chlorobenzenesulfonyl-7-hydroxy-2,4 (1H,3H)-quinazolinedione (Compound 151)

In 15 ml of anhydrous THF was dissolved 423 mg (2.02 mmol) of 4-acetoxy-2-aminobenzoic acid methylester, 485 mg (2.23 mmol) of 4-chlorobenzenesulfonylisocyanate was added, then the mixture was agitated at room temperature for one hour. Water was poured into the reaction solution, then extraction was performed by ethyl acetate and the obtained organic layer was washed, dried, and concentrated to obtain 594 mg (1.39 mmol) of the corresponding sulfonylurea derivative.

Next, the same method was used as in Example 36 to obtain from 594 mg (1.39 mmol) of N-(4-chlorobenzenesulfonyl)-N'-(2-methoxycarbonyl-5-hydroxyphenyl)urea 58 mg of the above-identified compound (yield 8.1%). Properties: colorless crystal, Melting point: 244°–248° C., PMR (δppm, DMSO-$d_6$):6.99 (1H,d), 7.11 (1H,d), 7.20 (1H,s), 7.73 (2H,d), 8.16 (2H,d), 9.67 (1H,s), 11.29 (1H,s).

Example 152

Synthesis of 7-benzyloxy-3-(4-chlorobenzenesulfonyl-2,4 (1H,3H)-quinazolinedione (Compound 152)

The same method as in Example 151 was used to obtain from 886 mg (3.44 mmol) of 2-amino4-benzyloxybenzoic acid methylester and 796 mg (3.44 mmol) of 4-chlorobenzenesulfonylisocyanate 220 mg of the above-identified compound (yield 9.6%). Properties: colorless crystal, Melting point: 206°–207° C., PMR (δppm, $CDCl_3$) :5.08 (2H,s), 6.93 (1H,d), 7.32–7.55 (9H,m), 8.27 (2H,d), 8.58 (1H,br).

Example 153

Synthesis of N-[(3-t-butoxycarzbonyl)-3-5-(t-butoxycarbonylamino)propionyl]-{4-[7-chloro-3-(4-chlorobenzenesulfonyl)-2,4(1H,3H)-quinazolinedion-1-yl]methyl}aniline (Compound 153)

The same method as in Example 38 was used to obtain from 200 mg (0.42 mmol) of the compound 72 and 198 mg (0.42 mmol) of α-O-t-butyl-N-t-butoxycarbonyl-L-asparatic acid 178 mg of the above-identified compound (yield 56.7%). Properties: colorless crystal, Melting point: >200° C. (decomposition), PMR (δppm, DMSO-$d_6$): 1.43 (9H,s), 1.45 (9H,s), 2.83–2.98 (2H,m), 4.41–4.49 (1H,m), 5.16 (2H,s), 6.63 (1H,d), 7.03 (1H,d), 7.06 (1H,s), 7.15–7.20 (4H,m), 7.50 (2H,d), 8.02 (2H,d).

Example 154

Synthesis of N-(β-L-aspartyl)-{4-[7-chloro-3-(4-chlorobenzeneulfonyl)-2,4(1H,3H)-quinazolinedion-1-yl]methyl}aniline (Compound 154)

The same method as in Example 29 was used to obtain from 170 mg (0.23 mmol) of the compound 153 123 mg of the above-identified compound (yield 91.6%). Properties: colorless crystal, Melting point: >200° C. (decomposition), PMR (δppm, DMSO-$d_6$): 2.92 (2H,d), 4.27 (1H,br), 5.20 (2H,s), 7,06 (1H,d), 7.25–7.34 (4H,m), 7.53 (2H,d), 7.80 (2H,d), 7.98 (1H,d), 8.21 (2H,d), 10.26 (1H,br).

Evaluation Example 1

Measurement of Chymase Inhibitive Activity

Human heart chymase was prepared in accordance with the method of Urata et al. (see previous reference), then the inhibitive activity of the quinazoline derivatives of the present invention was measured in the following manner. That is, to 10 μl of a 20 mM trisphosphate buffer (pH 7.5) containing 2MKCl were added 10 μl of purified chymase and 5 μl of a dimethylsulfoxide (hereinafter referred to as DMSO) solution of the test sample. The mixture was pre-incubated at 37° C. for 10 minutes, then 25 μl of a 1 mM Ang I solution was added and the mixture preincubated at 37° C. for 30 minutes. Next, 50 μl of 30% acetic acid was added to stop the enzymatic reaction. At the same time, a blind test was performed by adding, instead of the test sample solution, 5 μl of DMSO and performing the same reaction.

The reacted solution was subjected to high performance liquid chromatography using Develosil ODS-5 (made by Nomura Kagaku, φ4.6 mm×150 mm) and developed at a flow rate of 2.0 ml/min in 0.05% TFA by a straight concentration gradient raising the acetonitrile from 0% to 60% over 10 minutes. This was monitored by the absorbance at 210 nm and the peaks identified by comparison with standard samples of Ang I and Ang II. The peak areas were measured by an integrating meter to quantitatively analyze the Ang I and Ang II and calculate the chymase activity. The chymase inhibitive activity was expressed by a rate of inhibition, that is, the 50% inhibition concentration ($IC_{50}$), based on the blind test value.

The quinazoline derivatives of the present invention all strongly inhibited human chymase at concentrations of 100 μM. The $IC_{50}$ values for typical compounds are shown in Table I.

TABLE I

Enzyme Inhibitive Activity of Compounds
($IC_{50}$, μM)

| Ex. no. | Chymase inhibitive activity |
|---|---|
| 1 | 0.53 |
| 3 | 3.9 |
| 5 | 13.0 |
| 7 | 23.0 |
| 9 | 1.6 |
| 11 | 0.73 |
| 13 | 0.85 |
| 15 | 2.4 |
| 17 | 3.1 |
| 19 | 0.20 |
| 21 | 30.0 |
| 23 | 1.6 |
| 25 | 6.3 |
| 27 | 7.0 |
| 29 | 3.3 |
| 31 | 1.7 |
| 33 | 1.9 |
| 35 | 2.4 |
| 37 | 1.3 |
| 38 | 0.063 |
| 39 | 0.065 |
| 40 | 0.11 |
| 41 | 0.31 |
| 43 | 0.42 |
| 44 | 0.56 |
| 46 | 0.32 |
| 48 | 0.5 |
| 50 | 0.33 |
| 52 | 0.11 |
| 53 | 0.05 |
| 54 | 0.034 |
| 55 | 0.072 |
| 56 | 0.031 |
| 58 | 0.13 |
| 59 | 0.37 |
| 60 | 0.34 |
| 61 | 0.16 |
| 66 | 0.24 |
| 68 | 0.11 |
| 70 | 0.23 |
| 73 | 2.3 |
| 75 | 0.18 |
| 80 | 0.14 |
| 81 | 0.22 |
| 82 | 0.051 |
| 83 | 0.038 |
| 84 | 0.043 |
| 85 | 0.19 |
| 87 | 0.13 |
| 88 | 0.20 |
| 90 | 0.13 |
| 91 | 0.18 |
| 93 | 0.39 |
| 94 | 0.17 |
| 95 | 0.21 |
| 99 | 0.21 |
| 101 | 0.28 |
| 103 | 4.6 |
| 105 | 0.025 |
| 107 | 0.23 |
| 108 | 1.3 |
| 109 | 0.24 |
| 111 | 0.13 |
| 114 | 0.046 |
| 121 | 0.34 |
| 123 | 0.58 |
| 125 | 29 |
| 129 | 3.2 |
| 134 | 1.8 |
| 136 | 0.46 |
| 138 | 1.6 |
| 140 | 0.060 |

TABLE I-continued

Enzyme Inhibitive Activity of Compounds
($IC_{50}$, μM)

| Ex. no. | Chymase inhibitive activity |
|---|---|
| 145 | 1.5 |
| 149 | 0.57 |
| 151 | 2.8 |

Evaluation Example 2
Measurement of Cathepsin G Inhibitive Activity

To a 20 mM trisphosphate buffer (pH 7.5) containing 2MKCl were added 20 μl of human neutrophil derived cathepsin G (made by Carbiochem Co.) dissolved to a concentration of 2 μg/ml and 5 μl of a DMSO solution of the test sample. This was preincubated at 37° C. for 10 minutes, then 25 μl of a 1 mM Ang I solution was added and the result incubated at 37° C. for 30 minutes. Next, 30% acetic acid was added in an amount of 50 μl to stop the enzyme reaction. At the same time, a blind test was performed by adding, instead of the test sample solution, 5 μl of DMSO and causing the same reaction. The reacted solution was treated by high performance liquid chromatography in the same way as Evaluation Example 1 to quantitatively analyze the Ang I and Ang II and calculate the cathepsin G activity. The cathepsin G inhibitive activity was expressed by a rate of inhibition, that is, the 50 percent inhibition concentration ($IC_{50}$), based on the blind test value. The results are shown in Table II.

Evaluation Example 3
Measurement of Chymotrypsin Inhibitive Activity

To 12 μl of 20 mM trisphosphate buffer (pH 7.5) containing 2M KCl were added 8 μl of bovine pancreatic α-chymotrypsin (made by Sigma Co., Type II) dissolved to a concentration of 8 μg/ml in a 20 mM $CaCl_2$ aqueous solution containing 1 mM HCl and 5 μl of a DMSO solution of the test sample. This was preincubated at 37° C. for 10 minutes, then 25 μl of a 1 mM Ang I solution was added and the result incubated at 37° C. for 15 minutes. Next, 30% acetic acid was added in an amount of 50 μl to stop the enzyme reaction. At the same time, a blind test was run using instead of the test sample solution 5 μl of DMSO and performing the same reaction. The reacted solution was, in the same way as Test Example 1, treated by high performance liquid chromatography to quantitatively analyze the Ang I and Ang II and calculate the chymotrypsin activity. The chymotrypsin inhibitive activity was expressed by a rate of inhibition, that is, the 50% inhibition concentration ($IC_{50}$), based on the blind test value. The results are shown in Table II.

TABLE II

Enyzme Inhibiting Activity of Compounds
($IC_{50}$, μM)

| Example no. | Cathepsin g inhibitive activity | Chymotrypsin inhibitive activity |
|---|---|---|
| 1 | 0.52 | 1.5 |
| 3 | 64.4 | 3.5 |
| 5 | 0.34 | 2.0 |
| 7 | 3.2 | 1.9 |

TABLE II-continued

Enyzme Inhibiting Activity of Compounds
($IC_{50}$, μM)

| Example no. | Cathepsin g inhibitive activity | Chymotrypsin inhibitive activity |
|---|---|---|
| 9 | 0.48 | 2.5 |
| 11 | 0.25 | 3.0 |
| 13 | 0.034 | 0.24 |
| 15 | 0.79 | 4.8 |
| 17 | 0.58 | 25.0 |
| 19 | 0.16 | 0.40 |
| 21 | 37.0 | 8.5 |
| 23 | 3.8 | 12.0 |
| 25 | 37.0 | 34.5%* |
| 27 | 16.0 | 27.0%* |
| 29 | 14.02 | 46.5%* |
| 31 | 1.1 | 5.7 |
| 33 | 3.6 | 4.6 |
| 35 | 24.9*%* | 1.4 |
| 37 | 1.2 | 6.1 |

*Expressed by percent inhibition at 100 μM

Preparation Example 1
Production of Tablets 100.0 g of compound 1 was mixed with microcrystalline cellulose in an amount of 22.5 g and magnesium stearate in an amount of 2.5 g and then tabletized by a single-action type tabletizing machine to produce tablets each containing 200 mg of the compound 1 and having a diameter of 9 mm and a weight of 250 mg.

Preparation Example 2
Production of Granules 30 g of the compound 19 was mixed well with lactose in an amount of 265 g and magnesium stearate in an amount of 5 g. The mixture was pressed molded, then pulverized and the granules sieved to obtain excellent 10% granules of 20 to 50 mesh.

Preparation Example 3
Production of Suppository

Vitepsol H-15 (made by Dynamite Nobel Co.) was warmed to melt. To this was added the compound 19 to a concentration of 12.5 mg/ml. This was homogeneously mixed, then was added in 2 ml amounts to a rectal suppository mold and cooled to obtain rectal suppositories each containing 25 mg of the compound 19.

INDUSTRIAL APPLICABILITY

According to the present invention, it is possible to provide a pharmaceutical composition containing a quinazoline derivative or pharmaceutically acceptable salt thereof as an effective ingredient, a chymase inhibitor, a medicament for the prevention or treatment of cardiac and circulatory system diseases derived from the abnormal exacerbation of Ang II production, and a novel quinazoline derivative useful as said pharmaceutical compositions. In humans, there are at least two paths for conversion of Ang I to Ang II. One path involves ACE and the other path involves chymase. Therefore, inhibition of chymase can be considered to lead to the prevention or treatment of various cardiac and circulatory system diseases derived from the abnormal exacerbation of Ang II production even in areas where ACE inhibitors do not exhibit any effect. As examples of such diseases, cardiac insufficiency, hypercardia, stasis cardiac diseases, hypertension, arthrosclerosis, peripheral circulatory disorders, revasoconstriction after PCTA, diabetic renal disorders or non-diabetic renal disorders, etc. may be given as examples. The present invention provides a method of prevention or treatment useful for diseases for which there had been no effective method of prevention or treatment in the past.

We claim:

1. A pharmaceutical composition comprising a quinazoline derivative or a pharmaceutically acceptable salt thereof in a pharmaceutically effective amount, and a pharmaceutically acceptable carrier therefor, the quinazoline derivative having the general formula (1):

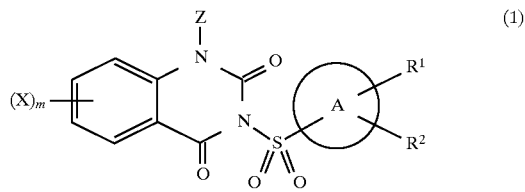

wherein the ring A represents a benzene ring, a pyridine ring, a pyrrole ring, or a pyrazole ring, m represents 0, 1, or 2, X represents a hydroxy group, a nitro group, a halogen atom, a $C_1$ to $C_4$ lower alkyl group which may be substituted with a halogen atom, a $C_1$ to $C_4$ lower alkoxy group which may be substituted with a halogen atom, or a $C_7$ to $C_{12}$ aralkyloxy group, or X together with the benzene ring which is shown as substituted with said X, represents a group forming a naphthalene ring or a quinoline ring, $R^1$ and $R^2$ are the same or different and represent a hydrogen atom, a halogen atom, a $C^1$ to $C^4$ lower alkyl group which may be substituted with a halogen atom, a nitro group, a cyano group, a pyrazolyl group, a tetrazolyl group, a carboxyl group which may be esterified with a $C_1$ to $C_4$ lower alkyl group or an allyl group, or a $C_1$ to $C_4$ lower alkoxy group which may be substituted with one or more substituent groups selected from the group consisting of a halogen atom, a morpholino group, a phenylpiperazinyl group, and a carboxyl group which may be esterified with a $C_1$ to $C_4$ lower alkyl group or an allyl group, or, when the ring A represents a benzene ring $R^1$ and $R^2$ together with benzene ring which is shown as substituted with said $R^1$ and $R^2$ represent a group forming a naphthalene ring or a quinoline ring, and Z represents a hydrogen atom, a $C_1$ to $C_4$ lower alkyl group which may be substituted with a halogen atom, a $C_2$ to $C_5$ alkenyl group, an unsubstituted or substituted aralkyl group, an unsubstituted or substituted aromatic heterocyclic alkyl group, a carboxymethyl group which may be esterified with a $C_1$ to $C_4$ lower alkyl group or an allyl group, a carbonylmethyl group which is amidized with a primary or secondary or cyclic amine, an unsubstituted or substituted arylcarbonylmethyl group, or an unsubstituted or substituted aralkyloxymethyl group.

2. A pharmaceutical composition for inhibiting chymase comprising a quinazoline derivative or a pharmaceutically acceptable salt thereof in an amount effective for inhibiting chymase and a pharmaceutically acceptable carrier therefor, the quinazoline derivative having the general formula (1):

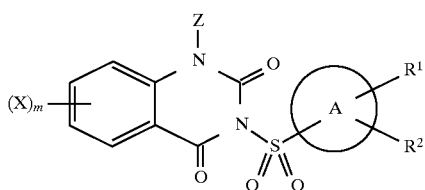

(1)

wherein the ring A represents a benzene ring, a pyridine ring, a pyrrole ring, or a pyrazole ring, m represents 0, 1, or 2, X represents a hydroxy group, a nitro group, a halogen atom, a $C_1$ to $C_4$ lower alkyl group which may be substituted with a halogen atom, a $C_1$ to $C_4$ lower alkoxy group which may be substituted with a halogen atom or a $C_7$ to $C_{12}$ aralkyloxy group, or X together with the benzene ring which is shown as substituted with said X represents a group forming a naphthalene ring or a quinoline ring, $R^1$ and $R^2$ are the same or different and represent a hydrogen atom, a halogen atom, a $C_1$ to $C_4$ lower alkyl group which may be substituted with a halogen atom, a nitro group, a cyano group, a pyrazolyl group, a tetrazolyl group, a carboxyl group which may be esterified with a $C_1$ to $C_4$ lower alkyl group or an allyl group, or a $C_1$ to $C_4$ lower alkoxy group which may be substituted with one or more substituent groups selected from the group consisting of a halogen atom, a morpholino group, a phenylpiperazinyl group, and a carboxyl group which may be esterified with a $C_1$ to $C_4$ lower alkyl group or an allyl group, or, when the ring A represents a benzene ring, $R^1$ and $R^2$ together with the benzene ring which is shown as substituted with said $R^1$ and $R^2$ represent a group forming a naphthalene ring or a quinoline ring, and Z represents a hydrogen atom, a $C_1$ to $C_4$ lower alkyl group which may be substituted with a halogen atom, a $C_2$ to $C_5$ alkenyl group, an unsubstituted or substituted aralkyl group, an unsubstituted or substituted aromatic heterocyclic alkyl group, a carboxymethyl group which may be esterified with a $C_1$ to $C_4$ lower alkyl group or an allyl group, a carbonylmethyl group which is amidized with a primary or secondary or cyclic amine, an unsubstituted or substituted arylcarbonylmethyl group, or an unsubstituted or substituted aralkyloxymethyl group.

3. A pharmaceutical composition for the treatment of cardiac and circulatory system diseases derived from the abnormal exacerbation of angiotensin II production comprising a quinazoline derivative or a pharmaceutically acceptable salt thereof in an amount effective for treatment of said cardiac and circulatory system diseases, and a pharmaceutically acceptable carrier therefor, said quinazoline derivative having the general formula (1):

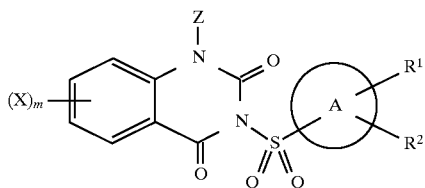

(1)

wherein the ring A represents a benzene ring, a pyridine ring, a pyrrole ring, or a pyrazole ring, m represents 0, 1, or 2, X represents a hydroxy group, a nitro group, a halogen atom, a $C_1$ to C4 lower alkyl group which may be substituted with a halogen atom, a C1 to $C_4$ lower alkoxy group which may be substituted with a halogen atom, or a $C_7$ to $C_{12}$ aralkyloxy group, or X together with the benzene ring which is shown as substituted with said X represents a group forming a naphthalene ring or a quinoline ring, $R^1$ and $R^2$ are the same or different and represent a hydrogen atom, a halogen atom, a $C_1$ to $C_4$ lower alkyl group which may be substituted with a halogen atom, a nitro group, a cyano group, a pyrazolyl group, a tetrazolyl group, a carboxyl group which may be esterified with a $C_1$ to $C_4$ lower alkyl group or an allyl group, or a $C_1$ to $C_4$ lower alkoxy group which may be substituted with one or more substituent groups selected from the group consisting of a halogen atom, a morpholino group, a phenylpiperazinyl group, and a carboxyl group which may be esterified with a $C_1$ to $C_4$ lower alkyl group or an allyl group, or, when the ring A represents a benzene ring $R^1$ and $R^2$ together with the benzene ring which is shown as substituted with said $R^1$ and $R^2$ represent a group forming a naphthalene ring or a quinoline ring, and Z represents a hydrogen atom, a $C_1$ to $C_4$ lower alkyl group which may be substituted with a halogen atom, a $C_2$ to $C_5$ alkenyl group, an unsubstituted or substituted aralkyl group, an unsubstituted or substituted aromatic heterocyclic alkyl group, a carboxymethyl group which may be esterified with a $C_1$ to $C_4$ lower alkyl group or an allyl group, a carbonylmethyl group which is amidized with a primary or secondary or cyclic amine, an unsubstituted or substituted arylcarbonylmethyl group, or an unsubstituted or substituted aralkyloxymethyl group.

4. A method for treatment as claimed in claim 1, wherein the cardiac and circulatory system disease derived from the abnormal exacerbation of angiotensin II production is a cardiac and circulatory system disease selected from cardiac insufficiency, hypercardia, stasis cardiac diseases, and hypertension.

5. A method for treatment as claimed in claim 1, wherein the cardiac and circulatory system disease derived from the abnormal exacerbation of angiotensin II production is a cardiac and circulatory system disease selected from artherosclerosis, peripheral circulatory disorders, and revasoconstriction after percutaneous transluminal coronary angioplasty.

6. A method for treatment as claimed in claim 11, wherein the cardiac and circulatory system disease derived from the abnormal exacerbation of angiotensin II production is a cardiac and circulatory system disease selected from diabetic renal disorders or non-diabetic renal disorders.

7. A pharmaceutical composition comprising a quinazoline derivative or a pharmaceutically acceptable salt thereof in a pharmaceutically effective amount, and a pharmaceutically acceptable carrier thereof, the quinazoline derivative having the general formula (1a):

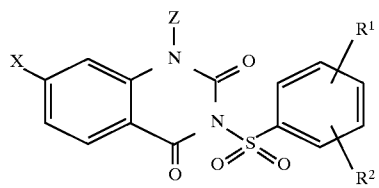

(1a)

wherein X represents a hydroxy group, a nitro group, a halogen atom, a $C_1$ to $C_4$ lower alkyl group which may be substituted with a halogen atom, a $C_1$ to $C_4$ lower alkoxy group which may be substituted with a halogen atom, or a $C_7$ to $C_{12}$ aralkyloxy group, or X together with the benzene ring which is shown as substituted with said X, represents a group forming a naphthalene ring or a quinoline ring, $R^1$ and $R^2$ are the same or different and represent a hydrogen atom, a halogen atom, a $C_1$ to $C_4$ lower alkyl group which may be substituted with a halogen atom, a nitro group, a cyano group, a pyrazolyl group, a tetrazolyl group, a carboxyl group which may be esterified with a $C_1$ to $C_4$ lower alkyl group or an allyl group, or a $C_1$ to $C_4$ lower alkoxy group which may be substituted with one or more substituent groups selected from the group consisting of a halogen atom, a morpholino group, a phenylpiperazinyl group, and a carboxyl group which may be esterified with a $C_1$ to $C_4$ lower alkyl group or an allyl group, or, $R^1$ and $R^2$ together with the benzene ring which is shown as substituted with said $R^1$ and $R^2$, represent a group forming a naphthalene ring or a quinoline ring, and Z represents a hydrogen atom, a $C_1$ to $C_4$ lower alkyl group which may be substituted with a halogen atom, a $C_2$ to $C_5$ alkenyl group, an unsubstituted or substituted aralkyl group, an unsubstituted or substituted aromatic heterocyclic alkyl group, a carboxylmethyl group which may be esterified with a $C_1$ to $C_4$ lower alkyl group or an allyl group, a carbonylmethyl group which is amidized with a primary or secondary or cyclic amine, an unsubstituted or substituted arylcarbonylmethyl group, or an unsubstituted or substituted aralkyloxymethyl group.

8. A quinazoline derivative having the general formula (1'), or a pharmaceutically acceptable salt thereof:

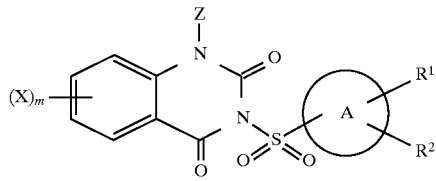

(1')

wherein the ring A represents a benzene ring, a pyridine ring, a pyrrole ring, or a pyrazole ring, m represents 0, 1, or 2, X represents a hydroxy group, nitro group, halogen atom, a $C_1$ to $C_4$ lower alkyl group which may be substituted with a halogen atom, a $C_1$ to $C_4$ lower alkoxy group which may be substituted with a halogen atom, or a $C_7$ to $C_{12}$ aralkyloxy group, or X together with the benzene ring which is shown as substituted with said X, represents a group forming a naphthalene ring or a quinoline ring, $R^1$ and $R^2$ are the same or different and represent a hydrogen atom, a halogen atom, a $C_1$ to $C_4$ lower alkyl group which may be substituted with a halogen atom, a nitro group, a cyano group, a pyrazolyl group, a tetrazolyl group, a carboxyl group which may be esterified with a $C_1$ to $C_4$ lower alkyl group or an allyl group, or a $C_1$ to $C_4$ lower alkoxy group which may be substituted with one or more substituent groups selected from the group consisting of a halogen atom, a morpholino group, a phenylpiperazinyl group, and a carboxyl group which may be esterified with a $C_1$ to $C_4$ lower alkyl group or an allyl group, or, when the ring A represents a benzene ring $R^1$ and $R^2$ together with the benzene ring which is shown as substituted with said $R^1$ and $R^2$, represent a group forming a naphthalene ring or a quinoline ring, and Z represents a hydrogen atom, a $C_1$ to $C_4$ lower alkyl group which may be substituted with a halogen atom, a $C_2$ to $C_5$ alkenyl group, an unsubstituted or substituted aralkyl group, an unsubstituted or substituted aromatic heterocyclic alkyl group, a carboxylmethyl group which may be esterified with a $C_1$ to $C_4$ lower alkyl group or an allyl group, a carbonylmethyl group which is amidized with a primary or secondary or cyclic amine, an unsubstituted or substituted arylcarbonylmethyl group, or an unsubstituted or substituted aralkyloxymethyl group, and when the ring A represents a benzene ring, Z represents a hydrogen atom and m represents 0, $R^1$ and $R^2$ do not simultaneously represent a hydrogen atom;

when the ring A represents a benzene ring, Z represents a hydrogen atom, m represents 0 and one of $R^1$ or $R^2$ is a hydrogen atom, the other of $R^1$ or $R^2$ represents neither a methyl group nor a chlorine atom;

and when the ring A represents a benzene ring, Z represents a hydrogen atom, m represents 1 and both of $R^1$ and $R^2$ simultaneously represent a hydrogen atom, X does not represent a chlorine atom.

9. A quinazoline derivative having the general formula (1a), or a pharmaceutically acceptable salt thereof:

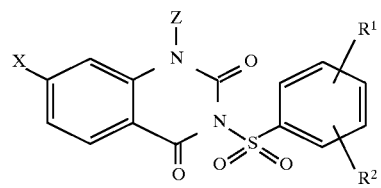

(1a)

wherein X represents a hydroxy group, a nitro group, a halogen atom, a $C_1$ to $C_4$, lower alkyl group which may be substituted with a halogen atom, a $C_1$ to $C_4$ lower alkoxy group which may be substituted with a halogen atom, or a $C_7$ to $C_{12}$ aralkyloxy group, or X together with the benzene ring which is shown as substituted with said X, represents a group forming a naphthalene ring or a quinoline ring, $R^1$ and $R^2$ are the same or different and represent a hydrogen atom, a halogen atom, a $C_1$ to $C_4$ lower alkyl group which may be substituted with a halogen atom, a nitro group, a cyano group, a pyrazolyl group, a tetrazolyl group, a carboxyl group which may be esterified with a $C_1$ to $C_4$ lower alkyl group or an allyl group, or a $C_1$ to $C_4$ lower alkoxy group which may be substituted with one or more substituent groups selected from the group consisting of a halogen atom, a morpholino group, a phenylpiperazinyl group, and a carboxyl group which may be esterified with a $C_1$ to $C_4$ lower alkyl group or an allyl group, or, $R^1$ and $R^2$ together with the benzene ring which is shown as substituted with said $R^1$ and $R^2$ represent a group forming a naphthalene ring or a quinoline ring, and Z represents a hydrogen atom, a $C_1$ to $C_4$ lower alkyl group which may be substituted with a halogen atom, a $C_2$ to $C_5$ alkenyl group, an unsubstituted or substituted aralkyl group, an unsubstituted or substituted aromatic heterocyclic alkyl group, a carboxymethyl group which may be esterified with a $C_1$ to $C_4$ lower alkyl group or an allyl group, a carbonylmethyl group which is amidized with a primary or secondary or cyclic amine, an unsubstituted or substituted arylcarbonylmethyl group, or an unsubstituted or substituted aralkyloxymethyl group.

10. A method for the treatment of cardiac and circulatory system diseases derived from the abnormal exacerbation of angiotensin II production in a patient comprising administering to the patient a pharmaceutical composition according to claim 3 in an amount effective for treatment of said cardiac and circulatory system diseases.

11. A method of inhibiting chymase in a patient comprising administering to the patient a pharmaceutical composition according to claim 2 in a amount effective to inhibit chymase.

12. A method for the treatment of cardiac and circulatory system diseases derived from the abnormal exacerbation of angiotensin II production in a patient comprising administering to the patient a quinazoline derivative having the general formula (1'), or a pharmaceutically acceptable salt thereof, according to claim 8 in an amount effective for treatment of said cardiac and circulatory system diseases.

13. A method of inhibiting chymase in a patient comprising administering to the patient a quinazoline derivative having the general formula (1'), or a pharmaceutically acceptable salt thereof, according to claim 8 in a amount effective to inhibit chymase.

14. A method for the treatment of cardiac and circulatory system diseases derived from the abnormal exacerbation of angiotensin II production in a patient comprising administering to the patient a quinazoline derivative having the general formula (1a), or a pharmaceutically acceptable salt thereof, according to claim 9 in an amount effective for treatment of said cardiac and circulatory system diseases.

15. A method of inhibiting chymase in a patient comprising administering to the patient a quinazoline derivative having the general formula (1a), or a pharmaceutically acceptable salt thereof, according to claim 9 in a amount effective to inhibit chymase.

16. A method for treatment as claimed in claim 12, wherein the cardiac and circulatory system disease derived from the abnormal exacerbation of angiotensin II production is a cardiac and circulatory system disease selected from cardiac insufficiency, hypercardia, stasis cardiac diseases, and hypertension.

17. A method for treatment as claimed in claim 12, wherein the cardiac and circulatory system disease derived from the abnormal exacerbation of angiotensin II production is a cardiac and circulatory system disease selected from artherosclerosis, peripheral circulatory disorders, and revasoconstriction after percutaneous transluminal coronary angioplasty.

18. A method for treatment as claimed in claim 12, wherein the cardiac and circulatory system disease derived from the abnormal exacerbation of angiotensin II production is a cardiac and circulatory system disease selected from diabetic renal disorders or non-diabetic renal disorders.

19. A method for treatment as claimed in claim 14, wherein the cardiac and circulatory system disease derived from the abnormal exacerbation of angiotensin II production is a cardiac and circulatory system disease selected from cardiac insufficiency, hypercardia, stasis cardiac diseases, and hypertension.

20. A method for treatment as claimed in claim 14, wherein the cardiac and circulatory system disease derived from the abnormal exacerbation of angiotensin II production is a cardiac and circulatory system disease selected from artherosclerosis, peripheral circulatory disorders, and revasoconstriction after percutaneous transluminal coronary angioplasty.

21. A method for treatment as claimed in claim 14, wherein the cardiac and circulatory system disease derived from the abnormal exacerbation of angiotensin II production is a cardiac and circulatory system disease selected from diabetic renal disorders or non-diabetic renal disorders.

* * * * *